US007105305B2

(12) United States Patent
Williams et al.

(10) Patent No.: US 7,105,305 B2
(45) Date of Patent: Sep. 12, 2006

(54) HUMAN PLATELET-DERIVED GROWTH FACTOR RECEPTORS

(75) Inventors: Lewis T. Williams, Tiburon, CA (US); Jaime A. Escobedo, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 527 days.

(21) Appl. No.: 10/027,400

(22) Filed: Dec. 19, 2001

(65) Prior Publication Data

US 2003/0017535 A1  Jan. 23, 2003

Related U.S. Application Data

(63) Continuation of application No. 08/461,917, filed on Jun. 5, 1995, now Pat. No. 6,372,438, which is a continuation of application No. 08/226,243, filed on Apr. 11, 1994, now abandoned, which is a continuation of application No. 07/650,794, filed on Jan. 31, 1991, now abandoned, which is a continuation-in-part of application No. 07/309,322, filed on Feb. 10, 1989, now abandoned, which is a continuation-in-part of application No. 07/151,414, filed on Feb. 2, 1988, now abandoned.

(51) Int. Cl.
*G01N 33/53* (2006.01)
*C07K 14/49* (2006.01)

(52) U.S. Cl. ......................................... 435/7.1; 530/350
(58) Field of Classification Search ................. 435/7.1; 530/350
See application file for complete search history.

(56) References Cited

U.S. PATENT DOCUMENTS 4,766,073 A    8/1988    Murray et al.

FOREIGN PATENT DOCUMENTS

EP    0 325 224    7/1989
EP    0 327 369    8/1989
WO    90/10013     9/1990

OTHER PUBLICATIONS

Panela et al., Cellular Signalling (2003), vol. 5: pp. 973-981, esp. p. 973.*
Kazlauskas et al., Cell (1989), vol. 58: pp. 1121-1133, esp. pp. 1127 and 1129.*
Sporn et al., The Journal of Clinical investigations (1986), vol. 78: pp. 329-332 esp. p. 330.*
Matsui et al., Science 1989, vol. 243(4892): pp. 800-804.*
Gronwald et al., Proc Natl Acad Sci U S A 1988, vol. 85(10): pp. 3435-3439.*
Escobedo et al., Mol cell Biol. 1991, vol. 11(2): pp. 1125-1132.*

Anderson et al., "Binding of SH2 Domains of Phospholipase Cγ1, GAP, and Src to Activated Growth Factor Recieptors," *Science*, 250:979-982 (1990).
Bell, et al., "Effect of Platelet Factors on Migration of Cultured Bovine Aortic Endothelial and Smooth Muscle Cells," *Circulation Research*, 65(4):1057-1065.
Betsholtz et al., "Coexpression of a PDGF-like Growth Factor and PDGF Receitpr: in Human Osteosarcoma Cell Line: Implications for Autocrine Receptor Activation," *Cell*, 39:447-457 (1984).
Bishayee et al., "Ligand-induced Dimerization of the Platelet-derived Growth Factor Receptor," *J. Biol. Chem.*, 264(20):11699-11705 (1989).
Claesson-Welsh et al., "cDNA cloning and expression of human platelet-derive growth factor (PDGF) receptor specific for B-chain-containing PDGF Molecules," *Mol. Cell. Biol.*. 8(8):3476-3486 (1988).
Claesson-Welsh et al., "cDNA cloning and expression of the human A-type platelet-derived growth factor (PDGF) receptor establishes structural similarity to the B-type PDGF receptor," *Proc. Nat'l Acad. Sci. USA*, 86:4917-4921 (1989).
Coughlin et al., "Role of Phosphatidylinositol Kinase in PDGF Receptor Signal Transduction," *Science*, 243:1191-1194 (1989).
Daniel et al., "Purification of the platelet-derived growth factor receptor by using an anti-phosphotyrosine antibody," *Proc. Nat'l Acad. Sci. USA*. 82:2684-2687 (1985).
Daniel et al., "Biosynthetic and Glycosylation Stufies of Cell Surface Platelet Derived Growth Factor Receptors," *J. Biol. Chem.*, 262(20):9778-9784 (1987).
Escobedo et al., "Role of Tyrosine Kinase and Membrane-Spanning Domains in Signal Transduction by the Platelet-Derived Growth Factor Receptor," *Mol. Cell Biol.*, 8(12):5126-5131 (1988).
Escobedo et al., "Platelet-derived Growth Factor Receptors Expressed by cDNA Transfection Couple to a Diverse Group of Cellular Responses Associated With Cell Proliferation," *J. Biol. Chem.*, 263(3):1482-1487 (1988).

(Continued)

*Primary Examiner*—Marianne P. Allen
(74) *Attorney, Agent, or Firm*—Townsend and Townsend and Crew, LLP

(57) ABSTRACT

DNA sequences encoding human platelet-derived growth factor receptors (hPDGF-R), and expression constructs comprising sequences which encode a receptor that can be secreted or incorporated into the membrane of a mammalian cell. Peptide fragments with functions equivalent to the wild-type receptor, conferring a PDGF-sensitive mitogenic response on cells lacking the receptor are provided. The constructs can be used for enhancing PDGF response of cells, determining the regions involved in transducing the signal in response to PDGF binding, providing mutated analogs and evaluating drugs for their physiologic activity. Soluble fragments comprising PDGF receptor sequences are also provided, including important intracellular kinase insert sequences which interact with intracellular proteins.

6 Claims, 6 Drawing Sheets

OTHER PUBLICATIONS

Escobedo et al., "A PDGF Receptor Domain Essential For Mitogenesis But Not For Many Other Responses to PDGF," *Nature*, 335:85-87 (1988).

Escobedo et al., "A Common PDGF Receptor is Activated By Homodimeric A and B Forms of PDGF," *Science*, 240:1532-1534 (1988).

Escobedo et al., A Phosphatidylinositol-3 Kinase Binds to Platelet-Derived Growth Factor Receptors Through a Specific Receptor Sequence Containing Phosphotyrosine, *Molecular and Cellular Biology*, 11:1125-1132 (1991).

Fantl et al., "Mutations of the Platelet-Derived Growth Factor Receptor that Cause a Loss of Ligand-Induced Conformational Change, Subtle Changes in Kinase Activity, and Impaired Ability to Stimulate DNS Synthesis," *Mol. Cell. Biol.*, 9(10):4473-4478 (1989).

Felder et al., "Kinase Activity Controls the Sorting of the Epidermal Growth Factor Receptor Within the Multivesicular Body," *Cell*, 61:623-634 (1990).

Giese et al., "The Role of Individual Cysteine Residues in the Structure and Function of the v-sis Gene Product," *Science*, 236:1315-1318 (1987).

Glenn et al., "Platelet-derived Growth Factor," *J. Biol. Chem.*, 257(9):5172-517? (1982).

Graves et al., "Evidence that a Human Osteosarcoma Cell Line Which Secretes a Mitogen Similar to Platelet-Derived Growth Factor Requires Growth Factors Present In Platelet-Poor Plasma," *Cancer Research* 43:83-87 (1983).

Gronwald et al., "Cloning and expression of a cDNA coding for the human platelet-derived growth factor receptor: Evidence for more than one receptor class," *Proc. Nat'l Acad. Sci. USA.*, 85:3435-3439 (1988).

Hart et al., "Synthesis, Phosphorylation, and Degradation of Multiple Forms of the Platelet-derived Growth Factor Receptor Studied Using a Monoclonal Antibody," *J. Biol. Chem.*, 262(22):10780-10785 (19987).

Hart et al., "Two classes of PDGF Receptor Recognize Different Isoforms of PDGF," *Science*, 240:1529-1531 (1988).

Hart et al., "Expression of Secreted Human Immunoglobulin/PDGF-Receptor Fusion Proteins Which Demonstrate High Affinity Ligand Binding," *Miami Winter Cancer Symposium* (1989).

Haynes et al., "Constitutive, long-term production of human interferons by hamster cells containing multiple copies of a cloned interferon gene," *Nucl. Acids Res.*. 11(3):687-706 (1983).

Heidaran et al., "Chimeric α- and β-Platelet-derived Growth Factor (PDGF) Receptors Define Three Immunoglobulin-like Domains of the α-PDGF Receptor That Determine PDGF-AA Binding Specificity," *J. Biol. Chem.*, 265(31):18741-18744.

Heldin et al., "Interaction of Platelet-derived Growth Factor with Its Fibroblast Receptor," *J. Biol. Chem.*, 257(8):4216-4221 (1982).

Heldin et al., "Binding of different dimeric forms of PDGF to human fibroblasts evidence for two separate receptor types," *EMBO J.*, 7(5):1387-1393 (1988).

Heldin et al., "Dimerization of B-type Platelet-derived Growth Factor Receptors Occurs After Ligand Binding and Is Closely Associated With Receptor Kinase Activation," *J. Biol. Chem.*, 264(15):8905-8912 (1989).

Jacobs et al., Isolation and Characterization of Genomic and cDNA Clones of Human Erythropoietin,: *Nature 313*:806-810 (1985).

Kaplan et al., "PDGF β-Receptor Stimulates Tyrosine Phosphorylation of GAP and Association of GAP with a Signaling Complex," *Cell*, 61:125-133 (1990).

Kazlauskas et al., Different effects of homo- and heterodimers of platelet-derived growth factor A and B chains on human and mouse fibroblasts,: *EMBO J.*, 7(12):3727-3735 (1988).

Kazlauskas et al., "Phosphorylation of the PDGF Receptor β Subunit Creates a Tight Binding Site for Phosphatidylinositol 3 Kinase", *The EMBO Journal*, 9:3279-3286 (1990).

Keating et al., "Processing of the Platelet-derived Growth Factor Receptor," *J. Biol. Chem.*, 262(16):7932-7937 (1987).

Keating et al., "Autocrine Stimulation of Intracellular PDGF Receptors in v-si Transformed Cells," *Science*, 239:914-916 (1988).

Keating et al., "Ligand Activation Causes a Phosphorylation-dependent Change in Platelet-derived Growth Factor Receptor Conformation," *J. Biol. Chem.*, 263(26):12805-12808 (1988).

Keating et al., "Platelet-derived Growth Factor Receptor Inducibility is Acquired Immediately After Translation and Does Not Require Glycosylation," *J. Biol. Chem.*, 264(16):9129-9132 (1989).

Kimball et al., "Epidermal Growth Factor (EGF) Binding to Membranes Immobilize in Microtiter Wells and Estimation of EGF-Related Transforming Growth Factor Activity," *Biochimica et Biophysica Acta*, 771:82-88 (1984).

Kornbluth et al., "Novel Tyrosine Kinase Identified by Phosphotyrosine Antibodic Screening of cDNA Libraries," *Mol. Cell. Biol.*, 8(12):5541-5544 (1988).

Kypta et al., "Association between the PDGF Receptor and Members of the *src* family of Tyrosine Kinases," *Cell*, 62:481-492 (1990).

Marx, "Oncogenes Evoke New Cancer Therapies," *Science* , 249:1376-1378 (1990).

Matsui et al., "Isolation of a Novel Receptor cDNA Establishes the Existence of Two PDGF Receptor Genes," *Science*, 243:800-804 (1989).

Matsui et al., "Independent expression of human α or β platelet-derived growth factor receptor cDNAs in a naive hematopoietic cell leads to functional coupling with mitogenic and chemotactic signaling pathways," *Proc. Natl. Acad. Sci. USA* 86:8314-8318 (1989).

Moran et al., "Src homology region 2 domains direct protein-protein interactions in signal transduction," *Proc. Nat'l. Acad. Sci. USA*, 87:8622-8626 (1990).

Morrison et al., "Direct Activation of the Serine/Threonine Kinase Activity of Raf-1 through Tyrosine Phosphorylation by the PDGF β-Receptor," *Cell*, 58:649-6_ (1989).

Morrison et al., "Platelet-Derived Growth Factor (PDGF)—Dependent Association Phospholipase C-γ with the PDGF Receptor Signaling Complex," *Mol. Cell. Biol.*, 10(5):2359-2366 (1990).

Nishibe et al., "Increase of the Catalytic Activity of Phospholipase C-γ1 by Tyrosine Phosphorylation," *Science*, 250:1253-1256 (1990).

Nister et al., "A Glioma-Derived PDGF A Chain Homodimer Has Different Function Activities from a PDGF AB Heterodimer Purified from Human Platelets," *Cell*, 52:791-799 (1988).

Orchansky et al., "Phosphatidylinositol Linkage of a Truncated Form of the Platelet-derived Growth Factor Receptor," *J. Biol. Chem.*, 263(29):15159-15165 (1988).

Peralta et al., "Primary Structure and Biochemical Properties of an $M_2$ Muscarinic Receptor," *Science*, 236:600-605 (1987).

Qiu et al., "Primary Structure of *ckit*: relationship with the CSF-1/PDGF receptor kinase family—oncogenic activation of v-*kit* involves deletion of extracellular domain and C terminus," *EMBO J.*, 7(4):1003-1011 (1988).

Reid et al., "Two forms of the basic fibroblast growth factor receptor-like mP are expressed in the developing mouse brain," *Proc. Nat'l Acad. Sci. USA*, 87:1596-1600 (1990).

Ronnstrand et al., "Purification of the Receptor for Platelet-derived Growth Factor from Porcine Uterus," *J. Biol. Chem.*, 262(7):2929-2932 (1987).

Roussel et al., "Transforming potential of the *c-fms* proto-oncogene (CSF-1 receptor)," *Nature*, 325:549-552 (1987).

Ruta et al., "A novel protein tyrosine kinase gene whose expression is modulated during endothelial cell differentiation," *Oncogene*, 3:9-15 (1988).

Seifert et al., "Two Different Subunits Associate to Create Isoform-specific Platelet-derived Growth Factor Receptors," *J. Biol. Chem.*, 264(15):8771-8778 (1989).

Smith et al., "Blocking of HIV-1 Infectivity by a Soluble, Secreted Form of the CD4 Antigen," *Science*, 238:1704-1707 (1987).

Ullrich et al., "Signal Transduction by Receptors with Tyrosine Kinase Activity," *Cell*, 61:203-212 (1990).

Van Der Schaal et al., "An Enzyme-Linked Lectin Binding Assay for Quantitative Determination of Lectin Receptors," *Anal. Biochem.*, 140:48-55 (1984).

Van Driel et al., "Stoichiometric Binding of Low Density Lipoprotein (LDL) Monoclonal Antibodies to LDL Receptors in a Solid Phase Assay," *J. Biol. Chem.*, 264(16):9533-9538 (1989).

Williams et al., "Platelet-derived growth factor binds specifically to receptors on vascular smooth muscle cells and the binding becomes nondissociable," *Proc. Nat'l Acad. Sci. USA*, 79:5867-5870 (1982).

Williams et al., "Platelet-derived Growth Factor Receptors Form a High Affinity State in Membrane Preparations," *J. Biol. Chem.*, 259(8):5287-5294 (1984).

Williams et al., "PDGF Receptors: Structural and Functional Studies," *Miami Winter Symposium*, ICSU Short Reports, 4:168-171 (1986).

Williams et al., "The Stimulation of Paracrine and Autocrine Mitogenic Pathways by the Platelet-Derived Growth Factor Receptor," *J. Cell. Physiol. Supp.*, 5:27-30 (1987).

Williams, "Signal Transduction by the Platelet-Derived Growth Factor Receptor," *Science*, 243:1564-1570 (1989).

Williams et al., "The Immunoglobulin Superfamily—Domains for Cell Surface Recognition," *Ann. Rev. Immunology*, 6:381-405 (1988).

Williams, "Stimulation of Paracrine and Autocrine Pathways of Cell Proliferation by Platelet-Derived Growth Factor," *Clinical Research*, 36(1):5-10 (1988).

Williams, "Signal Transduction by the Platelet-Derived Growth Factor Receptor Involves Association of the Receptor with Cytoplasmic Molecules," *Clinical Research*, 37:564-568 (1989).

Williams et al., "Signal Transduction by the Platelet-Derived Growth Factor Receptor," *CSH Symp. Quant. Biol.*, 53:455-465 (1988).

Yarden et al., "Structure of the receptor for platelet-derived growth factor helps define a family of closely related growth factor receptors," *Nature*, 323:226-232 (1986).

Yarden et al., "Growth Factor Receptor Tyrosine Kinases," *Ann. Rev. Biochem.*, 57:443-478 (1988).

\* cited by examiner

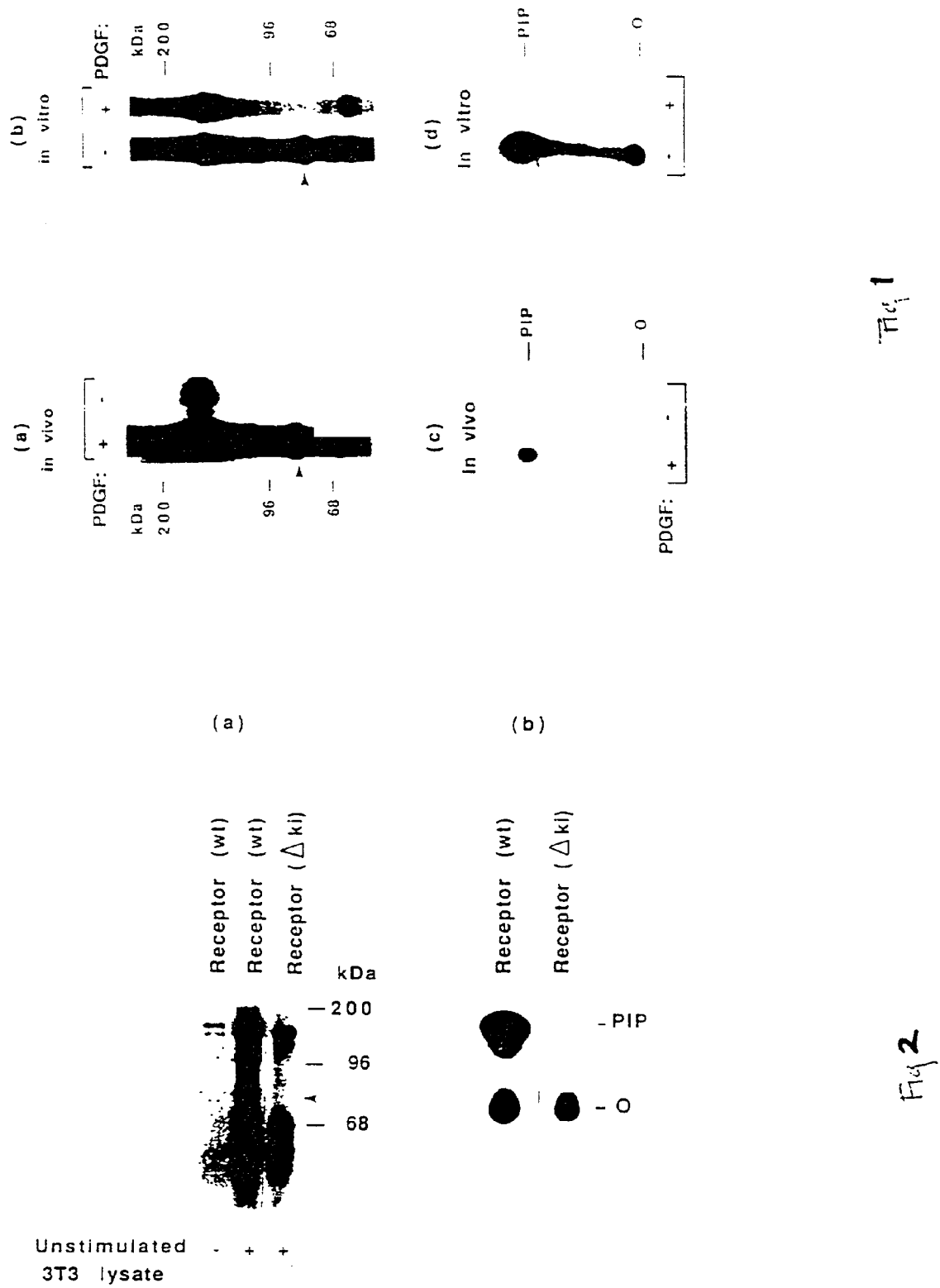

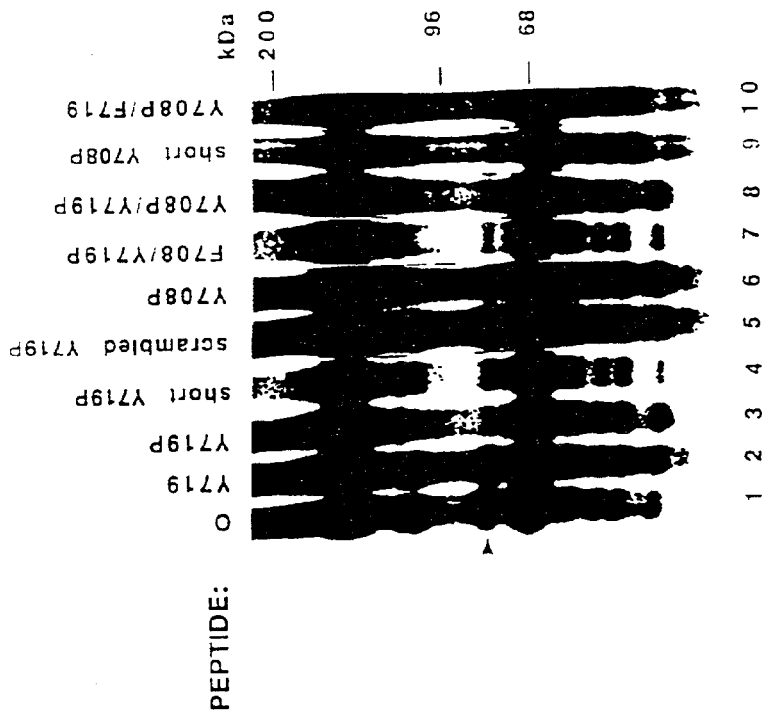
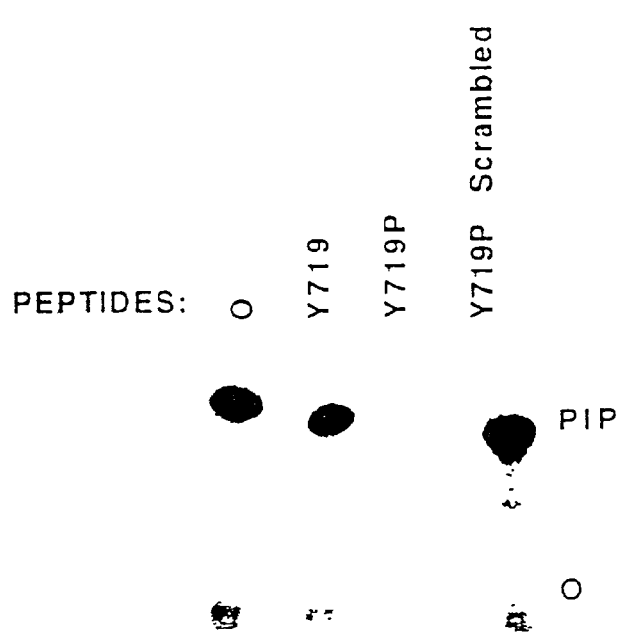
Fig. 4

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
     (A) LENGTH: 6373 base pairs
     (B) TYPE: nucleic acid
     (C) STRANDEDNESS: single
     (D) TOPOLOGY: linear (ii) MOLECULE TYPE: cDNA (ix) FEATURE:
     (A) NAME/KEY: CDS
     (B) LOCATION: 129..3398

(xi) SEQUENCE DESCRIPTION: SEQ ID NO: 1:

```
TTGGAGCTAC AGGGAGAGAA ACAGAGGAGG AGACTGCAAG AGATCATTGG AGGCCGTGGG        60

CACGCTCTTT ACTCCATGTG TGGGACATTC ATTGCGGAAT AACATCGGAG GAGAAGTTTC       120

CCAGAGCT ATG GGG ACT TCC CAT CCG GCG TTC CTG GTC TTA GGC TGT CTT       170
         Met Gly Thr Ser His Pro Ala Phe Leu Val Leu Gly Cys Leu
           1               5                  10

CTC ACA GGG CTG AGC CTA ATC CTC TGC CAG CTT TCA TTA CCC TCT ATC        218
Leu Thr Gly Leu Ser Leu Ile Leu Cys Gln Leu Ser Leu Pro Ser Ile
 15                  20                  25                  30

CTT CCA AAT GAA AAT GAA AAG GTT GTG CAG CTG AAT TCA TCC TTT TCT        266
Leu Pro Asn Glu Asn Glu Lys Val Val Gln Leu Asn Ser Ser Phe Ser
                 35                  40                  45

CTG AGA TGC TTT GGG GAG AGT GAA GTG AGC TGG CAG TAC CCC ATG TCT        314
Leu Arg Cys Phe Gly Glu Ser Glu Val Ser Trp Gln Tyr Pro Met Ser
         50                  55                  60

GAA GAA GAG AGC TCC GAT GTG GAA ATC AGA AAT GAA GAA AAC AAC AGC        362
Glu Glu Glu Ser Ser Asp Val Glu Ile Arg Asn Glu Glu Asn Asn Ser
 65                  70                  75

GGC CTT TTT GTG ACG GTC TTG GAA GTG AGC AGT GCC TCG GCG GCC CAC        410
Gly Leu Phe Val Thr Val Leu Glu Val Ser Ser Ala Ser Ala Ala His
         80                  85                  90

ACA GGG TTG TAC ACT TGC TAT TAC AAC CAC ACT CAG ACA GAA GAG AAT        458
Thr Gly Leu Tyr Thr Cys Tyr Tyr Asn His Thr Gln Thr Glu Glu Asn
 95                 100                 105                 110

GAG CTT GAA GGC AGG CAC ATT TAC ATC TAT GTG CCA GAC CCA GAT GTA        506
Glu Leu Glu Gly Arg His Ile Tyr Ile Tyr Val Pro Asp Pro Asp Val
                115                 120                 125

GCC TTT GTA CCT CTA GGA ATG ACG GAT TAT TTA GTC ATC GTG GAG GAT        554
Ala Phe Val Pro Leu Gly Met Thr Asp Tyr Leu Val Ile Val Glu Asp
        130                 135                 140

GAT GAT TCT GCC ATT ATA CCT TGT CGC ACA ACT GAT CCC GAG ACT CCT        602
Asp Asp Ser Ala Ile Ile Pro Cys Arg Thr Thr Asp Pro Glu Thr Pro
145                 150                 155

GTA ACC TTA CAC AAC AGT GAG GGG GTG GTA CCT GCC TCC TAC GAC AGC        650
Val Thr Leu His Asn Ser Glu Gly Val Val Pro Ala Ser Tyr Asp Ser
160                 165                 170

AGA CAG GGC TTT AAT GGG ACC TTC ACT GTA GGG CCC TAT ATC TGT GAG        698
Arg Gln Gly Phe Asn Gly Thr Phe Thr Val Gly Pro Tyr Ile Cys Glu
175                 180                 185                 190

GCC ACC GTC AAA GGA AAG AAG TTC CAG ACC ATC CCA TTT AAT GTT TAT        746
Ala Thr Val Lys Gly Lys Lys Phe Gln Thr Ile Pro Phe Asn Val Tyr
                195                 200                 205

GCT TTA AAA GCA ACA TCA GAG CTG GAT CTA GAA ATG GAA GCT CTT AAA        794
Ala Leu Lys Ala Thr Ser Glu Leu Asp Leu Glu Met Glu Ala Leu Lys
        210                 215                 220

ACC GTG TAT AAG TCA GGG GAA ACG ATT GTG GTC ACC TGT GCT GTT TTT        842
Thr Val Tyr Lys Ser Gly Glu Thr Ile Val Val Thr Cys Ala Val Phe
225                 230                 235
```

-continued

| | |
|---|---|
| AAC AAT GAG GTG GTT GAC CTT CAA TGG ACT TAC CCT GGA GAA GTG AAA<br>Asn Asn Glu Val Val Asp Leu Gln Trp Thr Tyr Pro Gly Glu Val Lys<br>240                   245                   250 | 890 |
| GGC AAA GGC ATC ACA ATG CTG GAA GAA ATC AAA GTC CCA TCC ATC AAA<br>Gly Lys Gly Ile Thr Met Leu Glu Glu Ile Lys Val Pro Ser Ile Lys<br>255                   260                 265                270 | 938 |
| TTG GTG TAC ACT TTG ACG GTC CCC GAG GCC ACG GTG AAA GAC AGT GGA<br>Leu Val Tyr Thr Leu Thr Val Pro Glu Ala Thr Val Lys Asp Ser Gly<br>                275                   280                   285 | 986 |
| GAT TAC GAA TGT GCT GCC CGC CAG GCT ACC AGG GAG GTC AAA GAA ATG<br>Asp Tyr Glu Cys Ala Ala Arg Gln Ala Thr Arg Glu Val Lys Glu Met<br>                   290                   295                 300 | 1034 |
| AAG AAA GTC ACT ATT TCT GTC CAT GAG AAA GGT TTC ATT GAA ATC AAA<br>Lys Lys Val Thr Ile Ser Val His Glu Lys Gly Phe Ile Glu Ile Lys<br>                 305                   310                 315 | 1082 |
| CCC ACC TTC AGC CAG TTG GAA GCT GTC AAC CTG CAT GAA GTC AAA CAT<br>Pro Thr Phe Ser Gln Leu Glu Ala Val Asn Leu His Glu Val Lys His<br>320                   325                   330 | 1130 |
| TTT GTT GTA GAG GTG CGG GCC TAC CCA CCT CCC AGG ATA TCC TGG CTG<br>Phe Val Val Glu Val Arg Ala Tyr Pro Pro Pro Arg Ile Ser Trp Leu<br>335                   340                   345                350 | 1178 |
| AAA AAC AAT CTG ACT CTG ATT GAA AAT CTC ACT GAG ATC ACC ACT GAT<br>Lys Asn Asn Leu Thr Leu Ile Glu Asn Leu Thr Glu Ile Thr Thr Asp<br>                   355                   360                 365 | 1226 |
| GTG GAA AAG ATT CAG GAA ATA AGG TAT CGA AGC AAA TTA AAG CTG ATC<br>Val Glu Lys Ile Gln Glu Ile Arg Tyr Arg Ser Lys Leu Lys Leu Ile<br>                   370                   375                 380 | 1274 |
| CGT GCT AAG GAA GAA GAC AGT GGC CAT TAT ACT ATT GTA GCT CAA AAT<br>Arg Ala Lys Glu Glu Asp Ser Gly His Tyr Thr Ile Val Ala Gln Asn<br>                   385                   390                 395 | 1322 |
| GAA GAT GCT GTG AAG AGC TAT ACT TTT GAA CTG TTA ACT CAA GTT CCT<br>Glu Asp Ala Val Lys Ser Tyr Thr Phe Glu Leu Leu Thr Gln Val Pro<br>400                   405                   410 | 1370 |
| TCA TCC ATT CTG GAC TTG GTC GAT GAT CAC CAT GGC TCA ACT GGG GGA<br>Ser Ser Ile Leu Asp Leu Val Asp Asp His His Gly Ser Thr Gly Gly<br>415                   420                   425                430 | 1418 |
| CAG ACG GTG AGG TGC ACA GCT GAA GGC ACG CCG CTT CCT GAT ATT GAG<br>Gln Thr Val Arg Cys Thr Ala Glu Gly Thr Pro Leu Pro Asp Ile Glu<br>                   435                   440                 445 | 1466 |
| TGG ATG ATA TGC AAA GAT ATT AAG AAA TGT AAT AAT GAA ACT TCC TGG<br>Trp Met Ile Cys Lys Asp Ile Lys Lys Cys Asn Asn Glu Thr Ser Trp<br>                   450                   455                 460 | 1514 |
| ACT ATT TTG GCC AAC AAT GTC TCA AAC ATC ATC ACG GAG ATC CAC TCC<br>Thr Ile Leu Ala Asn Asn Val Ser Asn Ile Ile Thr Glu Ile His Ser<br>                   465                   470                 475 | 1562 |
| CGA GAC AGG AGT ACC GTG GAG GGC CGT GTG ACT TTC GCC AAA GTG GAG<br>Arg Asp Arg Ser Thr Val Glu Gly Arg Val Thr Phe Ala Lys Val Glu<br>                   480                   485                 490 | 1610 |
| GAG ACC ATC GCC GTG CGA TGC CTG GCT AAG AAT CTC CTT GGA GCT GAG<br>Glu Thr Ile Ala Val Arg Cys Leu Ala Lys Asn Leu Leu Gly Ala Glu<br>495                   500                   505                510 | 1658 |
| AAC CGA GAG CTG AAG CTG GTG GCT CCC ACC CTG CGT TCT GAA CTC ACG<br>Asn Arg Glu Leu Lys Leu Val Ala Pro Thr Leu Arg Ser Glu Leu Thr<br>                   515                   520                 525 | 1706 |
| GTG GCT GCT GCA GTC CTG GTG CTG TTG GTG ATT GTG ATC ATC TCA CTT<br>Val Ala Ala Ala Val Leu Val Leu Leu Val Ile Val Ile Ile Ser Leu<br>                   530                   535                 540 | 1754 |
| ATT GTC CTG GTT GTC ATT TGG AAA CAG AAA CCG AGG TAT GAA ATT CGC<br>Ile Val Leu Val Val Ile Trp Lys Gln Lys Pro Arg Tyr Glu Ile Arg | 1802 |

-continued

```
                 545                  550                  555
TGG AGG GTC ATT GAA TCA ATC AGC CCA GAT GGA CAT GAA TAT ATT TAT       1850
Trp Arg Val Ile Glu Ser Ile Ser Pro Asp Gly His Glu Tyr Ile Tyr
    560                  565                  570

GTG GAC CCG ATG CAG CTG CCT TAT GAC TCA AGA TGG GAG TTT CCA AGA       1898
Val Asp Pro Met Gln Leu Pro Tyr Asp Ser Arg Trp Glu Phe Pro Arg
575                  580                  585                  590

GAT GGA CTA GTG CTT GGT CGG GTC TTG GGG TCT GGA GCG TTT GGG AAG       1946
Asp Gly Leu Val Leu Gly Arg Val Leu Gly Ser Gly Ala Phe Gly Lys
                 595                  600                  605

GTG GTT GAA GGA ACA GCC TAT GGA TTA AGC CGG TCC CAA CCT GTC ATG       1994
Val Val Glu Gly Thr Ala Tyr Gly Leu Ser Arg Ser Gln Pro Val Met
        610                  615                  620

AAA GTT GCA GTG AAG ATG CTA AAA CCC ACG GCC AGA TCC AGT GAA AAA       2042
Lys Val Ala Val Lys Met Leu Lys Pro Thr Ala Arg Ser Ser Glu Lys
625                  630                  635

CAA GCT CTC ATG TCT GAA CTG AAG ATA ATG ACT CAC CTG GGG CCA CAT       2090
Gln Ala Leu Met Ser Glu Leu Lys Ile Met Thr His Leu Gly Pro His
    640                  645                  650

TTG AAC ATT GTA AAC TTG CTG GGA GCC TGC ACC AAG TCA GGC CCC ATT       2138
Leu Asn Ile Val Asn Leu Leu Gly Ala Cys Thr Lys Ser Gly Pro Ile
655                  660                  665                  670

TAC ATC ATC ACA GAG TAT TGC TTC TAT GGA GAT TTG GTC AAC TAT TTG       2186
Tyr Ile Ile Thr Glu Tyr Cys Phe Tyr Gly Asp Leu Val Asn Tyr Leu
                 675                  680                  685

CAT AAG AAT AGG GAT AGC TTC CTG AGC CAC CAC CCA GAG AAG CCA AAG       2234
His Lys Asn Arg Asp Ser Phe Leu Ser His His Pro Glu Lys Pro Lys
        690                  695                  700

AAA GAG CTG GAT ATC TTT GGA TTG AAC CCT GCT GAT GAA AGC ACA CGG       2282
Lys Glu Leu Asp Ile Phe Gly Leu Asn Pro Ala Asp Glu Ser Thr Arg
705                  710                  715

AGC TAT GTT ATT TTA TCT TTT GAA AAC AAT GGT GAC TAC ATG GAC ATG       2330
Ser Tyr Val Ile Leu Ser Phe Glu Asn Asn Gly Asp Tyr Met Asp Met
    720                  725                  730

AAG CAG GCT GAT ACT ACA CAG TAT GTC CCC ATG CTA GAA AGG AAA GAG       2378
Lys Gln Ala Asp Thr Thr Gln Tyr Val Pro Met Leu Glu Arg Lys Glu
735                  740                  745                  750

GTT TCT AAA TAT TCC GAC ATC CAG AGA TCA CTC TAT GAT CGT CCA GCC       2426
Val Ser Lys Tyr Ser Asp Ile Gln Arg Ser Leu Tyr Asp Arg Pro Ala
                 755                  760                  765

TCA TAT AAG AAG AAA TCT ATG TTA GAC TCA GAA GTC AAA AAC CTC CTT       2474
Ser Tyr Lys Lys Lys Ser Met Leu Asp Ser Glu Val Lys Asn Leu Leu
        770                  775                  780

TCA GAT GAT AAC TCA GAA GGC TTA ACT TTA TTG GAT TTG TTG AGC TTC       2522
Ser Asp Asp Asn Ser Glu Gly Leu Thr Leu Leu Asp Leu Leu Ser Phe
785                  790                  795

ACC TAT CAA GTT GCC CGA GGA ATG GAG TTT TTG GCT TCA AAA AAT TGT       2570
Thr Tyr Gln Val Ala Arg Gly Met Glu Phe Leu Ala Ser Lys Asn Cys
    800                  805                  810

GTC CAC CGT GAT CTG GCT GCT CGC AAC GTT CTC CTG GCA CAA GGA AAA       2618
Val His Arg Asp Leu Ala Ala Arg Asn Val Leu Leu Ala Gln Gly Lys
815                  820                  825                  830

ATT GTG AAG ATC TGT GAC TTT GGC CTG GCC AGA GAC ATC ATG CAT GAT       2666
Ile Val Lys Ile Cys Asp Phe Gly Leu Ala Arg Asp Ile Met His Asp
                 835                  840                  845

TCG AAC TAT GTG TCG AAA GGC AGT ACC TTT CTG CCC GTG AAG TGG ATG       2714
Ser Asn Tyr Val Ser Lys Gly Ser Thr Phe Leu Pro Val Lys Trp Met
        850                  855                  860

GCT CCT GAG AGC ATC TTT GAC AAC CTC TAC ACC ACA CTG AGT GAT GTC       2762
```

```
                Ala Pro Glu Ser Ile Phe Asp Asn Leu Tyr Thr Thr Leu Ser Asp Val
                        865                 870                 875

TGG TCT TAT GGC ATT CTG CTC TGG GAG ATC TTT TCC CTT GGT GGC ACC                2810
Trp Ser Tyr Gly Ile Leu Leu Trp Glu Ile Phe Ser Leu Gly Gly Thr
        880                 885                 890

CCT TAC CCC GGC ATG ATG GTG GAT TCT ACT TTC TAC AAT AAG ATC AAG                2858
Pro Tyr Pro Gly Met Met Val Asp Ser Thr Phe Tyr Asn Lys Ile Lys
895                 900                 905                 910

AGT GGG TAC CGG ATG GCC AAG CCT GAC CAC GCT ACC AGT GAA GTC TAC                2906
Ser Gly Tyr Arg Met Ala Lys Pro Asp His Ala Thr Ser Glu Val Tyr
                915                 920                 925

GAG ATC ATG GTG AAA TGC TGG AAC AGT GAG CCG GAG AAG AGA CCC TCC                2954
Glu Ile Met Val Lys Cys Trp Asn Ser Glu Pro Glu Lys Arg Pro Ser
                930                 935                 940

TTT TAC CAC CTG AGT GAG ATT GTG GAG AAT CTG CTG CCT GGA CAA TAT                3002
Phe Tyr His Leu Ser Glu Ile Val Glu Asn Leu Leu Pro Gly Gln Tyr
                945                 950                 955

AAA AAG AGT TAT GAA AAA ATT CAC CTG GAC TTC CTG AAG AGT GAC CAT                3050
Lys Lys Ser Tyr Glu Lys Ile His Leu Asp Phe Leu Lys Ser Asp His
        960                 965                 970

CCT GCT GTG GCA CGC ATG CGT GTG GAC TCA GAC AAT GCA TAC ATT GGT                3098
Pro Ala Val Ala Arg Met Arg Val Asp Ser Asp Asn Ala Tyr Ile Gly
975                 980                 985                 990

GTC ACC TAC AAA AAC GAG GAA GAC AAG CTG AAG GAC TGG GAG GGT GGT                3146
Val Thr Tyr Lys Asn Glu Glu Asp Lys Leu Lys Asp Trp Glu Gly Gly
                995                 1000                1005

CTG GAT GAG CAG AGA CTG AGC GCT GAC AGT GGC TAC ATC ATT CCT CTG                3194
Leu Asp Glu Gln Arg Leu Ser Ala Asp Ser Gly Tyr Ile Ile Pro Leu
            1010                1015                1020

CCT GAC ATT GAC CCT GTC CCT GAG GAG GAG GAC CTG GGC AAG AGG AAC                3242
Pro Asp Ile Asp Pro Val Pro Glu Glu Glu Asp Leu Gly Lys Arg Asn
            1025                1030                1035

AGA CAC AGC TCG CAG ACC TCT GAA GAG AGT GCC ATT GAG ACG GGT TCC                3290
Arg His Ser Ser Gln Thr Ser Glu Glu Ser Ala Ile Glu Thr Gly Ser
            1040                1045                1050

AGC AGT TCC ACC TTC ATC AAG AGA GAG GAC GAG ACC ATT GAA GAC ATC                3338
Ser Ser Ser Thr Phe Ile Lys Arg Glu Asp Glu Thr Ile Glu Asp Ile
1055                1060                1065                1070

GAC ATG ATG GAC GAC ATC GGC ATA GAC TCT TCA GAC CTG GTG GAA GAC                3386
Asp Met Met Asp Asp Ile Gly Ile Asp Ser Ser Asp Leu Val Glu Asp
                1075                1080                1085

AGC TTC CTG TAA CTGGCGGATT CGAGGGGTTC CTTCCACTTC TGGGGCCACC                    3438
Ser Phe Leu  *
            1090

TCTGGATCCC GTTCAGAAAA CCACTTTATT GCAATGCGGA GGTTGAGAGG AGGACTTGGT              3498

TGATGTTTAA AGAGAAGTTC CCAGCCAAGG GCCTCGGGGA GCCTTTCTAA ATATGAATGA              3558

ATGGGATATT TTGAAATGAA CTTTGTCAGT GTTGCCTCTT GCAATGCCTC AGTAGCATCT              3618

CAGTGGTGTG TGAAGTTTGG AGATAGATGG ATAAGGGAAT AATAGGCCAC AGAAGGTGAA              3678

CTTTCTGCTT CAAGGACATT GGTGAGAGTC CAACAGACAC AATTTATACT GCGACAGAAC              3738

TTCAGCATTG TAATTATGTA AATAACTCTA ACCACGGCTG TGTTTAGATT GTATTAACTA              3798

TCTTCTTTGG ACTTCTGAAG AGACCACTCA ATCCATCCAT GTACTTCCCT CTTGAAACCT              3858

GATGTCAGCT GCTGTTGAAC TTTTTAAAGA AGTGCATGAA AAACCATTTT TGACCTTAAA              3918

AGGTACTGGT ACTATAGCAT TTTGCTATCT TTTTTAGTGT TAAAGAGATA AAGAATAATA              3978

ATTAACCAAC CTTGTTTAAT AGATTTGGGT CATTTAGAAG CCTGACAACT CATTTTCATA              4038
```

```
TTGTAATCTA TGTTTATAAT ACTACTACTG TTATCAGTAA TGCTAAATGT GTAATAATGT      4098

AACATGATTT CCCTCCACAC AAAGCACAAT TTAAAAACAA TCCTTACTAA GTAGGTGATG      4158

AGTTTGACAG TTTTTGACAT TTATATTAAA TAACATGTTT CTCTATAAAG TATGGTAATA      4218

GCTTTAGTGA ATTAAATTTA GTTGAGCATA GAGAACAAAG TAAAAGTAGT GTTGTCCAGG      4278

AAGTCAGAAT TTTTAACTGT ACTGAATAGG TTCCCCAATC CATCGTATTA AAAAACAATT      4338

AACTGCCCTC TGAAATAATG GGATTAGAAA CAAACAAAAC TCTTAAGTCC TAAAAGTTCT      4398

CAATGTAGAG GCATAAACCT GTGCTGAACA TAACTTCTCA TGTATATTAC CCAATGGAAA      4458

ATATAATGAT CAGCGCAAAA GACTGGATTT GCAGAAGTTT TTTTTTTTTT TCTTCTTGCC      4518

TGATGAAAGC TTTGGCGACC CCAATATATG TATTTTTTGA ATCTATGAAC CTGAAAAGGG      4578

TCACAAAGGA TGCCCAGACA TCAGCCTCCT TCTTTCACCC CTTACCCCAA AGAGAAAGAG      4638

TTTGAAACTC GAGACCATAA AGATATTCTT TAGTGGAGGC TGGAAGTGCA TTAGCCTGAT      4698

CCTCAGTTCT CAAATGTGTG TGGCAGCCAG GTAGACTAGT ACCTGGGTTT CCATCCTTGA      4758

GATTCTGAAG TATGAAGTCT GAGGGAAACC AGAGTCTGTA TTTTTCTAAA CTCCCTGGCT      4818

GTTCTGATCG GCCAGGTTTC GGAAACACTG ACTTAGGTTT CAGGAAGTTG CCATGGGAAA      4878

CAAATAATTT GAACTTTGGA ACAGGGTTCT TAAGTTGGTG CGTCCTTCGG ATGATAAATT      4938

TAGGAACCGA AGTCCAATCA CTGTAAATTA CGGTAGATCG ATCGTTAACG CTGGAATTAA      4998

ATTGAAAGGT CAGAATCGAC TCCGACTCTT TCGATTTCAA ACCAAAACTG TCCAAAAGGT      5058

TTTCATTTCT ACGATGAAGG GTGACATACC CCCTCTAACT TGAAAGGGGC AGAGGGCAGA      5118

AGAGCGGAGG GTGAGGTATG GGGCGGTTCC TTTCCGTACA TGTTTTTAAT ACGTTAAGTC      5178

ACAAGGTTCA GAGACACATT GGTCGAGTCA CAAAACCACC TTTTTTGTAA AATTCAAAAT      5238

GACTATTAAA CTCCAATCTA CCCTCCTACT TAACAGTGTA GATAGGTGTG ACAGTTTGTC      5298

CAACCACACC CAAGTAACCG TAAGAAACGT TATGACGAAT TAACGACTAT GGTATACTTA      5358

CTTTGTACCC GACACTAATG ACGTTAGTGA CACGATAGCC GTCTACTACG AAACCTTCTA      5418

CGTCTTCGTT ATTATTTCAT GAACTGATGG ATGACCACAT TAGAGTTACG TTCGGGGTTG      5478

AAAGAATAGG TTGAAAAAGT ATCATTCACG CTTCTGACTC GGTCTAACCG GTTAATTTTT      5538

CTTTTGGACT GATCCAAGAC ATCTCGGTTA ATCTGAACTT TATGCAAACA CAAAGATCTT      5598

AGTGTCGAGT TCGTAAGACA AATAGCGAGT GAGAGGGAAC ATGTCGGAAT AAAACAACCA      5658

CGAAACGTAA AACTATAACG ACACTCGGAA CGTACTGTAG TACTCCGGCC TACTTTGAAG      5718

AGTCAGGTCG TCAAAGGTCA GGATTGTTTA CGAGGGTGGA CTTAAACATA TACTGACGTA      5778

AACACCCACA CACACACAAA AGTCGTTTAA GGTCTAAACA AAGGAAAACC GGAGGACGTT      5838

TCAGAGGTCT TCTTTTAAAC GGTTAGAAAG GATGAAAGAT AAAAATACTA CTGTTAGTTT      5898

CGGCCGGACT CTTTGTGATA AACACTGAAA AATTTGCTAA TCACTACAGG AATTTTACAC      5958

CAGACGGTTA GACATGTTTT ACCAGGATAA AAACACTTCT CCCTGTATTC TATTTTACTA      6018

CAATATGTAG TTATACATAT ATACATAAAG ATATATCTGA ACCTCTTATG ACGGTTTTGT      6078

AAATACTGTT CGACATAGTG ACGGAAGCAA ATATAAAAAA ATTGCACTA TTAGGGGTGT      6138

CCGTGTAATT GACAACGTGA AAACTTACAG GTTTTAAATA TAAATCTTT ATTATTTTTC      6198

TTTCTATGAA TGTACAAGGG TTTTGTTACC ACACCACTTA CACACTCTTT TTGATTGAAC      6258

TATCCCAGAT GGTTATGTTT TACATAATGC TTACGGGGAC AAGTACAAAA ACAAAATTTT      6318

GCACATTTAC TTCTAGAAAT ATAAAGTTAT TTACTATATA TTAAATTTCC TTAAG           6373
```

(2) INFORMATION FOR SEQ ID NO: 2:

(i) SEQUENCE CHARACTERISTICS:
        (A) LENGTH: 1089 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Gly Thr Ser His Pro Ala Phe Leu Val Leu Gly Cys Leu Leu Thr
 1               5                  10                  15

Gly Leu Ser Leu Ile Leu Cys Gln Leu Ser Leu Pro Ser Ile Leu Pro
             20                  25                  30

Asn Glu Asn Glu Lys Val Val Gln Leu Asn Ser Ser Phe Ser Leu Arg
         35                  40                  45

Cys Phe Gly Glu Ser Glu Val Ser Trp Gln Tyr Pro Met Ser Glu Glu
     50                  55                  60

Glu Ser Ser Asp Val Glu Ile Arg Asn Glu Glu Asn Asn Ser Gly Leu
 65                  70                  75                  80

Phe Val Thr Val Leu Glu Val Ser Ser Ala Ser Ala Ala His Thr Gly
                 85                  90                  95

Leu Tyr Thr Cys Tyr Tyr Asn His Thr Gln Thr Glu Glu Asn Glu Leu
             100                 105                 110

Glu Gly Arg His Ile Tyr Ile Tyr Val Pro Asp Pro Asp Val Ala Phe
         115                 120                 125

Val Pro Leu Gly Met Thr Asp Tyr Leu Val Ile Val Glu Asp Asp Asp
     130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                 165                 170                 175

Gly Phe Asn Gly Thr Phe Thr Val Gly Pro Tyr Ile Cys Glu Ala Thr
             180                 185                 190

Val Lys Gly Lys Lys Phe Gln Thr Ile Pro Phe Asn Val Tyr Ala Leu
         195                 200                 205

Lys Ala Thr Ser Glu Leu Asp Leu Glu Met Glu Ala Leu Lys Thr Val
     210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                 245                 250                 255

Gly Ile Thr Met Leu Glu Glu Ile Lys Val Pro Ser Ile Lys Leu Val
             260                 265                 270

Tyr Thr Leu Thr Val Pro Glu Ala Thr Val Lys Asp Ser Gly Asp Tyr
         275                 280                 285

Glu Cys Ala Ala Arg Gln Ala Thr Arg Glu Val Lys Glu Met Lys Lys
     290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                 325                 330                 335

Val Glu Val Arg Ala Tyr Pro Pro Pro Arg Ile Ser Trp Leu Lys Asn
             340                 345                 350

Asn Leu Thr Leu Ile Glu Asn Leu Thr Glu Ile Thr Thr Asp Val Glu
         355                 360                 365
```

```
Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
    530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780
```

-continued

```
Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
            805                 810                 815

Arg Asp Leu Ala Ala Arg Asn Val Leu Leu Ala Gln Gly Lys Ile Val
        820                 825                 830

Lys Ile Cys Asp Phe Gly Leu Ala Arg Asp Ile Met His Asp Ser Asn
    835                 840                 845

Tyr Val Ser Lys Gly Ser Thr Phe Leu Pro Val Lys Trp Met Ala Pro
850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
            885                 890                 895

Pro Gly Met Met Val Asp Ser Thr Phe Tyr Asn Lys Ile Lys Ser Gly
        900                 905                 910

Tyr Arg Met Ala Lys Pro Asp His Ala Thr Ser Glu Val Tyr Glu Ile
    915                 920                 925

Met Val Lys Cys Trp Asn Ser Glu Pro Glu Lys Arg Pro Ser Phe Tyr
930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
            965                 970                 975

Val Ala Arg Met Arg Val Asp Ser Asp Asn Ala Tyr Ile Gly Val Thr
        980                 985                 990

Tyr Lys Asn Glu Glu Asp Lys Leu Lys Asp Trp Glu Gly Gly Leu Asp
    995                 1000                1005

Glu Gln Arg Leu Ser Ala Asp Ser Gly Tyr Ile Ile Pro Leu Pro Asp
1010                1015                1020

Ile Asp Pro Val Pro Glu Glu Glu Asp Leu Gly Lys Arg Asn Arg His
1025                1030                1035                1040

Ser Ser Gln Thr Ser Glu Glu Ser Ala Ile Glu Thr Gly Ser Ser Ser
            1045                1050                1055

Ser Thr Phe Ile Lys Arg Glu Asp Glu Thr Ile Glu Asp Ile Asp Met
        1060                1065                1070

Met Asp Asp Ile Gly Ile Asp Ser Ser Asp Leu Val Glu Asp Ser Phe
    1075                1080                1085

Leu
```

(2) INFORMATION FOR SEQ ID NO: 3:

(i) SEQUENCE CHARACTERISTICS:
        (A) LENGTH: 5427 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 187..3507

(xi) SEQUENCE DESCRIPTION: SEQ ID NO: 3:

```
TGTTCTCCTG AGCCTTCAGG AGCCTGCACC AGTCCTGCCT GTCCTTCTAC TCAGCTGTTA      60

CCCACTCTGG GACCAGCAGT CTTTCTGATA ACTGGGAGAG GGCAGTAAGG AGGACTTCCT     120
```

-continued

```
GGAGGGGGTG ACTGTCCAGA GCCTGGAACT GTGCCCACAC CAGAAGCCAT CAGCAGCAAG       180

GACACC ATG CGG CTT CCG GGT GCG ATG CCA GCT CTG GCC CTC AAA GGC         228
       Met Arg Leu Pro Gly Ala Met Pro Ala Leu Ala Leu Lys Gly
               1095                1100

GAG CTG CTG TTG CTG TCT CTC CTG TTA CTT CTG GAA CCA CAG ATC TCT         276
Glu Leu Leu Leu Leu Ser Leu Leu Leu Leu Leu Glu Pro Gln Ile Ser
1105                1110                1115                1120

CAG GGC CTG GTC GTC ACA CCC CCG GGG CCA GAG CTT GTC CTC AAT GTC         324
Gln Gly Leu Val Val Thr Pro Pro Gly Pro Glu Leu Val Leu Asn Val
                1125                1130                1135

TCC AGC ACC TTC GTT CTG ACC TGC TCG GGT TCA GCT CCG GTG GTG TGG         372
Ser Ser Thr Phe Val Leu Thr Cys Ser Gly Ser Ala Pro Val Val Trp
                1140                1145                1150

GAA CGG ATG TCC CAG GAG CCC CCA CAG GAA ATG GCC AAG GCC CAG GAT         420
Glu Arg Met Ser Gln Glu Pro Pro Gln Glu Met Ala Lys Ala Gln Asp
            1155                1160                1165

GGC ACC TTC TCC AGC GTG CTC ACA CTG ACC AAC CTC ACT GGG CTA GAC         468
Gly Thr Phe Ser Ser Val Leu Thr Leu Thr Asn Leu Thr Gly Leu Asp
        1170                1175                1180

ACG GGA GAA TAC TTT TGC ACC CAC AAT GAC TCC CGT GGA CTG GAG ACC         516
Thr Gly Glu Tyr Phe Cys Thr His Asn Asp Ser Arg Gly Leu Glu Thr
1185                1190                1195                1200

GAT GAG CGG AAA CGG CTC TAC ATC TTT GTG CCA GAT CCC ACC GTG GGC         564
Asp Glu Arg Lys Arg Leu Tyr Ile Phe Val Pro Asp Pro Thr Val Gly
                1205                1210                1215

TTC CTC CCT AAT GAT GCC GAG GAA CTA TTC ATC TTT CTC ACG GAA ATA         612
Phe Leu Pro Asn Asp Ala Glu Glu Leu Phe Ile Phe Leu Thr Glu Ile
                1220                1225                1230

ACT GAG ATC ACC ATT CCA TGC CGA GTA ACA GAC CCA CAG CTG GTG GTG         660
Thr Glu Ile Thr Ile Pro Cys Arg Val Thr Asp Pro Gln Leu Val Val
            1235                1240                1245

ACA CTG CAC GAG AAG AAA GGG GAC GTT GCA CTG CCT GTC CCC TAT GAT         708
Thr Leu His Glu Lys Lys Gly Asp Val Ala Leu Pro Val Pro Tyr Asp
        1250                1255                1260

CAC CAA CGT GGC TTT TCT GGT ATC TTT GAG GAC AGA AGC TAC ATC TGC         756
His Gln Arg Gly Phe Ser Gly Ile Phe Glu Asp Arg Ser Tyr Ile Cys
1265                1270                1275                1280

AAA ACC ACC ATT GGG GAC AGG GAG GTG GAT TCT GAT GCC TAC TAT GTC         804
Lys Thr Thr Ile Gly Asp Arg Glu Val Asp Ser Asp Ala Tyr Tyr Val
                1285                1290                1295

TAC AGA CTC CAG GTG TCA TCC ATC AAC GTC TCT GTG AAC GCA GTG CAG         852
Tyr Arg Leu Gln Val Ser Ser Ile Asn Val Ser Val Asn Ala Val Gln
                1300                1305                1310

ACT GTG GTC CGC CAG GGT GAG AAC ATC ACC CTC ATG TGC ATT GTG ATC         900
Thr Val Val Arg Gln Gly Glu Asn Ile Thr Leu Met Cys Ile Val Ile
            1315                1320                1325

GGG AAT GAT GTG GTC AAC TTC GAG TGG ACA TAC CCC CGC AAA GAA AGT         948
Gly Asn Asp Val Val Asn Phe Glu Trp Thr Tyr Pro Arg Lys Glu Ser
        1330                1335                1340

GGG CGG CTG GTG GAG CCG GTG ACT GAC TTC CTC TTG GAT ATG CCT TAC         996
Gly Arg Leu Val Glu Pro Val Thr Asp Phe Leu Leu Asp Met Pro Tyr
1345                1350                1355                1360

CAC ATC CGC TCC ATC CTG CAC ATC CCC AGT GCC GAG TTA GAA GAC TCG        1044
His Ile Arg Ser Ile Leu His Ile Pro Ser Ala Glu Leu Glu Asp Ser
                1365                1370                1375

GGG ACC TAC ACC TGC AAT GTG ACG GAG AGT GTG AAT GAC CAT CAG GAT        1092
Gly Thr Tyr Thr Cys Asn Val Thr Glu Ser Val Asn Asp His Gln Asp
                1380                1385                1390
```

-continued

| | | |
|---|---|---|
| GAA AAG GCC ATC AAC ATC ACC GTG GTT GAG AGC GGC TAC GTG CGG CTC<br>Glu Lys Ala Ile Asn Ile Thr Val Val Glu Ser Gly Tyr Val Arg Leu<br>     1395                       1400                     1405 | 1140 |
| CTG GGA GAG GTG GGC ACA CTA CAA TTT GCT GAG CTG CAT CGG AGC CGG<br>Leu Gly Glu Val Gly Thr Leu Gln Phe Ala Glu Leu His Arg Ser Arg<br>     1410                       1415                     1420 | 1188 |
| ACA CTG CAG GTA GTG TTC GAG GCC TAC CCA CCG CCC ACT GTC CTG TGG<br>Thr Leu Gln Val Val Phe Glu Ala Tyr Pro Pro Pro Thr Val Leu Trp<br>1425                       1430                     1435                     1440 | 1236 |
| TTC AAA GAC AAC CGC ACC CTG GGC GAC TCC AGC GCT GGC GAA ATC GCC<br>Phe Lys Asp Asn Arg Thr Leu Gly Asp Ser Ser Ala Gly Glu Ile Ala<br>                   1445                     1450                     1455 | 1284 |
| CTG TCC ACG CGC AAC GTG TCG GAG ACC CGG TAT GTG TCA GAG CTG ACA<br>Leu Ser Thr Arg Asn Val Ser Glu Thr Arg Tyr Val Ser Glu Leu Thr<br>     1460                       1465                     1470 | 1332 |
| CTG GTT CGC GTG AAG GTG GCA GAG GCT GGC CAC TAC ACC ATG CGG GCC<br>Leu Val Arg Val Lys Val Ala Glu Ala Gly His Tyr Thr Met Arg Ala<br>     1475                       1480                     1485 | 1380 |
| TTC CAT GAG GAT GCT GAG GTC CAG CTC TCC TTC CAG CTA CAG ATC AAT<br>Phe His Glu Asp Ala Glu Val Gln Leu Ser Phe Gln Leu Gln Ile Asn<br>     1490                       1495                     1500 | 1428 |
| GTC CCT GTC CGA GTG CTG GAG CTA AGT GAG AGC CAC CCT GAC AGT GGG<br>Val Pro Val Arg Val Leu Glu Leu Ser Glu Ser His Pro Asp Ser Gly<br>1505                       1510                     1515                     1520 | 1476 |
| GAA CAG ACA GTC CGC TGT CGT GGC CGG GGC ATG CCG CAG CCG AAC ATC<br>Glu Gln Thr Val Arg Cys Arg Gly Arg Gly Met Pro Gln Pro Asn Ile<br>                   1525                     1530                     1535 | 1524 |
| ATC TGG TCT GCC TGC AGA GAC CTC AAA AGG TGT CCA CGT GAG CTG CCG<br>Ile Trp Ser Ala Cys Arg Asp Leu Lys Arg Cys Pro Arg Glu Leu Pro<br>     1540                       1545                     1550 | 1572 |
| CCC ACG CTG CTG GGG AAC AGT TCC GAA GAG GAG AGC CAG CTG GAG ACT<br>Pro Thr Leu Leu Gly Asn Ser Ser Glu Glu Glu Ser Gln Leu Glu Thr<br>                   1555                     1560                     1565 | 1620 |
| AAC GTG ACG TAC TGG GAG GAG GAG CAG GAG TTT GAG GTG GTG AGC ACA<br>Asn Val Thr Tyr Trp Glu Glu Glu Gln Glu Phe Glu Val Val Ser Thr<br>     1570                       1575                     1580 | 1668 |
| CTG CGT CTG CAG CAC GTG GAT CGG CCA CTG TCG GTG CGC TGC ACG CTG<br>Leu Arg Leu Gln His Val Asp Arg Pro Leu Ser Val Arg Cys Thr Leu<br>1585                       1590                     1595                     1600 | 1716 |
| CGC AAC GCT GTG GGC CAG GAC ACG CAG GAG GTC ATC GTG GTG CCA CAC<br>Arg Asn Ala Val Gly Gln Asp Thr Gln Glu Val Ile Val Val Pro His<br>                   1605                     1610                     1615 | 1764 |
| TCC TTG CCC TTT AAG GTG GTG GTG ATC TCA GCC ATC CTG GCC CTG GTG<br>Ser Leu Pro Phe Lys Val Val Val Ile Ser Ala Ile Leu Ala Leu Val<br>                   1620                     1625                     1630 | 1812 |
| GTG CTC ACC ATC ATC TCC CTT ATC ATC CTC ATC ATG CTT TGG CAG AAG<br>Val Leu Thr Ile Ile Ser Leu Ile Ile Leu Ile Met Leu Trp Gln Lys<br>     1635                       1640                     1645 | 1860 |
| AAG CCA CGT TAC GAG ATC CGA TGG AAG GTG ATT GAG TCT GTG AGC TCT<br>Lys Pro Arg Tyr Glu Ile Arg Trp Lys Val Ile Glu Ser Val Ser Ser<br>     1650                       1655                     1660 | 1908 |
| GAC GGC CAT GAG TAC ATC TAC GTG GAC CCC ATG CAG CTG CCC TAT GAC<br>Asp Gly His Glu Tyr Ile Tyr Val Asp Pro Met Gln Leu Pro Tyr Asp<br>1665                       1670                     1675                     1680 | 1956 |
| TCC ACG TGG GAG CTG CCG CGG GAC CAG CTT GTG CTG GGA CGC ACC CTC<br>Ser Thr Trp Glu Leu Pro Arg Asp Gln Leu Val Leu Gly Arg Thr Leu<br>                   1685                     1690                     1695 | 2004 |
| GGC TCT GGG GCC TTT GGG CAG GTG GTG GAG GCC ACA GCT CAT GGT CTG<br>Gly Ser Gly Ala Phe Gly Gln Val Val Glu Ala Thr Ala His Gly Leu<br>     1700                       1705                     1710 | 2052 |

-continued

```
AGC CAT TCT CAG GCC ACG ATG AAA GTG GCC GTC AAG ATG CTT AAA TCC     2100
Ser His Ser Gln Ala Thr Met Lys Val Ala Val Lys Met Leu Lys Ser
        1715                1720                1725

ACA GCC CGC AGC AGT GAG AAG CAA GCC CTT ATG TCG GAG CTG AAG ATC     2148
Thr Ala Arg Ser Ser Glu Lys Gln Ala Leu Met Ser Glu Leu Lys Ile
        1730                1735                1740

ATG AGT CAC CTT GGG CCC CAC CTG AAC GTG GTC AAC CTG TTG GGG GCC     2196
Met Ser His Leu Gly Pro His Leu Asn Val Val Asn Leu Leu Gly Ala
1745                1750                1755                1760

TGC ACC AAA GGA GGA CCC ATC TAT ATC ATC ACT GAG TAC TGC CGC TAC     2244
Cys Thr Lys Gly Gly Pro Ile Tyr Ile Ile Thr Glu Tyr Cys Arg Tyr
                1765                1770                1775

GGA GAC CTG GTG GAC TAC CTG CAC CGC AAC AAA CAC ACC TTC CTG CAG     2292
Gly Asp Leu Val Asp Tyr Leu His Arg Asn Lys His Thr Phe Leu Gln
        1780                1785                1790

CAC CAC TCC GAC AAG CGC CGC CCG CCC AGC GCG GAG CTC TAC AGC AAT     2340
His His Ser Asp Lys Arg Arg Pro Pro Ser Ala Glu Leu Tyr Ser Asn
        1795                1800                1805

GCT CTG CCC GTT GGG CTC CCC CTG CCC AGC CAT GTG TCC TTG ACC GGG     2388
Ala Leu Pro Val Gly Leu Pro Leu Pro Ser His Val Ser Leu Thr Gly
        1810                1815                1820

GAG AGC GAC GGT GGC TAC ATG GAC ATG AGC AAG GAC GAG TCG GTG GAC     2436
Glu Ser Asp Gly Gly Tyr Met Asp Met Ser Lys Asp Glu Ser Val Asp
1825                1830                1835                1840

TAT GTG CCC ATG CTG GAC ATG AAA GGA GAC GTC AAA TAT GCA GAC ATC     2484
Tyr Val Pro Met Leu Asp Met Lys Gly Asp Val Lys Tyr Ala Asp Ile
                1845                1850                1855

GAG TCC TCC AAC TAC ATG GCC CCT TAC GAT AAC TAC GTT CCC TCT GCC     2532
Glu Ser Ser Asn Tyr Met Ala Pro Tyr Asp Asn Tyr Val Pro Ser Ala
        1860                1865                1870

CCT GAG AGG ACC TGC CGA GCA ACT TTG ATC AAC GAG TCT CCA GTG CTA     2580
Pro Glu Arg Thr Cys Arg Ala Thr Leu Ile Asn Glu Ser Pro Val Leu
        1875                1880                1885

AGC TAC ATG GAC CTC GTG GGC TTC AGC TAC CAG GTG GCC AAT GGC ATG     2628
Ser Tyr Met Asp Leu Val Gly Phe Ser Tyr Gln Val Ala Asn Gly Met
        1890                1895                1900

GAG TTT CTG GCC TCC AAG AAC TGC GTC CAC AGA GAC CTG GCG GCT AGG     2676
Glu Phe Leu Ala Ser Lys Asn Cys Val His Arg Asp Leu Ala Ala Arg
1905                1910                1915                1920

AAC GTG CTC ATC TGT GAA GGC AAG CTG GTC AAG ATC TGT GAC TTT GGC     2724
Asn Val Leu Ile Cys Glu Gly Lys Leu Val Lys Ile Cys Asp Phe Gly
                1925                1930                1935

CTG GCT CGA GAC ATC ATG CGG GAC TCG AAT TAC ATC TCC AAA GGC AGC     2772
Leu Ala Arg Asp Ile Met Arg Asp Ser Asn Tyr Ile Ser Lys Gly Ser
        1940                1945                1950

ACC TTT TTG CCT TTA AAG TGG ATG GCT CCG GAG AGC ATC TTC AAC AGC     2820
Thr Phe Leu Pro Leu Lys Trp Met Ala Pro Glu Ser Ile Phe Asn Ser
        1955                1960                1965

CTC TAC ACC ACC CTG AGC GAC GTG TGG TCC TTC GGG ATC CTG CTC TGG     2868
Leu Tyr Thr Thr Leu Ser Asp Val Trp Ser Phe Gly Ile Leu Leu Trp
        1970                1975                1980

GAG ATC TTC ACC TTG GGT GGC ACC CCT TAC CCA GAG CTG CCC ATG AAC     2916
Glu Ile Phe Thr Leu Gly Gly Thr Pro Tyr Pro Glu Leu Pro Met Asn
1985                1990                1995                2000

GAG CAG TTC TAC AAT GCC ATC AAA CGG GGT TAC CGC ATG GCC CAG CCT     2964
Glu Gln Phe Tyr Asn Ala Ile Lys Arg Gly Tyr Arg Met Ala Gln Pro
                2005                2010                2015

GCC CAT GCC TCC GAC GAG ATC TAT GAG ATC ATG CAG AAG TGC TGG GAA     3012
Ala His Ala Ser Asp Glu Ile Tyr Glu Ile Met Gln Lys Cys Trp Glu
```

-continued

```
                  2020                2025                2030
GAG AAG TTT GAG ATT CGG CCC CCC TTC TCC CAG CTG GTG CTG CTT CTC         3060
Glu Lys Phe Glu Ile Arg Pro Pro Phe Ser Gln Leu Val Leu Leu Leu
            2035                2040                2045

GAG AGA CTG TTG GGC GAA GGT TAC AAA AAG AAG TAC CAG CAG GTG GAT         3108
Glu Arg Leu Leu Gly Glu Gly Tyr Lys Lys Lys Tyr Gln Gln Val Asp
            2050                2055                2060

GAG GAG TTT CTG AGG AGT GAC CAC CCA GCC ATC CTT CGG TCC CAG GCC         3156
Glu Glu Phe Leu Arg Ser Asp His Pro Ala Ile Leu Arg Ser Gln Ala
2065                2070                2075                2080

CGC TTG CCT GGG TTC CAT GGC CTC CGA TCT CCC CTG GAC ACC AGC TCC         3204
Arg Leu Pro Gly Phe His Gly Leu Arg Ser Pro Leu Asp Thr Ser Ser
                2085                2090                2095

GTC CTC TAT ACT GCC GTG CAG CCC AAT GAG GGT GAC AAC GAC TAT ATC         3252
Val Leu Tyr Thr Ala Val Gln Pro Asn Glu Gly Asp Asn Asp Tyr Ile
            2100                2105                2110

ATC CCC CTG CCT GAC CCC AAA CCT GAG GTT GCT GAC GAG GGC CCA CTG         3300
Ile Pro Leu Pro Asp Pro Lys Pro Glu Val Ala Asp Glu Gly Pro Leu
            2115                2120                2125

GAG GGT TCC CCC AGC CTA GCC AGC TCC ACC CTG AAT GAA GTC AAC ACC         3348
Glu Gly Ser Pro Ser Leu Ala Ser Ser Thr Leu Asn Glu Val Asn Thr
            2130                2135                2140

TCC TCA ACC ATC TCC TGT GAC AGC CCC CTG GAG CCC CAG GAC GAA CCA         3396
Ser Ser Thr Ile Ser Cys Asp Ser Pro Leu Glu Pro Gln Asp Glu Pro
2145                2150                2155                2160

GAG CCA GAG CCC CAG CTT GAG CTC CAG GTG GAG CCG GAG CCG GAG CTG         3444
Glu Pro Glu Pro Gln Leu Glu Leu Gln Val Glu Pro Glu Pro Glu Leu
                2165                2170                2175

GAA CAG TTG CCG GAT TCG GGT TGC CCT GCG CCT CGG GCG GAA GCA GAG         3492
Glu Gln Leu Pro Asp Ser Gly Cys Pro Ala Pro Arg Ala Glu Ala Glu
            2180                2185                2190

GAT AGC TTC CTG TAG GGGGCTGGCC CCTACCCTGC CCTGCCTGAA GCTCCCCCGC         3547
Asp Ser Phe Leu *
            2195

TGCCAGCACC CAGCATCTCC TGGCCTGGCC TGGCCGGGCT TCCTGTCAGC CAGGCTGCCC       3607

TTATCAGCTG TCCCCTTCTG GAAGCTTTCT GCTCCTGACG TGTTGTGCCC CAAACCCTGG       3667

GGCTGGCTTA GGAGGCAAGA AAACTGCAGG GGCCGTGACC AGCCCTCTGC CTCCAGGGAG       3727

GCCAACTGAC TCTGAGCCAG GGTTCCCCCA GGGAACTCAG TTTTCCCATA TGTAAGATGG       3787

GAAAGTTAGG CTTGATGACC CAGAATCTAG GATTCTCTCC CTGGCTGACA GGTGGGGAGA       3847

CCGAATCCCT CCCTGGGAAG ATTCTTGGAG TTACTGAGGT GGTAAATTAA CTTTTTTCTG       3907

TTCAGCCAGC TACCCCTCAA GGAATCATAG CTCTCTCCTC GCACTTTTAT CCACCCAGGA       3967

GCTAGGGAAG AGACCCTAGC CTCCCTGGCT GCTGGCTGAG CTAGGGCCTA GCCTTGAGCA       4027

GTGTTGCCTC ATCCAGAAGA AAGCCAGTCT CCTCCCTATG ATGCCAGTCC CTGCGTTCCC       4087

TGGCCCGAGC TGGTCTGGGG CCATTAGGCA GCCTAATTAA TGCTGGAGGC TGAGCCAAGT       4147

ACAGGACACC CCCAGCCTGC AGCCCTTGCC CAGGGCACTT GGAGCACACG CAGCCATAGC       4207

AAGTGCCTGT GTCCCTGTCC TTCAGGCCCA TCAGTCCTGG GGCTTTTTCT TTATCACCCT       4267

CAGTCTTAAT CCATCCACCA GAGTCTAGAA GGCCAGACGG GCCCCGCATC TGTGATGAGA       4327

ATGTAAATGT GCCAGTGTGG AGTGGCCACG TGTGTGTGCC AGATATGGCC CTGGCTCTGC       4387

ATTGGACCTG CTATGAGGCT TTGGAGGAAT CCCTCACCCT CTCTGGGCCT CAGTTTCCCC       4447

TTCAAAAAAT GAATAAGTCG GACTTATTAA CTCTGAGTGC CTTGCCAGCA CTAACATTCT       4507

AGAGTATCCA GGTGGTTGCA CATTTGTCCA GATGAAGCAA GGCCATATAC CCTAAACTTC       4567
```

-continued

```
CATCCTGGGG GTCAGCTGGG CTCCTGGGAG ATTCCAGATC ACACATCACA CTCTGGGGAC       4627

TCAGGAACCA TGCCCCTTCC CCAGGCCCCC AGCAAGTCTC AAGAACACAG CTGCACAGGC       4687

CTTGACTTAG AGTGACAGCC GGTGTCCTGG AAAGCCCCCA GCAGCTGCCC CAGGGACATG       4747

GGAAGACCAC GGGACCTCTT TCACTACCCA CGATGACCTC CGGGGGTATC CTGGGCAAAA       4807

GGGACAAAGA GGGCAAATGA GATCACCTCC TGCAGCCCAC CACTCCAGCA CCTGTGCCGA       4867

GGTCTGCGTC GAAGACAGAA TGGACAGTGA GGACAGTTAT GTCTTGTAAA AGACAAGAAG       4927

CTTCAGATGG GTACCCCAAG AAGGATGTGA GAGGTGGGCG CTTTGGAGGT TTGCCCCTCA       4987

CCCACCAGCT GCCCCATCCC TGAGGCAGCG CTCCATGGGG GTATGGTTTT GTCACTGCCC       5047

AGACCTAGCA GTGACATCTC ATTGTCCCCA GCCCAGTGGG CATTGGAGGT GCCAGGGGAG       5107

TCAGGGTTGT AGCCAAGACG CCCCCGCACG GGGAGGGTTG GGAAGGGGGT GCAGGAAGCT       5167

CAACCCCTCT GGGCACCAAC CCTGCATTGC AGGTTGGCAC CTTACTTCCC TGGGATCCCA       5227

GAGTTGGTCC AAGGAGGGAG AGTGGGTTCT CAATACGGTA CCAAAGATAT AATCACCTAG       5287

GTTTACAAAT ATTTTTAGGA CTCACGTTAA CTCACATTTA TACAGCAGAA ATGCTATTTT       5347

GTATGCTGTT AAGTTTTTCT ATCTGTGTAC TTTTTTTTAA GGGAAAGATT TTAATATTAA       5407

ACCTGGTGCT TCTCACTCAC                                                   5427
```

(2) INFORMATION FOR SEQ ID NO: 4:

(i) SEQUENCE CHARACTERISTICS:
        (A) LENGTH: 1106 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Arg Leu Pro Gly Ala Met Pro Ala Leu Ala Leu Lys Gly Glu Leu
 1               5                  10                  15

Leu Leu Leu Ser Leu Leu Leu Leu Glu Pro Gln Ile Ser Gln Gly
                20                  25                  30

Leu Val Val Thr Pro Pro Gly Pro Glu Leu Val Leu Asn Val Ser Ser
            35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190
```

-continued

```
Thr Ile Gly Asp Arg Glu Val Asp Ser Asp Ala Tyr Tyr Val Tyr Arg
    195                 200                 205

Leu Gln Val Ser Ser Ile Asn Val Ser Val Asn Ala Val Gln Thr Val
    210                 215                 220

Val Arg Gln Gly Glu Asn Ile Thr Leu Met Cys Ile Val Ile Gly Asn
225                 230                 235                 240

Asp Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
        355                 360                 365

Thr Arg Asn Val Ser Glu Thr Arg Tyr Val Ser Glu Leu Thr Leu Val
    370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
        435                 440                 445

Ser Ala Cys Arg Asp Leu Lys Arg Cys Pro Arg Glu Leu Pro Pro Thr
    450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
        515                 520                 525

Pro Phe Lys Val Val Ile Ser Ala Ile Leu Ala Leu Val Val Leu
    530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
                565                 570                 575

His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
        595                 600                 605

Gly Ala Phe Gly Gln Val Val Glu Ala Thr Ala His Gly Leu Ser His
```

```
                610                 615                 620
Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
                660                 665                 670

Lys Gly Gly Pro Ile Tyr Ile Ile Thr Glu Tyr Cys Arg Tyr Gly Asp
                675                 680                 685

Leu Val Asp Tyr Leu His Arg Asn Lys His Thr Phe Leu Gln His His
690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
                740                 745                 750

Pro Met Leu Asp Met Lys Gly Asp Val Lys Tyr Ala Asp Ile Glu Ser
                755                 760                 765

Ser Asn Tyr Met Ala Pro Tyr Asp Asn Tyr Val Pro Ser Ala Pro Glu
770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                805                 810                 815

Leu Ala Ser Lys Asn Cys Val His Arg Asp Leu Ala Ala Arg Asn Val
                820                 825                 830

Leu Ile Cys Glu Gly Lys Leu Val Lys Ile Cys Asp Phe Gly Leu Ala
                835                 840                 845

Arg Asp Ile Met Arg Asp Ser Asn Tyr Ile Ser Lys Gly Ser Thr Phe
850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                885                 890                 895

Phe Thr Leu Gly Gly Thr Pro Tyr Pro Glu Leu Pro Met Asn Glu Gln
                900                 905                 910

Phe Tyr Asn Ala Ile Lys Arg Gly Tyr Arg Met Ala Gln Pro Ala His
                915                 920                 925

Ala Ser Asp Glu Ile Tyr Glu Ile Met Gln Lys Cys Trp Glu Glu Lys
930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
                965                 970                 975

Phe Leu Arg Ser Asp His Pro Ala Ile Leu Arg Ser Gln Ala Arg Leu
                980                 985                 990

Pro Gly Phe His Gly Leu Arg Ser Pro Leu Asp Thr Ser Ser Val Leu
                995                 1000                1005

Tyr Thr Ala Val Gln Pro Asn Glu Gly Asp Asn Asp Tyr Ile Ile Pro
     1010                1015                1020

Leu Pro Asp Pro Lys Pro Glu Val Ala Asp Glu Gly Pro Leu Glu Gly
1025                1030                1035                1040
```

```
Ser Pro Ser Leu Ala Ser Ser Thr Leu Asn Glu Val Asn Thr Ser Ser
            1045                1050                1055

Thr Ile Ser Cys Asp Ser Pro Leu Glu Pro Gln Asp Glu Pro Glu Pro
            1060                1065                1070

Glu Pro Gln Leu Glu Leu Gln Val Glu Pro Glu Pro Glu Leu Glu Gln
            1075                1080                1085

Leu Pro Asp Ser Gly Cys Pro Ala Pro Arg Ala Glu Ala Glu Asp Ser
            1090                1095                1100

Phe Leu
1105

(2) INFORMATION FOR SEQ ID NO: 5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "Peptide Y719"

(xi) SEQUENCE DESCRIPTION: SEQ ID NO: 5:

Gly Gly Tyr Met Asp Met Ser Lys Asp Glu Ser Ile Asp Tyr Val Pro
1               5                   10                  15

Met Leu Asp Met
            20

(2) INFORMATION FOR SEQ ID NO: 6:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "Peptide Y719P.  Contains a
            phosphate group at position 14."

(xi) SEQUENCE DESCRIPTION: SEQ ID NO: 6:

Gly Gly Tyr Met Asp Met Ser Lys Asp Glu Ser Ile Asp Tyr Val Pro
1               5                   10                  15

Met Leu Asp Met
            20

(2) INFORMATION FOR SEQ ID NO: 7:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..20
```

(D) OTHER INFORMATION: /note= "Peptide Y708P. Contains a
    phosphate group at position 3."

(xi) SEQUENCE DESCRIPTION: SEQ ID NO: 7:

Gly Gly Tyr Met Asp Met Ser Lys Asp Glu Ser Ile Asp Tyr Val Pro
1               5                   10                  15
Met Leu Asp Met
            20

(2) INFORMATION FOR SEQ ID NO: 8:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..17
        (D) OTHER INFORMATION: /note= "Peptide Y719P short.
            Contains a phosphate group at position 11."

(xi) SEQUENCE DESCRIPTION: SEQ ID NO: 8:

Met Asp Met Ser Lys Asp Glu Ser Ile Asp Tyr Val Pro Met Leu Asp
1               5                   10                  15
Met (2) INFORMATION FOR SEQ ID NO: 9:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..13
        (D) OTHER INFORMATION: /note= "Peptide Y708P short.
            Contains a phosphate group at position 3."

(xi) SEQUENCE DESCRIPTION: SEQ ID NO: 9:

Gly Gly Tyr Met Asp Met Ser Lys Asp Glu Ser Ile Asp
1               5                   10

(2) INFORMATION FOR SEQ ID NO: 10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "Peptide Y708P/F719.
            Contains a phosphate group at position 3."

(xi) SEQUENCE DESCRIPTION: SEQ ID NO: 10:

Gly Gly Tyr Met Asp Met Ser Lys Asp Glu Ser Ile Asp Phe Val Pro
1               5                   10                  15

Met Leu Asp Met
        20

(2) INFORMATION FOR SEQ ID NO: 11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "Peptide Y708/Y719P.
            Contains a phosphate group at position 14."

(xi) SEQUENCE DESCRIPTION: SEQ ID NO: 11:

Gly Gly Phe Met Asp Met Ser Lys Asp Glu Ser Ile Asp Tyr Val Pro
1               5                   10                  15

Met Leu Asp Met
        20

(2) INFORMATION FOR SEQ ID NO: 12:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "Peptide Y708P/Y719P.
            Contains phosphate group at positions 3 & 14"

(xi) SEQUENCE DESCRIPTION: SEQ ID NO: 12:

Gly Gly Tyr Met Asp Met Ser Lys Asp Glu Ser Ile Asp Tyr Val Pro
1               5                   10                  15

Met Leu Asp Met
        20

(2) INFORMATION FOR SEQ ID NO: 13:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "Peptide Y719P scrambled.
            Contains a phosphate group at position 15."

(xi) SEQUENCE DESCRIPTION: SEQ ID NO: 13:

Met Met Asp Ile Lys Val Pro Met Asp Glu Tyr Met Ser Asp Tyr Ser
1               5                   10                  15

Asp Leu Gly Gly
        20

```
(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: /note= "N is A, C, G, or T"

(xi) SEQUENCE DESCRIPTION: SEQ ID NO: 14:

GTTSCGNGCN GCCAGNTCSC GNTG                                              24
```

HUMAN PLATELET-DERIVED GROWTH FACTOR RECEPTORS

CROSS-REFERENCES TO RELATED APPLICATIONS

This application is a continuation of U.S. patent application Ser. No. 08/461,917, filed Jun. 5, 1995 and now issued U.S. Pat. No. 6,372,438; which is a continuation of U.S. patent application Ser. No. 08/226,243, filed Apr. 11, 1994 and now abandoned; which is a continuation of U.S. patent application Ser. No. 07/650,794, filed Jan. 31, 1991 and now abandoned; which is a continuation-in-part of U.S. patent application Ser. No. 07/309,322, filed Feb. 10, 1989 and now abandoned; which is a continuation-in-part of U.S. patent application Ser. No. 07/151,414, filed Feb. 2, 1988 and now abandoned; the disclosures of which are incorporated herein by reference.

FIELD OF THE INVENTION

The present invention relates to the development of diagnostic and therapeutic agents and, in particular, to compositions based on platelet-derived growth factor receptors.

BACKGROUND OF THE INVENTION

Platelet-derived growth factor (PDGF) is a major mitogen for cells of mesenchymal origin. The protein mitogen is usually a 32 kDa protein heterodimer usually composed of two polypeptide chains, A and B, linked by disulfide bonds. In addition to the PDGF AB heterodimer, two homodimeric forms of PDGF, denoted AA and BB, have been identified.

The first event in PDGF-mediated mitogenesis is the binding of PDGF to its receptor at the cell membrane. This interaction triggers a diversity of early cellular responses including activation of receptor tyrosine kinase, increased phosphatidylinositol turnover, enhanced expression of a group of genes, activation of phospholipase A2, changes in cell shape, an increase in cellular calcium concentration, changes in intracellular pH, and internalization and degradation of bound PDGF. These changes are followed by an increase in the rate of proliferation of the target receptor containing cells.

The ability of a polypeptide to stimulate growth of a particular cell type in vitro does not prove that it serves the same function in vivo, but the roles of many growth factors on cells are being studied to determine the roles that the factors play in the whole organism. In vitro, platelet-derived growth factor is a major polypeptide mitogen in serum for cells of mesenchymal origin such as fibroblasts, smooth muscle cells, and glial cells. In vivo, PDGF does not circulate freely in blood, but is stored in the a granules of circulating blood platelets. During blood clotting and platelet adhesion, the granules are released, often at sites of injured blood vessels, thus implicating PDGF in the repair of blood vessels. PDGF may stimulate migration of arterial smooth muscle cells from the medial to the intimal layer of the artery where the muscle cells may proliferate. This is likely to be an early response to injury.

PDGF is being studied to determine how cell proliferation is controlled in the body. The growth factor has been implicated in wound healing, in atherosclerosis, in myeloproliferative disease, and in stimulating genes associated with cancerous transformation of cells, particularly c-myc and c-fos. Therefore, PDGF agonists may be useful in promoting wound healing. PDGF antagonists may also be useful in preventing atherosclerosis, in retarding blood vessel narrowing that occurs after cardiovascular intervention and in controlling cancerous proliferation.

The interaction of PDGF with cells is mediated, in part, by a receptor for the mitogen. The PDGF receptor is therefore a very important component in mitogenic stimulation by the growth factor. However, the inability to characterize the direct interaction between the PDGF and its receptor and between the PDGF receptor and intracellular components has hampered the development of reagents needed in the diagnosis or treatment of physiological conditions or disorders characterized by abnormal or undesired PDGF responses. For these reasons, a dramatic need exists to characterize the structural and physiological properties of PDGF receptors.

SUMMARY OF THE INVENTION

In accordance with the present invention, DNA sequences encoding human platelet-derived growth factor receptor (hPDGF-R) polypeptides have been isolated and sequenced. In one embodiment, expression constructs are provided comprising one or more sequences that encode PDGF-receptor proteins that can be secreted or associated with the membrane of a mammalian cell. The membrane associated receptor should be functionally similar to or equivalent to a wild-type receptor thereby conferring a PDGF sensitive mitogenic response on cells lacking the receptor. The construct can be used, inter alia, for producing large amounts of the PDGF-receptor or fragments, for enhancing PDGF response of cells, for determining the regions of the receptor polypeptides involved in transducing the mitogenic signal in response to PDGF binding, for providing mutated analogs of the receptor, for evaluating drugs for their physiologic activity, and for probing the integrity of sequences nearby the chromosomal loci of the receptor genes. In particular, various soluble fragments of the receptor are provided, many possessing various properties of cell associated hPDGF-R proteins. Novel methods utilizing these constructs are also provided.

The present invention provides a purified and isolated recombinant nucleic acid of less than about 50 kbp comprising at least about 24 contiguous nucleotides which encode a human platelet-derived growth factor receptor (hPDGF-R) polypeptide segment. Preferably the segment is a soluble polypeptide. In particular embodiments, the segment consists essentially of a full length extracellular region of a B type or an A type hPDGF receptor, e.g., a sequence of a polypeptide in Table 2 or Table 3. In other embodiments, the nucleic acid encodes a segment with a phosphorylation site.

Usually, the encoded segment is less than about 300 amino acids, and will preferably be capable of binding to PDGF, be a substrate for phosphorylation, or be capable of binding to a PI3 kinase. In other embodiments, the encoded segment lacks a substantially complete intracellular region.

The invention also embraces a cell transformed with the described nucleic acids, typically where the cell is a mammalian cell. In particular embodiments, the cell further contains a glycosylation enzyme originating from a non-fungal species.

Expression vectors are also provided, and in certain embodiments, the nucleic acid nucleotides encoding the segment are operably linked to a promoter. Recombinant nucleic acids are provided which further encode a heterologous polypeptide which is fused to the hPDGF-R segment.

As another aspect of the invention, methods are provided for evaluating the ability of a compound to function as a hPDGF-R agonist or antagonist, utilizing the step of comparing the amount of a PDGF-induced response from a control cell with that in a cell transformed with a hPDGF-R peptide fragment encoding nucleic acid. In various embodiments, the PDGF-induced response is compared by measuring synthesis of DNA in the cells. After contacting the cells with cell with PDGF.

Polypeptide embodiments include a substantially pure hPDGF-R polypeptide fragment of at least about twenty amino acids having platelet-derived growth factor (PDGF) binding activity or tyrosine kinase activity. Typically, the polypeptide fragment will be soluble.

In other embodiments, hPDGF-R fragments are provided having hPDGF-R binding activity consisting essentially of amino acids beginning at about 1 and ending at about 499 of a type B hPDGF-R, e.g., derived from Table 2, or consisting essentially of amino acids beginning about 1 and ending at about 501 of a type A hPDGF-R, e.g., derived from Table 3. The invention embraces compositions having an unglycosylated hPDGF-R fragment, preferably where the fragment is substantially pure. In other embodiments, the hPDGF-R fragment exhibits a glycosylation pattern which is non-fungal and non-human. Particularly useful compositions have a hPDGF-R polypeptide fragment which is essentially the extracellular region of a type B or a type A hPDGF-R, e.g., derived from sequences of Table 2 or Table 3. An additional embodiment is a composition comprising a combination of: (a) a recombinant nucleic acid encoding a human platelet-derived growth factor receptor polypeptide (hPDGF-R) fragment; and (b) a non-fungal glycosylation enzyme capable of glycosylating said fragment when expressed.

The present invention provides various methods for introducing a hPDGF-R activity to a cell, comprising the step of introducing a hPDGF-R protein fragment of at least about five hundred daltons to a cell. A method for assaying the presence of a ligand for a PDGF receptor in a sample is also provided, comprising the steps of: (a) combining the sample with a hPDGF receptor ligand binding site; and (b) detecting binding between the ligand and the hPDGF receptor ligand binding site.

With respect to the intracellular region of the PDGF receptors, the present invention provides an isolated polypeptide of less than about 200 amino acids comprising a receptor kinase insert region. In various embodiments, the polypeptide has a phosphorylated amino acid residue, e.g., phosphotyrosine. Usually, the polypeptide has a sequence substantially homologous to a kinase insert segment of a PDGF receptor, e.g., a sequence from Table 2 or Table 3. The invention also provides a composition with the polypeptide and a pharmaceutically acceptable carrier.

Various methods are provided by the invention, including methods for modulating the biological activity of a first protein which binds to a phosphorylated region of a second protein, the method including a step of adding to the first protein a peptide analogue of the phosphorylated region, where the analogue is capable of inhibiting the binding of the first protein to the second protein. Other methods are provided for selecting a molecule capable of inhibiting binding of a protein which binds to a target phosphorylated polypeptide. This method has steps of contacting the protein with the target phosphorylated polypeptide in the presence of the molecule in a first analysis; contacting the protein with the target phosphorylated polypeptide in the absence of the molecule in a second analysis; and comparing these analyses to determine the effect of the molecule on the binding. In particular embodiments, these contacting steps are performed in succession.

Other methods for modulating a PI3 kinase activity as provided, comprising the step of adding a phosphorylated PDGF receptor kinase insert region polypeptide to the PI3 kinase, thereby allowing binding between the polypeptide and the PI3 kinase.

The present invention provides methods for purifying, from a sample, a protein capable of binding to a PDGF receptor kinase insert segment, comprising the step of contacting the sample with an analogue of a phosphorylated polypeptide substantially homologous to a PDGF receptor kinase insert region polypeptide, thereby allowing the protein to bind specifically to the phosphorylated polypeptide.

Methods of isolating a nucleic acid encoding a protein capable of binding to a PDGF receptor are provided, comprising the steps of combining a labeled and phosphorylated PDGF receptor kinase insert region polypeptide with cells expressing various proteins, thereby labeling those cells which express the nucleic acid to produce a protein which binds the phosphorylated polypeptide; and isolating those cells which have been labeled. This method is particularly useful to isolate nucleic acids encoding PI3 kinase or c-fms.

BRIEF DESCRIPTION OF THE FIGURES

FIG. 1 illustrates the association of 85 kD/PI3 kinase with the type B PDGF receptor. The association of phosphoprotein with the PDGF receptor (a and b) and phosphatidylinositol 3' kinase (PI3 kinase) activity (c and d) were studied in intact cells (a and c) and in vitro (b and d). In the intact cell experiments PDGF-stimulated (+) or control cells (−) were solubilized and the receptor was immunoprecipitated using anti-receptor antibodies. The receptor-associated phosphoproteins were detected by incubating the receptor-associated protein complex with $MnCl_2$ and $\gamma^{32}P$-ATP followed by autoradiography of an SDS polyacrylamide gel. The PDGF-stimulated receptor associated with 85 kD and 110 kD phosphoproteins and PI3 kinase activity, but the unstimulated receptor was not. Equivalent amounts of receptor were immunoprecipitated from the lysates from stimulated and unstimulated cells. In vitro associations were performed by incubating the baculovirus-expressed receptor with lysates from PDGF-stimulated (+) or unstimulated (−) cells. Receptor-associated phosphoproteins (b) and PI3 kinase activity (d) were detected. The position of the 85 kD protein is indicated by the arrows.

FIG. 2 illustrates the association of 85 kD protein and PI3 kinase activity with the wild type and kinase insert deletion mutant receptor in vitro. Lysates from unstimulated 3T3 cells were mixed with immunoprecipitated wild type PDGF type B receptor or kinase insert deletion mutant receptor that were prepared using a baculovirus expression system. The immunoprecipitates containing receptor-associated proteins were washed extensively. In vitro protein kinase assays (panel a) or PI3 kinase activity assays (panel b) were performed on the proteins. The first lane of panel (a) shows the in vitro protein kinase assay of the baculovirous-expressed receptor that was not mixed with cell lysate. The top two bands of the second and third lanes of panel (a) are from the baculovirus-expressed receptor (second lane) or the mutated receptor (third lane) and their respective precursors. The arrow indicates the 85 kD protein.

FIG. 4 illustrates the use of peptides to block the association of the 85 kD phosphoprotein and PI3 kinase activity with the receptor. The peptides listed in Table AI were preincubated with unstimulated 3T3 cell lysates prior to incubation with immunoprecipitated receptor. The detection of the receptor-associated phosphoproteins (panel a) and the receptor-associated PI3 kinase activity (panel b) were performed as in FIGS. 1 and 2. The 85 kD protein is indicated by the arrow.

DETAILED DESCRIPTION OF THE PREFERRED EMBODIMENTS

Figure 3:
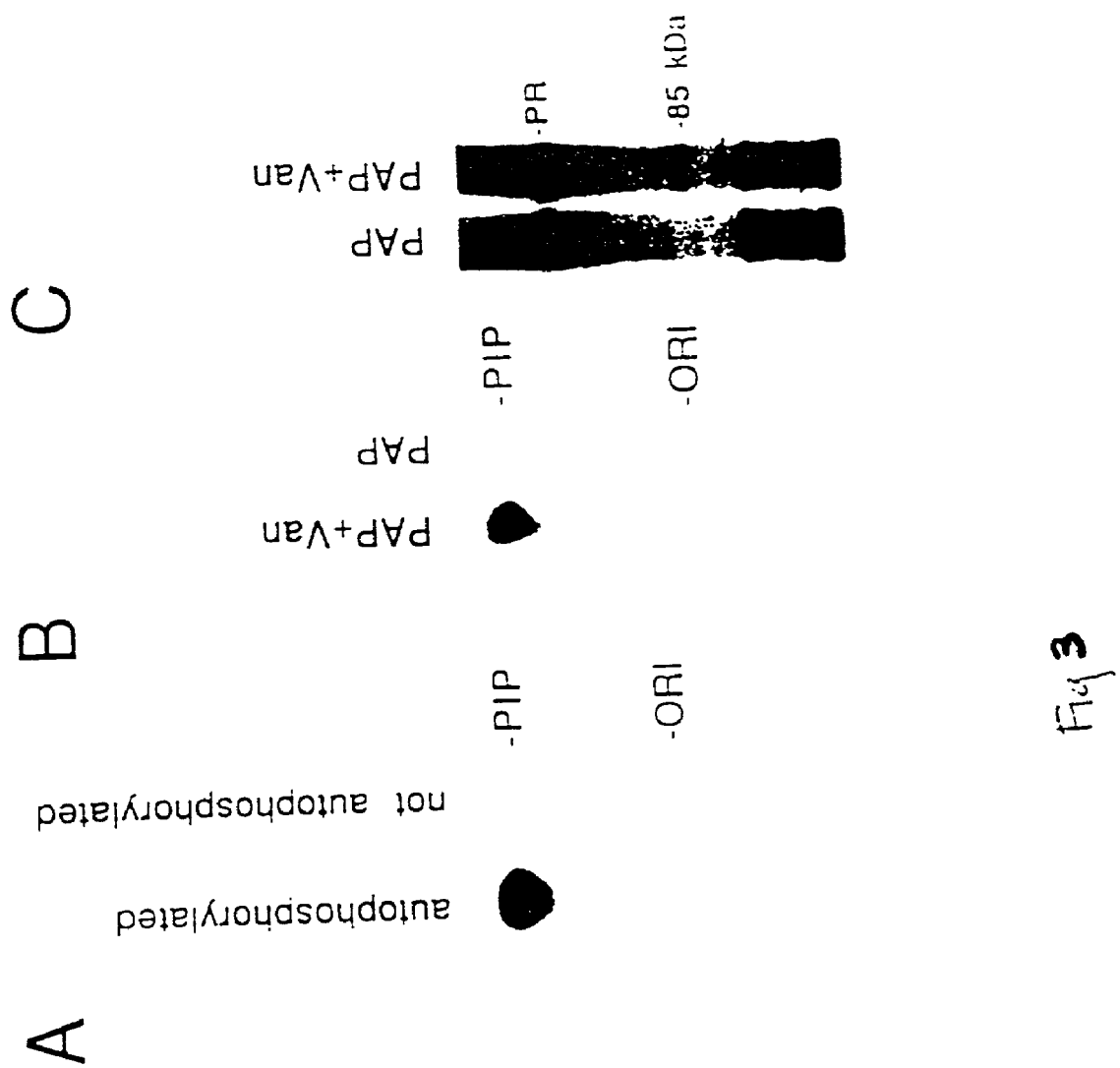
FIG. 3 illustrates the need for requirement of receptor autophosphorylation for association with PI3 kinase activity and 85 kD protein. PDGF receptors were immunoprecipitated from Sf9 cells infected with the wild type PDGF receptor recombinant baculovirus. Immunoprecipitates containing phosphorylated receptor were incubated with solubilized 3T3 cell lysates. PI3 kinase assays (a and b) and in vitro kinase assays (c) were performed. (a) Association of PI3 kinase activity with phosphorylated PDGF receptors were incubated with potato acid phosphatase (PAP) or PAP plus orthovanadate.

Human platelet derived growth factor receptor (hPDGF-R) compositions are provided by the present invention. These compositions will be full length natural forms, fragments of the natural forms, fusion proteins with those fragments, modified forms of each, and multi-protein complexes comprising them. In particular, soluble polypeptides exhibiting hPDGF-R functions are made available, both extracellular and intracellular region fragments.

Methods for producing protein compositions based upon hPDGF receptors are provided. Nucleic acid constructs which encode the various hPDGF-R protein compositions are also disclosed. The nucleic acid constructs will be useful to transfect cells, providing an efficient and economical means to produce commercially useful quantities of the protein compositions. These cells, and others containing hPDGF receptors, will also be useful in diagnosis or for study of mechanisms of PDGF mitogenic action. They will be used to evaluate new drugs which affect signal transduction of PDGF ligand binding, and in treatment of diseases associated with hPDGF receptors. The constructs can be used to transfect cells, providing membrane-bound receptors that are functionally equivalent to wild-type receptors, and conferring a PDGF-sensitive mitogenic response on cells lacking receptors. The transfected cells can be used as a model for studying the PDGF-induced response of cells, determining the regions involved in transducing the signal in response to PDGF ligand binding, and evaluating drugs for their physiologic activities. Encoded receptors or their binding regions also find use in evaluating PDGF analogues.

The receptor fragments and their analogues will find use in determining regions of the receptor polypeptides which are involved in signal transduction in response to PDGF binding. In particular, the ability to test various combinations of structural features, e.g., ligand binding determinants, will allow dissection of receptor features to determine the importance to ligand binding affinity, ligand specificity, and physiological responses.

The hPDGF-R proteins will also find use in producing antibody reagents. These reagents should be capable of interfering with, or simulating, particular molecular interactions of the receptor polypeptides.

Soluble proteins possessing PDGF binding capacity will be useful in blocking PDGF action, as reagents for the quantitation of PDGF in diagnostic samples, for soluble testing of binding interactions between modified determinants for ligand binding and natural, modified, or derivatized ligands, and for screening for monoclonal antibodies against hPDGF-R polypeptides. They will also find therapeutic uses.

The DNA sequences will also find use as probes to detect genetic abnormalities, e.g., deletions or rearrangements in the region of chromosome 5 where a number of growth-control related genes are clustered, in the region of chromosome 4 near the c-kit oncogenes, or to detect other genes encoding tyrosine kinases or homologous genes.

Certain regions of the cytoplasmic region of the PDGF receptor, among them the kinase insert (KI) region, allow the PDGF receptor to interact with, e.g., bind with, other cellular proteins. Peptides substantially homologous to these regions, as well as organic analogue molecules, will find use in inhibiting the interaction between the PDGF receptor and other proteins, in identifying, screening for, and purifying proteins with which the PDGF receptor interacts, and in cloning genes encoding these proteins. These homologous peptides will also find use in medical diagnosis and in drug therapies, e.g., affecting PDGF receptor activities and receptor interactions with other proteins.

Moreover, the understanding of the role of phosphorylated residues to protein-protein interactions is applicable to other receptors and phosphorylated proteins. The phosphorylation of specific amino acids in particular polypeptide segments or substantially homologous segments, e.g., phosphorylation sites, has special biological significance. Identification of the phosphorylation sites and regions of protein interactions are important in preparing reagents useful in inhibiting such interactions, leading to a modulation of the function of such proteins. The peptide analogues will also be useful in identifying and purifying proteins which interact with phosphorylated residues and in isolating and cloning genes encoding these proteins.

OUTLINE

I. General Description
   A. PDGF-R
      1. structural features
         a. extracellular region
            i. signal sequence
            ii. Ig domains
         b. transmembrane segment
         c. intracellular region
            i. tyrosine kinase
            ii. insert
      2. function
         a. bind PDGF
         b. bind to PDGF-R peptide
         c. tyrosine kinase activity
   B. Physiological Functions
      1. cellular
      2. tissue differentiation
      3. organismal
II. Polypeptides
   A. Soluble Forms
   B. Truncated Forms
   C. Fusion Proteins
   D. Genetic Variants (site-directed mutagenized)
   E. Compositions Comprising Proteins
III. Nucleic Acids
   A. Isolated Nucleic Acids
   B. Recombinant Nucleic Acids
   C. Compositions Comprising Nucleic Acids
IV. Methods for Making PDGF-R
   A. Protein Purification
      1. affinity with derivatized PDGF
      2. various ligands, same receptor
   B. Expression of Nucleic Acids
V. Antibodies
VI. Methods for Use
   A. Diagnostic
   B. Therapeutic I. General Description The isolated full-length human platelet-derived growth factor (hPDGF) receptor mRNA encodes a single hydrophobic polypeptide segment similar to a membrane-spanning segment (designated the transmembrane segment). The segments of a PDGF-R amino proximal to the transmembrane segment make up the extracellular region, while the segments carboxy proximal to the transmembrane segment are designated the intracellular region. From the amino terminus, the extracellular region has an $NH_2$-terminal hydrophobic putative signal sequence, an immunoglobulin-like domain (designated IgI), and second, third, fourth, and fifth immunoglobulin-like domains (designated IgII, IgIII, IgIV, and IgV, respectively). Although various structural features are identified in the external region of the hPDGF-R, the most important functional property which defines the region is the binding to the receptor ligands, e.g., members of the PDGF family and analogues thereof.

The intracellular region is characterized, in part, by the presence of a split tyrosine kinase structural domain. In the human type B receptor polypeptide, this domain is about 244 residues long and has an insert of about 104 amino acids. See Table 2. In the human type A receptor polypeptide, the tyrosine kinase domain is also about 244 residues long with a kinase insert of about 103 amino acids. See Table 3. Functionally, this domain is defined, in part, by its tyrosine kinase activity, typically modulated by ligand binding to the extracellular region, and appears to function in a dimer state. The substrate for phosphorylation includes various tyrosine residues on the accompanying receptor polypeptide chain, and other proteins which associate with the receptor. The tyrosine kinase domain is also defined, in part, by its homology to similar domains in other tyrosine kinase activity containing proteins. See, e.g., Yarden et al. (1986) *Nature* 323: 226–232. As such, the actual boundaries, determined by homology to other similar domains, may vary by a few amino acid residues, perhaps as many as about 7 residues, but probably within about 4 residues, and more probably within about one or two residues. A protein substantially lacks a complete intracellular region when it lacks a prototypical intracellular region, particularly lacking a tyrosine kinase domain; a similar concept is provided with respect to lack of a complete transmembrane region.

A typical PDGF-R nucleic acid sequence encodes a transitory $NH_2$-terminal hydrophobic sequence, which is usually cleaved during the membrane translocation process. The classical function of a signal sequence is to direct the nascent polypeptide chain to membrane bound ribosomes, thereby leading to membrane translocation and subsequent processing and targeting steps. Since the signal sequence is typically removed in the translocation process, the signal sequence is absent in a mature polypeptide. However, other features of the amino proximal sequence of the mature protein may also be important for expression or correct localization or targeting of receptor fragments.

The putative boundaries of the different regions of the receptors are indicated in Table 1, derived, in part, by homology to the mouse PDGF receptor. In particular, a hydrophobic segment has been identified and designated a transmembrane segment, due to its structural homology and physical properties characteristic of a membrane spanning segment. The segment divides the protein into an extracellular region and an intracellular region. The intracellular region has homology to various other receptors believed to exhibit tyrosine kinase activity, though this receptor has an insert region, as indicated, which is embedded within the region of high homology to other tyrosine kinase segments.

TABLE 1

| | approximate segment boundaries | |
|---|---|---|
| | Type B | Type A |
| XR | leu (1)-lys (499) | gln (1)-glu (501) |
| TM | val (500)-trp (524) | leu (502)-trp (526) |
| TK1 | arg (572)-his (662) | leu (572)-his (664) |
| KI | arg (663)-leu (766) | lys (665)-leu (767) |
| TK2 | ser (767)-phe (919) | thr (768)-phe (920) |

The intracellular region of the receptor contains a tyrosine kinase activity. PDGF receptors have a characteristic split tyrosine kinase domain, with an insert segment of about 103 or 104 amino acids. This insert segment has regulatory and other properties which are described in greater detail below.

The present invention provides isolated nucleic acids and polypeptides relating to PDGF receptors. An isolated molecule is one which is substantially separated from substances which naturally accompany the molecule when found in its natural form. For example, an isolated polypeptide is one which is substantially purified away from naturally accompanying human cell components, e.g., human nucleic acids, lipids, and other proteins. Of particular interest are contiguous segments of polypeptide which might be separated by genetic recombination or deletion techniques. Thus, an expression product of an isolated and manipulated genetic sequence is an isolated polypeptide, as used herein, even if expressed in a homologous cell type. Synthetically made forms or molecules expressed by heterologous cells are inherently isolated molecules.

Physiologically, the receptor is responsible for initiating a number of metabolic changes in, e.g., phosphatidylinositol levels, pH, calcium ion levels, cytoskeletal structure, gene expression, cAMP levels, and ligand receptor levels. Many of these metabolic changes are characteristic of a mitogenic, e.g., ligand induced, response.

The type A and type B PDGF receptor forms, when combined in the various dimer combinations into functional receptor complexes, also have characteristic binding affinities for the various forms of PDGF's, e.g., for the AA, AB and BB forms. For example, a type B isoform receptor binds the BB isoform PDGF at high affinity, the AB heteroform PDGF with lower affinity, and the AA isoform PDGF at low or no affinity. The type A isoform receptor binds to the AA isoform PDGF with high affinity, and with the AB heterodimer and BB isoform PDGF's with lower affinity.

The term "ligand" refers to molecules, usually members of the platelet-derived growth factor family, that bind the segments involved in the growth factor binding. Also, a ligand is a molecule which serves either as a natural ligand to which the receptor, or an analogue of the receptor, binds, or a functional analogue of a natural ligand. The functional analogue may be a ligand with structural modifications, or may be a wholly unrelated molecule which has a molecular shape which interacts with the appropriate ligand binding determinants. The ligands may serve as agonists or antagonists, see, e.g., Goodman et al. (eds) (1990) *Goodman & Gilman's: The Pharmacological Bases of Therapeutics* (8th ed), Pergamon Press.

II. Polypeptides

The PDGF receptor is believed to be a dimer of similar polypeptides and the component polypeptides determine the dimerized receptor binding affinity for ligand.

The AA homodimer PDGF ligand is preferentially bound with high affinity by one form of the hPDGF receptor, and this form is correlated with a polypeptide chain referred to as the A receptor, the a receptor, and, as used herein, the type A receptor polypeptide (A-hPDGF-R). The receptor dimer is apparently a homodimer of the type A receptor polypeptides.

The BB homodimer PDGF ligand is preferentially bound with high affinity by two forms of the hPDGF-receptor. These forms are correlated with a second polypeptide chain referred to as the B receptor, the β receptor, and, as used herein, the type B receptor polypeptide (B-hPDGF-R). These two receptor dimer forms are apparently the homodimer of the B receptor polypeptides and the heterodimer type B/type A form.

The designations type A and type B polypeptides are each intended to also cover all alleles of each respective isoform. Thus, naturally occurring variants of each are embraced by the invention, as are other variants, analogues, and modified sequences.

The nucleotide sequence of a cDNA sequence encoding one B-hPDGF-R allele is set forth in Table 2 together with the deduced amino acid sequence of the receptor precursor (SEQ ID NOS:1–2). The following descriptions indicate presumed gross structural and functional characterizations based upon analogy to the mouse and other growth factor receptors and proteins.

The sequence beginning at the amino acid numbered 1 corresponds to the putative amino terminus of a mature form of a human PDGF-R. The first 32 amino acids (designated −32 to −1) encode the putative signal peptide sequence. The putative transmembrane sequence corresponds to amino acid residues val(500) to trp(524). Potential N-glycosylation sites are at positions corresponding to amino acids asn(13)–ser(15); asn(57)–(50); asn(71)-ser(73); asn(183)–(185); asn(198)–(200); asn(260)–(262); asn(275)–(277); asn(322)–(324); asn(339)–(341); asn(436)–(438); and asn(447)–(449). The putative tyrosine kinase domain is interrupted by an amino acid insertion between about arg(663) and leu (766), see Table 1. The putative polyadenylation site is at the 3' end of the given cDNA sequence.

TABLE 2

Sequence of one type B human PDGF receptor polypeptide allele and protein

| | |
|---|---:|
| TGTTCTCCTGAGCCTTCAGGAGCCTGCACCAGTCCTGCCTGTCCTTCTACTC | 52 |
| AGCTGTTACCCACTCTGGGACCAGCAGTCTTTCTGATAACTGGGAGAGGGCAGTAAGGAGGACTTCC | 119 |
| TGGAGGGGGTGACTGTCCAGAGCCTGGAACTGTGCCCACACCAGAAGCCATCAGCAGCAAGGACACC | 186 |
| ATG CGG CTT CCG GGT GCG ATG CCA GCT CTG GCC CTC AAA GGC GAG CTG CTG | 237 |
| Met Arg Leu Pro Gly Ala Met Pro Ala Leu Ala Leu Lys Gly Glu Leu Leu | −15 |
| TTG CTG TCT CTC CTG TTA CTT CTG GAA CCA CAG ATC TCT CAG GGC CTG GTC | 288 |
| Leu Leu Ser Leu Leu Leu Leu Glu Pro Gln Ile Ser Gln Gly Leu Val | 2 |
| GTC ACA CCC CCG GGG CCA GAG CTT GTC CTC AAT GTC TCC AGC ACC TTC GTT | 339 |
| Val Thr Pro Pro Gly Pro Glu Leu Val Leu Asn Val Ser Ser Thr Phe Val | 19 |
| CTG ACC TGC TCG GGT TCA GCT CCG GTG GTG TGG GAA CGG ATG TCC CAG GAG | 390 |
| Leu Thr Cys Ser Gly Ser Ala Pro Val Val Trp Glu Arg Met Ser Gln Glu | 36 |
| CCC CCA CAG GAA ATG GCC AAG GCC CAG GAT GGC ACC TTC TCC AGC GTG CTC | 441 |
| Pro Pro Gln Glu Met Ala Lys Ala Gln Asp Gly Thr Phe Ser Ser Val Leu | 53 |

TABLE 2-continued

Sequence of one type B human PDGF
receptor polypeptide allele and protein

```
ACA CTG ACC AAC CTC ACT GGG CTA GAC ACG GGA GAA TAC TTT TGC ACC CAC   492
Thr Leu Thr Asn Leu Thr Gly Leu Asp Thr Gly Glu Tyr Phe Cys Thr His    70

AAT GAC TCC CGT GGA CTG GAG ACC GAT GAG CGG AAA CGG CTC TAC ATC TTT   543
Asn Asp Ser Arg Gly Leu Glu Thr Asp Glu Arg Lys Arg Leu Tyr Ile Phe    87

GTG CCA GAT CCC ACC GTG GGC TTC CTC CCT AAT GAT GCC GAG GAA CTA TTC   594
Val Pro Asp Pro Thr Val Gly Phe Leu Pro Asn Asp Ala Glu Glu Leu Phe   104

ATC TTT CTC ACG GAA ATA ACT GAG ATC ACC ATT CCA TGC CGA GTA ACA GAC   645
Ile Phe Leu Thr Glu Ile Thr Glu Ile Thr Ile Pro Cys Arg Val Thr Asp   121

CCA CAG CTG GTG GTG ACA CTG CAC GAG AAG AAA GGG GAC GTT GCA CTG CCT   696
Pro Gln Leu Val Val Thr Leu His Glu Lys Lys Gly Asp Val Ala Leu Pro   138

GTC CCC TAT GAT CAC CAA CGT GGC TTT TCT GGT ATC TTT GAG GAC AGA AGC   747
Val Pro Tyr Asp His Gln Arg Gly Phe Ser Gly Ile Phe Glu Asp Arg Ser   155

TAC ATC TGC AAA ACC ACC ATT GGG GAC AGG GAG GTG GAT TCT GAT GCC TAC   798
Tyr Ile Cys Lys Thr Thr Ile Gly Asp Arg Glu Val Asp Ser Asp Ala Tyr   172

TAT GTC TAC AGA CTC CAG GTG TCA TCC ATC AAC GTC TCT GTG AAC GCA GTG   849
Tyr Val Tyr Arg Leu Gln Val Ser Ser Ile Asn Val Ser Val Asn Ala Val   189

CAG ACT GTG GTC CGC CAG GGT GAG AAC ATC ACC CTC ATG TGC ATT GTG ATC   900
Gln Thr Val Val Arg Gln Gly Glu Asn Ile Thr Leu Met Cys Ile Val Ile   206

GGG AAT GAT GTG GTC AAC TTC GAG TGG ACA TAC CCC CGC AAA GAA AGT GGG   951
Gly Asn Asp Val Val Asn Phe Glu Trp Thr Tyr Pro Arg Lys Glu Ser Gly   223

CGG CTG GTG GAG CCG GTG ACT GAC TTC CTC TTG GAT ATG CCT TAC CAC ATC  1002
Arg Leu Val Glu Pro Val Thr Asp Phe Leu Leu Asp Met Pro Tyr His Ile   240

CGC TCC ATC CTG CAC ATC CCC AGT GCC GAG TTA GAA GAC TCG GGG ACC TAC  1053
Arg Ser Ile Leu His Ile Pro Ser Ala Glu Leu Glu Asp Ser Gly Thr Tyr   257

ACC TGC AAT GTG ACG GAG AGT GTG AAT GAC CAT CAG GAT GAA AAG GCC ATC  1104
Thr Cys Asn Val Thr Glu Ser Val Asn Asp His Gln Asp Glu Lys Ala Ile   274

AAC ATC ACC GTG GTT GAG AGC GGC TAC GTG CGG CTC CTG GGA GAG GTG GGC  1155
Asn Ile Thr Val Val Glu Ser Gly Tyr Val Arg Leu Leu Gly Glu Val Gly   291

ACA CTA CAA TTT GCT GAG CTG CAT CGG AGC CGG ACA CTG CAG GTA GTG TTC  1206
Thr Leu Gln Phe Ala Glu Leu His Arg Ser Arg Thr Leu Gln Val Val Phe   308

GAG GCC TAC CCA CCG CCC ACT GTC CTG TGG TTC AAA GAC AAC CGC ACC CTG  1257
Glu Ala Tyr Pro Pro Pro Thr Val Leu Trp Phe Lys Asp Asn Arg Thr Leu   325

GGC GAC TCC AGC GCT GGC GAA ATC GCC CTG TCC ACG CGC AAC GTG TCG GAG  1308
Gly Asp Ser Ser Ala Gly Glu Ile Ala Leu Ser Thr Arg Asn Val Ser Glu   342

ACC CGG TAT GTG TCA GAG CTG ACA CTG GTT CGC GTG AAG GTG GCA GAG GCT  1359
Thr Arg Tyr Val Ser Glu Leu Thr Leu Val Arg Val Lys Val Ala Glu Ala   359

GGC CAC TAC ACC ATG CGG GCC TTC CAT GAG GAT GCT GAG GTC CAG CTC TCC  1410
Gly His Tyr Thr Met Arg Ala Phe His Glu Asp Ala Glu Val Gln Leu Ser   376

TTC CAG CTA CAG ATC AAT GTC CCT GTC CGA GTG CTG GAG CTA AGT GAG AGC  1461
Phe Gln Leu Gln Ile Asn Val Pro Val Arg Val Leu Glu Leu Ser Glu Ser   393

CAC CCT GAC AGT GGG GAA CAG ACA GTC CGC TGT CGT GGC CGG GGC ATG CCG  1512
His Pro Asp Ser Gly Glu Gln Thr Val Arg Cys Arg Gly Arg Gly Met Pro   410

CAG CCG AAC ATC ATC TGG TCT GCC TGC AGA GAC CTC AAA AGG TGT CCA CGT  1563
Gln Pro Asn Ile Ile Trp Ser Ala Cys Arg Asp Leu Lys Arg Cys Pro Arg   427

GAG CTG CCG CCC ACG CTG CTG GGG AAC AGT TCC GAA GAG GAG AGC CAG CTG  1614
Glu Leu Pro Pro Thr Leu Leu Gly Asn Ser Ser Glu Glu Glu Ser Gln Leu   444

GAG ACT AAC GTG ACG TAC TGG GAG GAG GAG CAG GAG TTT GAG GTG GTG AGC  1665
Glu Thr Asn Val Thr Tyr Trp Glu Glu Glu Gln Glu Phe Glu Val Val Ser   461

ACA CTG CGT CTG CAG CAC GTG GAT CGG CCA CTG TCG GTG CGC TGC ACG CTG  1716
Thr Leu Arg Leu Gln His Val Asp Arg Pro Leu Ser Val Arg Cys Thr Leu   478
```

TABLE 2-continued

Sequence of one type B human PDGF
receptor polypeptide allele and protein

```
CGC AAC GCT GTG GGC CAG GAC ACG CAG GAG GTC ATC GTG GTG CCA CAC TCC  1767
Arg Asn Ala Val Gly Gln Asp Thr Gln Glu Val Ile Val Val Pro His Ser   495

TTG CCC TTT AAG GTG GTG GTG ATC TCA GCC ATC CTG GCC CTG GTG GTG CTC  1818
Leu Pro Phe Lys Val Val Val Ile Ser Ala Ile Leu Ala Leu Val Val Leu   512

ACC ATC ATC TCC CTT ATC ATC CTC ATC ATG CTT TGG CAG AAG AAG CCA CGT  1869
Thr Ile Ile Ser Leu Ile Ile Leu Ile Met Leu Trp Gln Lys Lys Pro Arg   529

TAC GAG ATC CGA TGG AAG GTG ATT GAG TCT GTG AGC TCT GAC GGC CAT GAG  1920
Tyr Glu Ile Arg Trp Lys Val Ile Glu Ser Val Ser Ser Asp Gly His Glu   546

TAC ATC TAC GTG GAC CCC ATG CAG CTG CCC TAT GAC TCC ACG TGG GAG CTG  1971
Tyr Ile Tyr Val Asp Pro Met Gln Leu Pro Tyr Asp Ser Thr Trp Glu Leu   563

CCG CGG GAC CAG CTT GTG CTG GGA CGC ACC CTC GGC TCT GGG GCC TTT GGG  2022
Pro Arg Asp Gln Leu Val Leu Gly Arg Thr Leu Gly Ser Gly Ala Phe Gly   580

CAG GTG GTG GAG GCC ACA GCT CAT GGT CTG AGC CAT TCT CAG GCC ACG ATG  2073
Gln Val Val Glu Ala Thr Ala His Gly Leu Ser His Ser Gln Ala Thr Met   597

AAA GTG GCC GTC AAG ATG CTT AAA TCC ACA GCC CGC AGC AGT GAG AAG CAA  2124
Lys Val Ala Val Lys Met Leu Lys Ser Thr Ala Arg Ser Ser Glu Lys Gln   614

GCC CTT ATG TCG GAG CTG AAG ATC ATG AGT CAC CTT GGG CCC CAC CTG AAC  2175
Ala Leu Met Ser Glu Leu Lys Ile Met Ser His Leu Gly Pro His Leu Asn   631

GTG GTC AAC CTG TTG GGG GCC TGC ACC AAA GGA GGA CCC ATC TAT ATC ATC  2226
Val Val Asn Leu Leu Gly Ala Cys Thr Lys Gly Gly Pro Ile Tyr Ile Ile   648

ACT GAG TAC TGC CGC TAC GGA GAC CTG GTG GAC TAC CTG CAC CGC AAC AAA  2277
Thr Glu Tyr Cys Arg Tyr Gly Asp Leu Val Asp Tyr Leu His Arg Asn Lys   665

CAC ACC TTC CTG CAG CAC CAC TCC GAC AAG CGC CGC CCG CCC AGC GCG GAG  2328
His Thr Phe Leu Gln His His Ser Asp Lys Arg Arg Pro Pro Ser Ala Glu   682

CTC TAC AGC AAT GCT CTG CCC GTT GGG CTC CCC CTG CCC AGC CAT GTG TCC  2379
Leu Tyr Ser Asn Ala Leu Pro Val Gly Leu Pro Leu Pro Ser His Val Ser   699

TTG ACC GGG GAG AGC GAC GGT GGC TAC ATG GAC ATG AGC AAG GAC GAG TCG  2430
Leu Thr Gly Glu Ser Asp Gly Gly Tyr Met Asp Met Ser Lys Asp Glu Ser   716

GTG GAC TAT GTG CCC ATG CTG GAC ATG AAA GGA GAC GTC AAA TAT GCA GAC  2481
Val Asp Tyr Val Pro Met Leu Asp Met Lys Gly Asp Val Lys Tyr Ala Asp   733

ATC GAG TCC TCC AAC TAC ATG GCC CCT TAC GAT AAC TAC GTT CCC TCT GCC  2532
Ile Glu Ser Ser Asn Tyr Met Ala Pro Tyr Asp Asn Tyr Val Pro Ser Ala   750

CCT GAG AGG ACC TGC CGA GCA ACT TTG ATC AAC GAG TCT CCA GTG CTA AGC  2583
Pro Glu Arg Thr Cys Arg Ala Thr Leu Ile Asn Glu Ser Pro Val Leu Ser   767

TAC ATG GAC CTC GTG GGC TTC AGC TAC CAG GTG GCC AAT GGC ATG GAG TTT  2634
Tyr Met Asp Leu Val Gly Phe Ser Tyr Gln Val Ala Asn Gly Met Glu Phe   784

CTG GCC TCC AAG AAC TGC GTC CAC AGA GAC CTG GCG GCT AGG AAC GTG CTC  2685
Leu Ala Ser Lys Asn Cys Val His Arg Asp Leu Ala Ala Arg Asn Val Leu   801

ATC TGT GAA GGC AAG CTG GTC AAG ATC TGT GAC TTT GGC CTG GCT CGA GAC  2736
Ile Cys Glu Gly Lys Leu Val Lys Ile Cys Asp Phe Gly Leu Ala Arg Asp   818

ATC ATG CGG GAC TCG AAT TAC ATC TCC AAA GGC AGC ACC TTT TTG CCT TTA  2787
Ile Met Arg Asp Ser Asn Tyr Ile Ser Lys Gly Ser Thr Phe Leu Pro Leu   835

AAG TGG ATG GCT CCG GAG AGC ATC TTC AAC AGC CTC TAC ACC ACC CTG AGC  2838
Lys Trp Met Ala Pro Glu Ser Ile Phe Asn Ser Leu Tyr Thr Thr Leu Ser   852

GAC GTG TGG TCC TTC GGG ATC CTG CTC TGG GAG ATC TTC ACC TTG GGT GGC  2889
Asp Val Trp Ser Phe Gly Ile Leu Leu Trp Glu Ile Phe Thr Leu Gly Gly   869

ACC CCT TAC CCA GAG CTG CCC ATG AAC GAG CAG TTC TAC AAT GCC ATC AAA  2940
Thr Pro Tyr Pro Glu Leu Pro Met Asn Glu Gln Phe Tyr Asn Ala Ile Lys   886

CGG GGT TAC CGC ATG GCC CAG CCT GCC CAT GCC TCC GAC GAG ATC TAT GAG  2991
Arg Gly Tyr Arg Met Ala Gln Pro Ala His Ala Ser Asp Glu Ile Tyr Glu   903

ATC ATG CAG AAG TGC TGG GAA GAG AAG TTT GAG ATT CGG CCC CCC TTC TCC  3042
```

TABLE 2-continued

Sequence of one type B human PDGF
receptor polypeptide allele and protein

| | | | | | | | | | | | | | | |
|---|---|---|---|---|---|---|---|---|---|---|---|---|---|---|
| Ile | Met | Gln | Lys | Cys | Trp | Glu | Glu | Lys | Phe | Glu | Ile | Arg | Pro | Pro | Phe | Ser | 920 |

```
CAG CTG GTG CTG CTT CTC GAG AGA CTG TTG GGC GAA GGT TAC AAA AAG AAG    3093
Gln Leu Val Leu Leu Leu Glu Arg Leu Leu Gly Glu Gly Tyr Lys Lys Lys     937

TAC CAG CAG GTG GAT GAG GAG TTT CTG AGG AGT GAC CAC CCA GCC ATC CTT    3144
Tyr Gln Gln Val Asp Glu Glu Phe Leu Arg Ser Asp His Pro Ala Ile Leu     954

CGG TCC CAG GCC CGC TTG CCT GGG TTC CAT GGC CTC CGA TCT CCC CTG GAC    3195
Arg Ser Gln Ala Arg Leu Pro Gly Phe His Gly Leu Arg Ser Pro Leu Asp     971

ACC AGC TCC GTC CTC TAT ACT GCC GTG CAG CCC AAT GAG GGT GAC AAC GAC    3246
Thr Ser Ser Val Leu Tyr Thr Ala Val Gln Pro Asn Glu Gly Asp Asn Asp     989

TAT ATC ATC CCC CTG CCT GAC CCC AAA CCT GAG GTT GCT GAC GAG GGC CCA    3297
Tyr Ile Ile Pro Leu Pro Asp Pro Lys Pro Glu Val Ala Asp Glu Gly Pro    1005

CTG GAG GGT TCC CCC AGC CTA GCC AGC TCC ACC CTG AAT GAA GTC AAC ACC    3348
Leu Glu Gly Ser Pro Ser Leu Ala Ser Ser Thr Leu Asn Glu Val Asn Thr    1022

TCC TCA ACC ATC TCC TGT GAC AGC CCC CTG GAG CCC CAG GAC GAA CCA GAG    3399
Ser Ser Thr Ile Ser Cys Asp Ser Pro Leu Glu Pro Gln Asp Glu Pro Glu    1039

CCA GAG CCC CAG CTT GAG CTC CAG GTG GAG CCG GAG CCG GAG CTG GAA CAG    3450
Pro Glu Pro Gln Leu Glu Leu Gln Val Glu Pro Glu Pro Glu Leu Glu Gln    1056

TTG CCG GAT TCG GGG TGC CCT GCG CCT CGG GCG GAA GCA GAG GAT AGC TTC    3501
Leu Pro Asp Ser Gly Cys Pro Ala Pro Arg Ala Glu Ala Glu Asp Ser Phe    1073

CTG TAGGGGGCTGGCCCCTACCCTGCCCTGCCTGAAGCTCCCCCGCTGCCAGCACCCAGCATCTCC   3567
Leu                                                                    1074

TGGCCTGGCCTGGCCGGGCTTCCTGTCAGCCAGGCTGCCCTTATCAGCTGTCCCCTTCTGGAAGCTT   3634

TCTGCTCCTGACGTGTTGTGCCCCAAACCCTGGGGCTGGCTTAGGAGGCAAGAAAACTGCAGGGGCC   3701

GTGACCAGCCCTCTGCCTCCAGGGAGGCCAACTGACTCTGAGCCAGGGTTCCCCAGGGAACTCAGT    3768

TTTCCCATATGTAAGATGGGAAAGTTAGGCTTGATGACCCAGAATCTAGGATTCTCTCCCTGGCTGA   3835

CAGGTGGGGAGACCGAATCCCTCCCTGGGAAGATTCTTGGAGTTACTGAGGTGGTAAATTAACTTTT   3902

TTCTGTTCAGCCAGCTACCCCTCAAGGAATCATAGCTCTCTCCTCGCACTTTTATCCACCCAGGAGC   3969

TAGGGAAGAGACCCTAGCCTCCCTGGCTGCTGGCTGAGCTAGGGCCTAGCCTTGAGCAGTGTTGCCT   4036

CATCCAGAAGAAAGCCAGTCTCCTCCCTATGATGCCAGTCCCTGCGTTCCCTGGCCCGAGCTGGTCT   4103

GGGGCCATTAGGCAGCCTAATTAATGCTGGAGGCTGAGCCAAGTACAGGACACCCCAGCCTGCAGC    4170

CCTTGCCCAGGGCACTTGGAGCACACGCAGCCATAGCAAGTGCCTGTGTCCCTGTCCTTCAGGCCCA   4237

TCAGTCCTGGGGCTTTTTCTTTATCACCCTCAGTCTTAATCCATCCACCAGAGTCTAGAAGGCCAGA   4304

GGGGCCCCGCATCTGTGATGAGAATGTAAATGTGCCAGTGTGGAGTGGCCACGTGTGTGTGCCAGAT   4371

ATGGCCCTGGCTCTGCATTGGACCTGCTATGAGGCTTTGGAGGAATCCCTCACCCTCTCTGGGCCTC   4438

AGTTTCCCCTTCAAAAAATGAATAAGTCGGACTTATTAACTCTGAGTGCCTTGCCAGCACTAACATT   4505

CTAGAGTATCCAGGTGGTTGCACATTTGTCCAGATGAAGCAAGGCCATATACCCTAAACTTCCATCC   4572

TGGGGGTCAGCTGGGCTCCTGGGAGATTCCAGATCACACATCACACTCTGGGGACTCAGGAACCATG   4639

CCCCTTCCCCAGGCCCCCAGCAAGTCTCAAGAACACAGCTGCACAGGCCTTGACTTAGAGTGACAGC   4706

CGGTGTCCTGGAAAGCCCCCAGCAGCTGCCCCAGGGACATGGGAAGACCACGGGACCTCTTTCACTA   4773

CCCACGATGACCTCCGGGGGTATCCTGGGCAAAAGGGACAAAGAGGGCAAATGAGATCACCTCCTGC   4840

AGCCCACCACTCCAGCACCTGTGCCGAGGTCTGCGTCGAAGACAGAATGGACAGTGAGGACAGTTAT   4907

GTCTTGTAAAAGACAAGAAGCTTCAGATGGGTACCCCAAGAAGGATGTGAGAGGTGGGCGCTTTGGA   4974

GGTTTGCCCCTCACCCACCAGCTGCCCCATCCCTGAGGCAGCGCTCCATGGGGGTATGGTTTTGTCA   5041
```

TABLE 2-continued

Sequence of one type B human PDGF
receptor polypeptide allele and protein

| | |
|---|---|
| CTGCCCAGACCTAGCAGTGACATCTCATTGTCCCCAGCCCAGTGGGCATTGGAGGTGCCAGGGGAGT | 5108 |
| CAGGGTTGTAGCCAAGACGCCCCCGCACGGGGAGGGTTGGGAAGGGGGTGCAGGAAGCTCAACCCCT | 5175 |
| CTGGGCACCAACCCTGCATTGCAGGTTGGCACCTTACTTCCCTGGGATCCCAGAGTTGGTCCAAGGA | 5242 |
| GGGAGAGTGGGTTCTCAATACGGTACCAAAGATATAATCACCTAGGTTTACAAATATTTTTAGGACT | 5309 |
| CACGTTAACTCACATTTATACAGCAGAAATGCTATTTTGTATGCTGTTAAGTTTTTCTATCTGTGTA | 5376 |
| CTTTTTTTTAAGGGAAAGATTTTAATATTAAACCTGGTGCTTCTCACTCAC | 5427 |

ẑ

The nucleotide sequence of a cDNA sequence encoding one allele of a type A hPDGF-R is set forth in Table 3, together with the deduced amino acid sequence of the receptor (SEQ ID NOS:3–4). The structural features, as described, are again based upon analogy to the mouse PDGF receptors and other growth factor receptors and proteins.

The sequence beginning at the amino acid numbered 1 corresponds to the putative amino terminus of a mature form of a human PDGF-R. The first 23 amino acids (designated −23 to −1) encode the putative signal peptide sequence. The putative transmembrane sequence corresponds to amino acid residues leu(502) to trp(526). Potential N-glycosylation sites are at positions corresponding to amino acids asn(19) –(21); asn(53)–(55); asn(80)–(82); asn(156)–(158); asn (330)–(332); asn(336)–(338); asn(435)–(437); and asn(445) –(447). The putative tyrosine kinase domain is interrupted by an amino acid insertion between about lys(665) and leu(767), see Table 1.

TABLE 3

Sequence of a human type A
PDGF receptor polypeptide allele and protein

| | | |
|---|---|---|
| TTGGAGCTACAGGGAGAGAAACAGAGGAGGAGACTGCAAGAGATCATTGGAGGCCGTGGGC | | 61 |
| ACGCTCTTTACTCCATGTGTGGGACATTCATTGCGGAATAACATCGGAGGAGAAGTTTCCCAGAGCT | | 128 |
| ATG GGG ACT TCC CAT CCG GCG TTC CTG GTC TTA GGC TGT CTT CTC ACA GGG | | 179 |
| Met Gly Thr Ser His Pro Ala Phe Leu Val Leu Gly Cys Leu Leu Thr Gly | | −7 |
| CTG AGC CTA ATC CTC TGC CAG CTT TCA TTA CCC TCT ATC CTT CCA AAT GAA | | 230 |
| Leu Ser Leu Ile Leu Cys Gln Leu Ser Leu Pro Ser Ile Leu Pro Asn Glu | | 11 |
| AAT GAA AAG GTT GTG CAG CTG AAT TCA TCC TTT TCT CTG AGA TGC TTT GGG | | 281 |
| Asn Glu Lys Val Val Gln Leu Asn Ser Ser Phe Ser Leu Arg Cys Phe Gly | | 28 |
| GAG AGT GAA GTG AGC TGG CAG TAC CCC ATG TCT GAA GAA GAG AGC TCC GAT | | 332 |
| Glu Ser Glu Val Ser Trp Gln Tyr Pro Met Ser Glu Glu Glu Ser Ser Asp | | 45 |
| GTG GAA ATC AGA AAT GAA GAA AAC AAC AGC GGC CTT TTT GTG ACG GTC TTG | | 383 |
| Val Glu Ile Arg Asn Glu Glu Asn Asn Ser Gly Leu Phe Val Thr Val Leu | | 62 |
| GAA GTG AGC AGT GCC TCG GCG GCC CAC ACA GGG TTG TAC ACT TGC TAT TAC | | 434 |
| Glu Val Ser Ser Ala Ser Ala Ala His Thr Gly Leu Tyr Thr Cys Tyr Tyr | | 79 |
| AAC CAC ACT CAG ACA GAA GAG AAT GAG CTT GAA GGC AGG CAC ATT TAC ATC | | 485 |
| Asn His Thr Gln Thr Glu Glu Asn Glu Leu Glu Gly Arg His Ile Tyr Ile | | 96 |
| TAT GTG CCA GAC CCA GAT GTA GCC TTT GTA CCT CTA GGA ATG ACG GAT TAT | | 536 |
| Tyr Val Pro Asp Pro Asp Val Ala Phe Val Pro Leu Gly Met Thr Asp Tyr | | 113 |
| TTA GTC ATC GTG GAG GAT GAT GAT TCT GCC ATT ATA CCT TGT CGC ACA ACT | | 587 |
| Leu Val Ile Val Glu Asp Asp Asp Ser Ala Ile Ile Pro Cys Arg Thr Thr | | 130 |
| GAT CCC GAG ACT CCT GTA ACC TTA CAC AAC AGT GAG GGG GTG GTA CCT GCC | | 638 |
| Asp Pro Glu Thr Pro Val Thr Leu His Asn Ser Glu Gly Val Val Pro Ala | | 147 |
| TCC TAC GAC AGC AGA CAG GGC TTT AAT GGG ACC TTC ACT GTA GGG CCC TAT | | 689 |
| Ser Tyr Asp Ser Arg Gln Gly Phe Asn Gly Thr Phe Thr Val Gly Pro Tyr | | 164 |
| ATC TGT GAG GCC ACC GTC AAA GGA AAG AAG TTC CAG ACC ATC CCA TTT AAT | | 740 |
| Ile Cys Glu Ala Thr Val Lys Gly Lys Lys Phe Gln Thr Ile Pro Phe Asn | | 181 |
| GTT TAT GCT TTA AAA GCA ACA TCA GAG CTG GAT CTA GAA ATG GAA GCT CTT | | 791 |

TABLE 3-continued

Sequence of a human type A
PDGF receptor polypeptide allele and protein

| | | | | | | | | | | | | | | |
|---|---|---|---|---|---|---|---|---|---|---|---|---|---|---|
| Val | Tyr | Ala | Leu | Lys | Ala | Thr | Ser | Glu | Leu | Asp | Leu | Glu | Met | Glu | Ala | Leu | 198 |

```
AAA ACC GTG TAT AAG TCA GGG GAA ACG ATT GTG GTC ACC TGT GCT GTT TTT    842
Lys Thr Val Tyr Lys Ser Gly Glu Thr Ile Val Val Thr Cys Ala Val Phe    215

AAC AAT GAG GTG GTT GAC CTT CAA TGG ACT TAC CCT GGA GAA GTG AAA GGC    893
Asn Asn Glu Val Val Asp Leu Gln Trp Thr Tyr Pro Gly Glu Val Lys Gly    232

AAA GGC ATC ACA ATG CTG GAA GAA ATC AAA GTC CCA TCC ATC AAA TTG GTG    944
Lys Gly Ile Thr Met Leu Glu Glu Ile Lys Val Pro Ser Ile Lys Leu Val    249

TAC ACT TTG ACG GTC CCC GAG GCC ACG GTG AAA GAC AGT GGA GAT TAC GAA    995
Tyr Thr Leu Thr Val Pro Glu Ala Thr Val Lys Asp Ser Gly Asp Tyr Glu    266

TGT GCT GCC CGC CAG GCT ACC AGG GAG GTC AAA GAA ATG AAG AAA GTC ACT   1046
Cys Ala Ala Arg Gln Ala Thr Arg Glu Val Lys Glu Met Lys Lys Val Thr    283

ATT TCT GTC CAT GAG AAA GGT TTC ATT GAA ATC AAA CCC ACC TTC AGC CAG   1097
Ile Ser Val His Glu Lys Gly Phe Ile Glu Ile Lys Pro Thr Phe Ser Gln    300

TTG GAA GCT GTC AAC CTG CAT GAA GTC AAA CAT TTT GTT GTA GAG GTG CGG   1148
Leu Glu Ala Val Asn Leu His Glu Val Lys His Phe Val Val Glu Val Arg    317

GCC TAC CCA CCT CCC AGG ATA TCC TGG CTG AAA AAC AAT CTG ACT CTG ATT   1199
Ala Tyr Pro Pro Pro Arg Ile Ser Trp Leu Lys Asn Asn Leu Thr Leu Ile    334

GAA AAT CTC ACT GAG ATC ACC ACT GAT GTG GAA AAG ATT CAG GAA ATA AGG   1250
Glu Asn Leu Thr Glu Ile Thr Thr Asp Val Glu Lys Ile Gln Glu Ile Arg    351

TAT CGA AGC AAA TTA AAG CTG ATC CGT GCT AAG GAA GAA GAC AGT GGC CAT   1301
Tyr Arg Ser Lys Leu Lys Leu Ile Arg Ala Lys Glu Glu Asp Ser Gly His    368

TAT ACT ATT GTA GCT CAA AAT GAA GAT GCT GTG AAG AGC TAT ACT TTT GAA   1352
Tyr Thr Ile Val Ala Gln Asn Glu Asp Ala Val Lys Ser Tyr Thr Phe Glu    385

CTG TTA ACT CAA GTT CCT TCA TCC ATT CTG GAC TTG GTC GAT GAT CAC CAT   1403
Leu Leu Thr Gln Val Pro Ser Ser Ile Leu Asp Leu Val Asp Asp His His    402

GGC TCA ACT GGG GGA CAG ACG GTG AGG TGC ACA GCT GAA GGC ACG CCG CTT   1454
Gly Ser Thr Gly Gly Gln Thr Val Arg Cys Thr Ala Glu Gly Thr Pro Leu    419

CCT GAT ATT GAG TGG ATG ATA TGC AAA GAT ATT AAG AAA TGT AAT AAT GAA   1505
Pro Asp Ile Glu Trp Met Ile Cys Lys Asp Ile Lys Lys Cys Asn Asn Glu    436

ACT TCC TGG ACT ATT TTG GCC AAC AAT GTC TCA AAC ATC ATC ACG GAG ATC   1556
Thr Ser Trp Thr Ile Leu Ala Asn Asn Val Ser Asn Ile Ile Thr Glu Ile    453

CAC TCC CGA GAC AGG AGT ACC GTG GAG GGC CGT GTG ACT TTC GCC AAA GTG   1607
His Ser Arg Asp Arg Ser Thr Val Glu Gly Arg Val Thr Phe Ala Lys Val    470

GAG GAG ACC ATC GCC GTG CGA TGC CTG GCT AAG AAT CTC CTT GGA GCT GAG   1658
Glu Glu Thr Ile Ala Val Arg Cys Leu Ala Lys Asn Leu Leu Gly Ala Glu    487

AAC CGA GAG CTG AAG CTG GTG GCT CCC ACC CTG CGT TCT GAA CTC ACG GTG   1709
Asn Arg Glu Leu Lys Leu Val Ala Pro Thr Leu Arg Ser Glu Leu Thr Val    504

GCT GCT GCA GTC CTG GTG CTG TTG GTG ATT GTG ATC ATC TCA CTT ATT GTC   1760
Ala Ala Ala Val Leu Val Leu Leu Val Ile Val Ile Ile Ser Leu Ile Val    521

CTG GTT GTC ATT TGG AAA CAG AAA CCG AGG TAT GAA ATT CGC TGG AGG GTC   1811
Leu Val Val Ile Trp Lys Gln Lys Pro Arg Tyr Glu Ile Arg Trp Arg Val    538

ATT GAA TCA ATC AGC CCA GAT GGA CAT GAA TAT ATT TAT GTG GAC CCG ATG   1862
Ile Glu Ser Ile Ser Pro Asp Gly His Glu Tyr Ile Tyr Val Asp Pro Met    555

CAG CTG CCT TAT GAC TCA AGA TGG GAG TTT CCA AGA GAT GGA CTA GTG CTT   1913
Gln Leu Pro Tyr Asp Ser Arg Trp Glu Phe Pro Arg Asp Gly Leu Val Leu    572

GGT CGG GTC TTG GGG TCT GGA GCG TTT GGG AAG GTG GTT GAA GGA ACA GCC   1964
Gly Arg Val Leu Gly Ser Gly Ala Phe Gly Lys Val Val Glu Gly Thr Ala    589

TAT GGA TTA AGC CGG TCC CAA CCT GTC ATG AAA GTT GCA GTG AAG ATG CTA   2015
Tyr Gly Leu Ser Arg Ser Gln Pro Val Met Lys Val Ala Val Lys Met Leu    606

AAA CCC ACG GCC AGA TCC AGT GAA AAA CAA GCT CTC ATG TCT GAA CTG AAG   2066
Lys Pro Thr Ala Arg Ser Ser Glu Lys Gln Ala Leu Met Ser Glu Leu Lys    623
```

TABLE 3-continued

Sequence of a human type A
PDGF receptor polypeptide allele and protein

```
ATA ATG ACT CAC CTG GGG CCA CAT TTG AAC ATT GTA AAC TTG CTG GGA GCC  2117
Ile Met Thr His Leu Gly Pro His Leu Asn Ile Val Asn Leu Leu Gly Ala   640

TGC ACC AAG TCA GGC CCC ATT TAC ATC ATC ACA GAG TAT TGC TTC TAT GGA  2168
Cys Thr Lys Ser Gly Pro Ile Tyr Ile Ile Thr Glu Tyr Cys Phe Tyr Gly   657

GAT TTG GTC AAC TAT TTG CAT AAG AAT AGG GAT AGC TTC CTG AGC CAC CAC  2219
Asp Leu Val Asn Tyr Leu His Lys Asn Arg Asp Ser Phe Leu Ser His His   674

CCA GAG AAG CCA AAG AAA GAG CTG GAT ATC TTT GGA TTG AAC CCT GCT GAT  2270
Pro Glu Lys Pro Lys Lys Glu Leu Asp Ile Phe Gly Leu Asn Pro Ala Asp   691

GAA AGC ACA CGG AGC TAT GTT ATT TTA TCT TTT GAA AAC AAT GGT GAC TAC  2321
Glu Ser Thr Arg Ser Tyr Val Ile Leu Ser Phe Glu Asn Asn Gly Asp Tyr   708

ATG GAC ATG AAG CAG GCT GAT ACT ACA CAG TAT GTC CCC ATG CTA GAA AGG  2372
Met Asp Met Lys Gln Ala Asp Thr Thr Gln Tyr Val Pro Met Leu Glu Arg   725

AAA GAG GTT TCT AAA TAT TCC GAC ATC CAG AGA TCA CTC TAT GAT CGT CCA  2423
Lys Glu Val Ser Lys Tyr Ser Asp Ile Gln Arg Ser Leu Tyr Asp Arg Pro   742

GCC TCA TAT AAG AAG AAA TCT ATG TTA GAC TCA GAA GTC AAA AAC CTC CTT  2474
Ala Ser Tyr Lys Lys Lys Ser Met Leu Asp Ser Glu Val Lys Asn Leu Leu   759

TCA GAT GAT AAC TCA GAA GGC CTT ACT TTA TTG GAT TTG TTG AGC TTC ACC  2525
Ser Asp Asp Asn Ser Glu Gly Leu Thr Leu Leu Asp Leu Leu Ser Phe Thr   776

TAT CAA GTT GCC CGA GGA ATG GAG TTT TTG GCT TCA AAA AAT TGT GTC CAC  2576
Tyr Gln Val Ala Arg Gly Met Glu Phe Leu Ala Ser Lys Asn Cys Val His   793

CGT GAT CTG GCT GCT CGC AAC GTT CTC CTG GCA CAA GGA AAA ATT GTG AAG  2627
Arg Asp Leu Ala Ala Arg Asn Val Leu Leu Ala Gln Gly Lys Ile Val Lys   810

ATC TGT GAC TTT GGC CTG GCC AGA GAC ATC ATG CAT GAT TCG AAC TAT GTG  2678
Ile Cys Asp Phe Gly Leu Ala Arg Asp Ile Met His Asp Ser Asn Tyr Val   827

TCG AAA GGC AGT ACC TTT CTG CCC GTG AAG TGG ATG GCT CCT GAG AGC ATC  2729
Ser Lys Gly Ser Thr Phe Leu Pro Val Lys Trp Met Ala Pro Glu Ser Ile   844

TTT GAC AAC CTC TAC ACC ACA CTG AGT GAT GTC TGG TCT TAT GGC ATT CTG  2780
Phe Asp Asn Leu Tyr Thr Thr Leu Ser Asp Val Trp Ser Tyr Gly Ile Leu   861

CTC TGG GAG ATC TTT TCC CTT GGT GGC ACC CCT TAC CCC GGC ATG ATG GTG  2831
Leu Trp Glu Ile Phe Ser Leu Gly Gly Thr Pro Tyr Pro Gly Met Met Val   878

GAT TCT ACT TTC TAC AAT AAG ATC AAG AGT GGG TAC CGG ATG GCC AAG CCT  2882
Asp Ser Thr Phe Tyr Asn Lys Ile Lys Ser Gly Tyr Arg Met Ala Lys Pro   895

GAC CAC GCT ACC AGT GAA GTC TAC GAG ATC ATG GTG AAA TGC TGG AAC AGT  2933
Asp His Ala Thr Ser Glu Val Tyr Glu Ile Met Val Lys Cys Trp Asn Ser   912

GAG CCG GAG AAG AGA CCC TCC TTT TAC CAC CTG AGT GAG ATT GTG GAG AAT  2984
Glu Pro Glu Lys Arg Pro Ser Phe Tyr His Leu Ser Glu Ile Val Glu Asn   929

CTG CTG CCT GGA CAA TAT AAA AAG AGT TAT GAA AAA ATT CAC CTG GAC TTC  3035
Leu Leu Pro Gly Gln Tyr Lys Lys Ser Tyr Glu Lys Ile His Leu Asp Phe   946

CTG AAG AGT GAC CAT CCT GCT GTG GCA CGC ATG CGT GTG GAC TCA GAC AAT  3086
Leu Lys Ser Asp His Pro Ala Val Ala Arg Met Arg Val Asp Ser Asp Asn   963

GCA TAC ATT GGT GTC ACC TAC AAA AAC GAG GAA GAC AAG CTG AAG GAC TGG  3137
Ala Tyr Ile Gly Val Thr Tyr Lys Asn Glu Glu Asp Lys Leu Lys Asp Trp   980

GAG GGT GGT CTG GAT GAG CAG AGA CTG AGC GCT GAC AGT GGC TAC ATC ATT  3188
Glu Gly Gly Leu Asp Glu Gln Arg Leu Ser Ala Asp Ser Gly Tyr Ile Ile   997

CCT CTG CCT GAC ATT GAC CCT GTC CCT GAG GAG GAG GAC CTG GGC AAG AGG  3239
Pro Leu Pro Asp Ile Asp Pro Val Pro Glu Glu Glu Asp Leu Gly Lys Arg  1014

AAC AGA CAC AGC TCG CAG ACC TCT GAA GAG AGT GCC ATT GAG ACG GGT TCC  3290
Asn Arg His Ser Ser Gln Thr Ser Glu Glu Ser Ala Ile Glu Thr Gly Ser  1031

AGC AGT TCC ACC TTC ATC AAG AGA GAG GAC GAG ACC ATT GAA GAC ATC GAC  3341
Ser Ser Ser Thr Phe Ile Lys Arg Glu Asp Glu Thr Ile Glu Asp Ile Asp  1048
```

TABLE 3-continued

Sequence of a human type A
PDGF receptor polypeptide allele and protein

| | | |
|---|---|---|
| ATG ATG GAC GAC ATC GGC ATA GAC TCT TCA GAC CTG GTG GAA GAC AGC TTC | 3392 |
| Met Met Asp Asp Ile Gly Ile Asp Ser Ser Asp Leu Val Glu Asp Ser Phe | 1065 |
| CTG TAACTGGCGGATTCGAGGGGTTCCTTCCACTTCTGGGGCCACCTCTGGATCCCGTTCAGAAAA | 3458 |
| Leu | 1066 |
| CCACTTTATTGCAATGCGGAGGTTGAGAGGAGGACTTGGTTGATGTTTAAAGAGAAGTTCCCAGCCA | 3525 |
| AGGGCCTCGGGGAGCCTTTCTAAATATGAATGAATGGGATATTTTGAAATGAACTTTGTCAGTGTTG | 3592 |
| CCTCTTGCAATGCCTCAGTAGCATCTCAGTGGTGTGTGAAGTTTGGAGATAGATGGATAAGGGAATA | 3659 |
| ATAGGCCACAGAAGGTGAACTTTCTGCTTCAAGGACATTGGTGAGAGTCCAACAGACACAATTTATA | 3726 |
| CTGCGACAGAACTTCAGCATTGTAATTATGTAAATAACTCTAACCACGGCTGTGTTTAGATTGTATT | 3793 |
| AACTATCTTCTTTGGACTTCTGAAGAGACCACTCAATCCATCCATGTACTTCCCTCTTGAAACCTGA | 3860 |
| TGTCAGCTGCTGTTGAACTTTTTAAAGAAGTGCATGAAAAACCATTTTTGACCTTAAAAGGTACTGG | 3927 |
| TACTATAGCATTTTGCTATCTTTTTTAGTGTTAAAGAGATAAAGAATAATAATTAACCAACCTTGTT | 3994 |
| TAATAGATTTGGGTCATTTAGAAGCCTGACAACTCATTTTCATATTGTAATCTATGTTTATAATACT | 4061 |
| ACTACTGTTATCAGTAATGCTAAATGTGTAATAATGTAACATGATTTCCCTCCACACAAAGCACAAT | 4128 |
| TTAAAAACAATCCTTACTAAGTAGGTGATGAGTTTGACAGTTTTTGACATTTATATTAAATAACATG | 4195 |
| TTTCTCTATAAAGTATGGTAATAGCTTTAGTGAATTAAATTTAGTTGAGCATAGAGAACAAAGTAAA | 4262 |
| AGTAGTGTTGTCCAGGAAGTCAGAATTTTTAACTGTACTGAATAGGTTCCCCAATCCATCGTATTAA | 4329 |
| AAAACAATTAACTGCCCTCTGAAATAATGGGATTAGAAACAAACAAAACTCTTAAGTCCTAAAAGTT | 4396 |
| CTCAATGTAGAGGCATAAACCTGTGCTGAACATAACTTCTCATGTATATTACCCAATGGAAAATATA | 4463 |
| ATGATCAGCGCANAAAGACTGGATTTGCAGAAGTTNTTTTTTTTTTCTTCTTGCCTGATGAAAGC | 4530 |
| TTTGGCGACCCCAATATATGTATTTTTTGAATCTATGAACCTGAAAAGGGTCACAAAGGATGCCCAG | 4597 |
| ACATCAGCCTCCTTCTTTCACCCCTTACCCCAAAGAGAAAGAGTTTGAAACTCGAGACCATAAAGAT | 4664 |
| ATTCTTTAGTGGAGGCTGGAAGTGCATTAGCCTGATCCTCAGTTCTCAAATGTGTGTGGCAGCCAGG | 4731 |
| TAGACTAGTACCTGGGTTTCCATCCTTGAGATTCTGAAGTATGAAGTCTGAGGGAAACCAGAGTCTG | 4798 |
| TATTTTTCTAAACTCCCTGGCTGTTCTGATCGGCCAGGTTTCGGAAACACTGACTTAGGTTTCAGGA | 4865 |
| AGTTGCCATGGGAAACAAATAATTTGAACTTTGGAACAGGGTTCTTAAGTTGGTGCGTCCTTCGGAT | 4932 |
| GATAAATTTAGGAACCGAAGTCCAATCACTGTAAATTACGGTAGATCGATCGTTAACGCTGGAATTA | 4999 |
| AATTGAAAGGTCAGAATCGACTCCGACTCTTTCGATTTCAAACCAAAACTGTCCAAAAGGTTTTCAT | 5066 |
| TTCTACGATGAAGGGTGACATACCCCCTCTAACTTGAAAGGGGCAGAGGGCAGAAGAGCGGAGGGTG | 5133 |
| AGGTATGGGCGGTTCCTTTCCGTACATGTTTTTAATACGTTAAGTCACAAGGTTCAGAGACACATT | 5200 |
| GGTCGAGTCACAAAACCACCTTTTTTGTAAAATTCAAAATGACTATTAAACTCCAATCTACCCTCCT | 5267 |
| ACTTAACAGTGTAGATAGGTGTGACAGTTTGTCCAACCACACCCAAGTAACCGTAAGAAACGTTATG | 5334 |
| ACGAATTAACGACTATGGTATACTTACTTTGTACCCGACACTAATGACGTTAGTGACACGATAGCCG | 5401 |
| TCTACTACGAAACCTTCTACGTCTTCGTTATTATTTCATGAACTGATGGATGACCACATTAGAGTTA | 5468 |
| CGTTCGGGGTTGAAAGAATAGGTTGAAAAAGTATCATTCACGCTTCTGACTCGGTCTAACCGGTTAA | 5535 |
| TTTTTCTTTTGGACTGATCCAAGACATCTCGGTTAATCTGAACTTTATGCAAACACAAAGATCTTAG | 5602 |
| TGTCGAGTTCGTAAGACAAATAGCGAGTGAGAGGGAACATGTCGGAATAAAACAACCACGAAACGTA | 5669 |
| AAACTATAACGACACTCGGAACGTACTGTAGTACTCCGGCCTACTTTGAAGAGTCAGGTCGTCAAAG | 5736 |
| GTCAGGATTGTTTACGAGGGTGGACTTAAACATATACTGACGTAAACACCCACACACACACAAAAGT | 5803 |

TABLE 3-continued

Sequence of a human type A PDGF receptor polypeptide allele and protein

| | |
|---|---|
| CGTTTAAGGTCTAAACAAAGGAAAACCGGAGGACGTTTCAGAGGTCTTCTTTTAAACGGTTAGAAAG | 5870 |
| GATGAAAGATAAAAATACTACTGTTAGTTTCGGCCGGACTCTTTGTGATAAACACTGAAAAATTTGC | 5937 |
| TAATCACTACAGGAATTTTACACCAGACGGTTAGACATGTTTTACCAGGATAAAAACACTTCTCCCT | 6004 |
| GTATTCTATTTTACTACAATATGTAGTTATACATATATACATAAAGATATATCTGAACCTCTTATGA | 6071 |
| CGGTTTTGTAAATACTGTTCGACATAGTGACGGAAGCAAATATAAAAAAATTGACACTATTAGGGGT | 6138 |
| GTCCGTGTAATTGACAACGTGAAAACTTACAGGTTTTAAATATAAAATCTTTATTATTTTTCTTTCT | 6205 |
| ATGAATGTACAAGGGTTTTGTTACCACACCACTTACACACTCTTTTTGATTGAACTATCCCAGATGG | 6272 |
| TTATGTTTTACATAATGCTTACGGGGACAAGTACAAAAACAAAATTTTGCACATTTACTTCTAGAAA | 6339 |
| TATAAAGTTATTTACTATATATTAAATTTCCTTAAG | 6375 |

ˆz

As seen in Tables 2 and 3, the presumed intracellular tyrosine kinase domain of the type A and type B receptors have about 80% identical residues. The putative extracellular regions of the type A and B receptors have about 34–35% identical residues, an additional 14% of the remaining residues being conservative substitutions, i.e., substitutions with amino acids having similar chemical properties. The designated transmembrane regions of the hPDGF receptors have about 48% identical residues. Of the 52% of residues that differ, 70% are conservative substitutions. As seen in the tables, both receptor sequences have an amino acid insertion of about 103 or 104 amino acids interrupting the putative tyrosine kinase region. The overall homology between the two polypeptide sequences is about 44%.

The term platelet-derived growth factor receptor (PDGF-R) refers to a composition having properties characteristic of a PDGF-R. The native human PDGF receptors are examples of the class of PDGF-Rs, as are each of the polypeptides whose sequences are disclosed in Tables 2 and 3, and allelic variants. The natural receptor is typically a membrane glycoprotein having a molecular weight of about 180 kd. The receptor is normally found in vascular smooth muscle cell, fibroblasts, and glial cells, but not commonly observed in endothelial cells or on most hematopoietic cells.

As indicated above, the PDGF receptors have three major identifiable regions. The first is an extracellular region which contains the ligand binding determinants for the PDGF, i.e., the ligand binding segments. The extracellular region is also divided into Ig-like domains with the characteristics described above. The second major identifiable region is a transmembrane region and the third is an intracellular region. The intracellular region contains a characteristic type of tyrosine kinase domain, interrupted by a kinase insert (KI) segment.

The description "human" refers to the origin of the composition. In one use, it implies that the composition was found, at one point, within a human or human-derived cell or a minor variant from a naturally occurring human cell. With respect to a protein or nucleic acid or sequence, it refers to a composition encoded by a natural human gene, or a closely related gene. Thus, the present invention includes proteins and nucleic acids encoding such proteins. The nucleic acids include RNA, cDNA, genomic DNA, synthetic forms, and mixed polymers, both sense and antisense strands. Thus, a protein derived from the sequence information disclosed, even if made synthetically, would be considered a human sequence. Furthermore, different alleles of each isoform are each also considered a human PDGF-R.

Thus, for the purposes used herein, the term human PDGF-R, when applied to a polypeptide, means a protein or polypeptide, which is substantially homologous to the amino acid sequences depicted in Table 2 or 3 and any alleles of them, or a fragment thereof. Ordinarily, hPDGF-R's will be at least about 80 percent homologous to the described PDGF-R sequences, preferably in excess of about 90 percent homology, and, more preferably, at least about 95 percent homology. The receptor will ordinarily also exhibit at least some biological activity in common with a hPDGF-R provided in the relevant sequences, e.g., PDGF binding, tyrosine kinase activity, phosphatidylinositol 3' kinase (PI3 kinase) binding, or immunologic properties. The hPDGF receptor embraces forms of the molecule which share the primary structural sequence, and is intended to encompass chemical and biochemical modifications, e.g., glycosylation, phosphorylation, ubiquinization, disulfide bonds, and other minor alterations in the basic primary sequence.

In particular, glycosylation alterations are included, made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Also embraced are versions of the same primary amino acid sequence which have phosphorylated amino acid residues, e.g., phosphotyrosine, phosphoserine, or phosphothreonine.

The type B hPDGF-R is an isotype of a hPDGF-R polypeptide whose properties have been described above, and includes all alleles of that sequence and minor modified sequences derived therefrom. Generally, the term also is intended to include fragments of the protein, particularly those which are characteristic of the human type B isoform. Corresponding meaning is intended in reference to the type A hPDGF-R.

In certain uses, the term applies to the functional receptor. As described, the functional form is believed to be a dimer complex of the type A receptor polypeptide, or of the type B receptor polypeptide, or the heterodimer form.

A heterologous fusion protein is a fusion of proteins or segments which are naturally not normally fused in the same manner. Thus, the fusion product of an immunoglobulin with a hPDGF-R polypeptide is a continuous protein molecule having sequences fused in a typical peptide linkage, typically made as a single translation product and exhibiting both immunoglobulin and hPDGF-R polypeptide dependent properties. A similar concept applies to heterologous nucleic acid sequences.

A polypeptide fragment, or segment, is a stretch of amino acid residues of at least about 5 amino acids, often at least about 7 amino acids, usually at least about 9 amino acids, more usually at least about 11 amino acids, typically at least about 13 amino acids, more typically at least about 15 amino acids, and, in various embodiments, at least about 17 or more amino acids. In a nucleic acid, a fragment or segment is a stretch of at least about 6 nucleotides, often at least about 9 nucleotides, usually at least about 12 nucleotides, more usually at least about 15 nucleotides, typically at least about 18 nucleotides, more typically at least about 21 nucleotides, and in various preferred embodiments, at least about 24 or more nucleotides.

A polypeptide fragment is "physiologically active" when it substantially contributes to an activity characteristic of a natural polypeptide or fragment, e.g., a PDGF-R polypeptide. Typically, a hPDGF-R polypeptide, when associated into a functional receptor, has the set of activities performed by the receptor in a biological context (e.g., in an organism or an in vitro biological context). In the case of the hPDGF-R, a functional fragment has these physiological activities, or functional activities characteristic of a hPDGF receptor, which include PDGF binding, tyrosine kinase activity and any of the mitogenic or other cellular responses mediated by the receptor. However, the protein fragment may exhibit other specific or inherent functions, such as vital conformational constraints, serving as a substrate site for glycosylation, contributing the signal sequence for cellular targeting, presenting characteristic epitopes absent in a mouse PDGF-R, or presently unrecognized functions possessed inherently.

Solubility of a polypeptide depends upon the environment and the polypeptide. Many parameters affect polypeptide solubility, including the temperature, the electrolyte environment, the size and molecular characteristics of the polypeptide, and the nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified to conform to standard buffers used in physiological or analytical contexts.

The size and structure of the polypeptide should generally be in a substantially stable and globular state, and usually not in a denatured state. The polypeptide may be associated with other polypeptides in a quaternary structure, e.g., to confer solubility.

The solvent will usually be a biologically compatible buffer, of a type used for preservation of biological activities, and will usually approximate a physiological solvent. On some occasions, a detergent will be added, typically a mild non-denaturing one.

Solubility is usually measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman, and Cantor and Schimmel (1980) *Biophysical Chemistry*, parts 1–3, W. H. Freeman & Co., San Francisco, each of which is hereby incorporated herein by reference. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S.

The PDGF receptors or the specific extracellular regions of the receptors as provided herein may be used to affinity purify respective PDGFs. The full length, or entire, extracellular region, comprises the ligand-binding determinants of the type B receptor in Table 2, and extends from about leu(1) to lys(499). The full length, or entire, extracellular region comprising the ligand-binding determinants of the type A hPDGF-R shown in Table 3 extends from about gln(1) to glu(501). The ligand-binding determinants vary with different PDGF receptor alleles and may be anywhere from 5% to all of the extracellular region. The minimal amount of protein sequence essential for ligand binding may be determined by excising various segments of the extracellular region and measuring ligand binding. Studies of ligand-receptor interaction indicate that the ligand-binding region is located in the extracellular region of the receptor. More sophisticated studies on the effects of various residues on the specificity of ligand binding are also made possible by the reagents of this invention. As used in this application, PDGF receptor or PDGF-R ligand-binding activity means having the ability to bind a PDGF, a PDGF agonist or antagonist, or other specific ligand for a hPDGF receptor. Usually these ligands will be members of the PDGF family, typically a human form. Therefore the external region has utility in establishing whether an analogue is a PDGF agonist or antagonist.

It is also likely that the PDGF-R, like many other growth factor receptors, is found naturally in a multimeric protein complex, most likely in dimer form. Thus, other important regions of a receptor will be those segments, either extracellular or otherwise, which are involved in dimerization or protein-protein interaction.

Besides substantially full-length polypeptides, the present invention provides for biologically active fragments of the polypeptides, or analogues thereof, including organic molecules which simulate the interactions of the peptides. Significant biological activities include ligand-binding, immunological properties, dimer association, serving as a kinase substrate, interacting with other mediators specific for binding to a PDGF-R protein, and other biological activities characteristic of human PDGF receptor polypeptides. Immunological activities include both immunogenic function in a target immune system, sharing of immunological epitopes for binding, and serving as either a competitor or substitute antigen for a human PDGF receptor epitope. Assays for these immunological activities are known in the art, see, e.g., below in the Experimental section; Harlow and Lane (1989) *Antibodies: A Laboratory Manual,* Cold Spring Harbor Press, New York; and Escobedo et al. (1988) *J. Biol. Chem.* 263:1482–1487, which are each hereby incorporated herein by reference. For example, ligand-binding or other segments may be "swapped" between different new fusion polypeptides or fragments. Thus, new chimeric polypeptides exhibiting new combinations of specificities will result from the functional linkage of ligand-binding specificities and intracellular regions. For example, the Ig domains from other related polypeptides may be added or substituted for other Ig-like domains of these receptors. The resulting protein will often have hybrid function and properties.

For immunological purposes, immunogens may be produced which tandemly repeat polypeptide segments, thereby producing highly antigenic proteins. Alternatively, such polypeptides will serve as highly efficient competitors for specific binding. Production of antibodies to hPDGF receptor polypeptides is described below.

The present invention also provides for other polypeptides comprising fragments of PDGF receptors and polypeptides substantially homologous thereto. The receptor peptides of the present invention will generally exhibit at least about 80% homology with naturally occurring sequences of hPDGF receptor, typically at least about 85% homology with a natural receptor sequence, more typically at least about 90% homology, usually at least about 95% homology, and more usually at least about 97% homology. The length of comparison sequences will generally be at least about 16 amino acids, usually at least about 20 residues, more usually at least about 24 residues, typically at least about 28 residues, and preferably more than about 35 residues.

Homology, for polypeptides, is typically measured using sequence analysis software, see, e.g., Sequence Analysis Software Package of the Genetics Computer Group, University of Wisconsin Biotechnology Center, 1710 University Avenue, Madison, Wis. 53705. Protein analysis software matches similar sequences using measure of homology assigned to various substitutions, deletions, substitutions, and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

Fusion polypeptides between the receptors and other homologous or heterologous proteins are also provided. Homologous polypeptides may be fusions between different growth factor receptors, resulting in, for instance, a hybrid protein exhibiting ligand specificity of one receptor and the intracellular region of another, or a receptor which may have broadened or weakened specificity of binding. Likewise, heterologous fusions may be constructed which would exhibit a combination of properties or activities of the derivative proteins. Typical examples are fusions of a reporter polypeptide, e.g., luciferase, with a segment or domain of a receptor, e.g., a ligand-binding segment, so that the presence or location of a desired ligand may be easily determined. See, e.g., Dull et al., U.S. Pat. No. 4,859,609, which is hereby incorporated herein by reference. Other gene fusion partners include bacterial β-galactosidase, trpE, Protein A, β-lactamase, alpha amylase, alcohol dehydrogenase, and yeast alpha mating factor. See, e.g., Godowski et al. (1988) *Science* 241:812–816.

Such polypeptides may also have amino acid residues which have been chemically modified by phosphorylation, sulfonation, biotinylation, or the addition of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation are described generally, for example, in Sambrook et al. (1989), *Molecular Cloning: A Laboratory Manual* (2d ed.), Vols. 1–3, Cold Spring Harbor Laboratory, which are incorporated hereby by reference. Techniques for synthesis of polypeptides are described, for example, in Merrifield (1963) *J. Amer. Chem. Soc.* 85:2149–2156; Merrifield (1986) *Science* 232: 341–347; and Atherton et al. (1989) *Solid Phase Peptide Synthesis: A Practical Approach,* IRL Press, Oxford; each of which is incorporated herein by reference.

Fragments of an intact receptor are also embraced herein. Various fragments include the transmembrane segment, which confers a cell surface attachment function. Various fragments deleting either intracellular or extracellular segments will be produced. For example, fragments comprising a transmembrane segment, either of a PDGF receptor or another protein, in combination with ligand binding determinants, will provide membrane associated ligand binding regions. Similar constructs with intracellular regions may be prepared, producing, e.g., membrane associated tyrosine kinase segments.

In particular, soluble fragments comprising ligand binding determinants will be produced which may be used for absorbing free ligand. The soluble fragments can be used for diagnostic and therapeutic purposes to block PDGF mediated responses.

In another embodiment, intracellular fragments and analogues will be prepared. The kinase insert region (KI) within the tyrosine kinase domains is a particularly useful fragment, as described below.

A peptide analogue of a phosphorylated region of a protein is a peptide with substantial primary sequence homology to a phosphorylated region of another protein, and having at least one phosphorylated or similarly derivatized residue at positions corresponding to the position of similar phosphorylated residues in the phosphorylated region of that other protein. Where such a region has two or more phosphorylated residues, peptide analogues will, in certain embodiments, have only one such phosphorylated or similarily derivatized residue. Such phosphorylated residues will generally include phosphotyrosine, phosphoserine, or phosphothreonine. The peptide analogue will sometimes have one or more unnatural amino acids, including, e.g., residues chemically modified by biotinylation, phosphorylation, sulfonation, or glycosylation. It will generally be in monomer form or a multimer of repeated peptide units, and often will be joined to heterologous proteins or peptide fragments. Such heterologous proteins or peptides will often include segments derived from various proteins, e.g., immunoglobulins, β-galactosidase, β-glucuronidase, luciferase, trpE, or Protein A. See, e.g., Godowski et al. (1988) *Science* 241: 812–816. Such peptide analogues will generally be soluble or coupled to a solid phase support, e.g., nitrocellulose, nylon, column packing materials (e.g., Sepharose beads), magnetic beads, glass wool, cells, or other substrates.

A phosphorylated region of a protein important for normal protein function will often be identified by a number of approaches, e.g., analysis of mutated proteins that have deletions or point mutations resulting in a change of ability to bind to another protein, altered enzymatic activity, or modification of other protein characteristics. Methods well known to those in the art are available to determine whether a peptide region is phosphorylated in vivo. See, e.g., Kazlauskas and Cooper (1989) *Cell* 58: 1121–1133; Williams (1989) *Science* 243: 1564–1570; and Wahl et al. (1990) *J. Biol Chem.* 265: 3944. Direct structural determination, e.g., x-ray crystallographic or 2D-NMR, can be used to determine locations of interactions, which guide where modifications are likely to affect interactions, both ligand and effector binding activities.

Fragments, in various extracellular region and intracellular region embodiments, will generally be at least about 1200 daltons, often be at least about 2400 daltons, typically at least about 3000 daltons, more typically at least about 3600 daltons, and in some preferred embodiments, at least about 4200 daltons or more.

III. Nucleic Acids

The nucleic acid compositions of this invention will generally be in RNA or DNA forms, or even a mixed polymer. The described DNA embodiment is usually derived from genomic DNA or cDNA, prepared by synthesis, or derived from combinations thereof. The DNA compositions generally include the complete coding region encoding hPDGF-R or fragments thereof, e.g., comprising at least 8 codons (24 bp), usually at least 12 codons, more usually at least about 15 codons, typically at least about 20 codons, more typically at least about 30 codons and preferably even more. One or more introns may be present.

The term hPDGF-R, when loosely applied to a nucleic acid, refers to a nucleic acid which encodes a hPDGF-R polypeptide, fragment, or variant, including protein fusions or deletion variants. A nucleic acid encodes a polypeptide when a corresponding message of a sequence, or its complement, is translated, as-provided by a universal code of nucleotide triplets into polypeptide primary structure.

An "isolated" nucleic acid is a nucleic acid, e.g., an RNA, DNA, or a mixed polymer, which is substantially separated from other DNA sequences which naturally accompany a native human sequence, e.g., ribosomes, polymerases, and many other human genome sequences. The term embraces a nucleic acid sequence which has been removed from its naturally occurring environment, and includes recombinant or cloned DNA isolates and chemically synthesized analogues or analogues biologically synthesized by heterologous systems. A substantially pure molecule includes isolated forms of the molecule.

An isolated nucleic acid will generally be a homogenous composition of molecules, but will, in some embodiments, contain minor heterogeneity. This heterogeneity is typically found at the polymer ends or portions not critical to a desired biological function or activity.

The term "encoding" refers generally to the sequence information being present in a translatable form, usually operably linked to a promoter. A sequence is operably linked to a promoter when the functional promoter enhances transcription or expression of that sequence. An anti-sense strand is considered to also encode the sequence, since the same informational content is present in a readily accessible form, especially when linked to a sequence which promotes expression of the sense strand. The information is convertible using the standard, or a modified, genetic code. See, e.g., Watson et al. (1987) *The Molecular Biology of the Gene* (4th ed.) vols. 1&2, Benjamin, Menlo Park, Calif.

The term "recombinant" refers to a nucleic acid sequence which is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the common natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide.

Homologous sequences, when compared, exhibit similarity. The standards for homology in nucleic acids are either measures for homology generally used in the art or hybridization conditions. The hybridization conditions are described below, but are further limited by the homology between the corresponding human and mouse segments. Homology will be limited, in addition to any stated parameters, by any similarity between the human and mouse sequences such that the stated homology specifically is limited by the conditions which are sufficient for the corresponding mouse segment of the segment being compared to match the stated human segment.

Substantial homology in the nucleic acid context means either that the segments, or their complementary strands, when compared, are identical when optimally aligned, with appropriate nucleotide insertions or deletions, in at least about 60% of the residues, usually at least about 70%, more usually at least about 80%, preferably at least about 90%, and more preferably at least about 95 to 98% of the nucleotides. Alternatively, substantial homology exists when the segments will hybridize under selective hybridization conditions, to a strand, or its complement, typically using a sequence derived from Table 2 or 3. Selectivity of hybridization exists when hybridization occurs which is more selective than total lack of specificity. Typically, selective hybridization will occur when there is at least about 55% homology over a stretch of at least about 14 nucleotides, preferably at least about 65%, more preferably at least about 75%, and most preferably at least about 90%. See, Kanehisa (1984) *Nuc. Acids Res.* 12:203–213, which is incorporated herein by reference. The length of homology comparison, as described, may be over longer stretches, and in certain embodiments will often be over a stretch of at least about 17 nucleotides, usually at least about 20 nucleotides, more usually at least about 24 nucleotides, typically at least about 28 nucleotides, more typically at least about 32 nucleotides, and preferably at least about 36 or more nucleotides.

Stringent conditions, in referring to homology, will be stringent combined conditions of salt, temperature, organic solvents, and other parameters typically controlled in hybridization reactions. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter.

See, e.g., Wetmur and Davidson (1968) *J. Mol. Biol.* 31:349–370, which is hereby incorporated herein by reference.

While the wild-type sequences of these alleles will generally be employed, in some situations one or more mutations or minor modifications may be introduced, such as deletions, substitutions or insertions resulting in changes in the amino acid sequence, providing silent mutations or modifying amino acid residues or amino or carboxyl terminal groups. There will be circumstances where gene fusions between a hPDGF-R and another protein can be useful, or a fusion between the separate types A and B forms. The nucleic acid sequence, usually genomic, will often not exceed about 50 kb, more often will not exceed about 40 kb, typically will not exceed about 30 kb, more typically will not exceed about 20 kb, usually will not exceed about 10 kb, and in various embodiments, preferably will not exceed about 6 kbp. Such sequences may have any or all introns removed.

A DNA fragment encoding hPDGF-R finds use to isolate DNA encoding PDGF receptors of other species which share substantial homologies with hPDGF-R. Fragments from the intracellular tyrosine kinase region can be used to isolate other tyrosine kinases. Portions of the DNA fragment having at least about 10 nucleotides, usually at least about 20 nucleotides, more usually at least about 30 nucleotides, and fewer than about 6 knt (kilonucleotides), usually fewer than about 0.5 knt, from a DNA sequence encoding a hPDGF-R find use as probes. The probes can be used to determine whether RNA encoding a hPDGF-R or a fragment thereof is present in a cell.

Additionally, the type B human PDGF receptor-gene is located at a site on chromosome 5 where a number of growth control related genes are clustered. At least one genetic disease, 5q minus syndrome, has been shown to involve a deletion in this region. The type A receptor gene is located on chromosome 4 near the c-kit proto-oncogene. These sequences, often intact genes, will find use in diagnosing the integrity of these chromosomal regions. Fragments of hPDGF-R gene sequences will often be used as markers to probe the structure of these important regions of the genome and to diagnose genetic diseases associated with those areas of the genome. Alternatively, the sequences are useful to isolate other fragments for testing the integrity of the chromosome regions.

The recombinant nucleic acid sequences used to produce fusion proteins of the present invention will often be derived from natural or synthetic sequences. Many natural gene sequences are obtainable from various libraries, cDNA or genomic, using appropriate probes. See, GenBank™, National Institutes of Health. Typical probes for human PDGF receptors will be selected from the sequences of Table 2 or 3 in accordance with standard procedures, or from alleles of them. The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

IV. Methods for Making PDGF Receptor and Fragments

The novel nucleic acids provided herein are useful for making PDGF receptor. The DNA fragment or portions thereof will be used to prepare an expression construct for a hPDGF-R. The expression construct normally comprises one or more DNA sequences encoding a hPDGF-R under the transcriptional control of a native or other promoter. When more than one sequence encoding hPDGF-R is present in the construct, the sequences will encode the same or different forms of the receptor, usually different. Usually the promoter will be a eukaryotic promoter for expression in a mammalian cell, where the mammalian cell may or may not lack PDGF receptors. The transcriptional regulatory sequences will typically include a heterologous enhancer or promoter which is recognized by the host. The selection of an appropriate promoter will depend upon the host, but promoters such as the trp, lac and phage promoters, tRNA promoters and glycolytic enzyme promoters are known. See, e.g., Sambrook et al. (1989). Conveniently available expression vectors which include the replication system and transcriptional and translational regulatory sequences together with the insertion site for the fibroblast growth factor receptor DNA sequence may be employed. Examples of workable combinations of cell lines and expression vectors are described in Sambrook et al. (1989); see also, Metzger et al. (1988), *Nature* 334:31–36, each of which is hereby incorporated herein by reference. In particular, non-fungal promoters will be preferred where expression occurs in non-fungal cells. Occasionally, it might be useful to express the sequences in other types of cells, and appropriate promoters may be selected. And in some circumstances, an inducible promoter may be preferred. In other circumstances, it will be desired to coexpress a glycosylation enzyme which will provide a glycosylation pattern similar to that provided by a different cell type.

In cases where one wishes to expand the DNA sequence or produce the receptor protein or fragments thereof in a prokaryotic host, a preferred promoter is a prokaryotic promoter, e.g., trp, lac, and lambda, and see Sambrook et al. (1989) for other useful prokaryotic promoters. Usually a strong promoter will be employed to provide for high level transcription and expression.

The expression construct will often be contained in a vector capable of stable extrachromosomal maintenance in an appropriate cellular host or may be integrated into the host genome. The expression construct may be bordered by sequences which allow for insertion into a host, such as transposon sequences, lysogenic viral sequences, or the like. Normally, markers are provided with the expression construct which allow for selection of host cells containing the construct. The marker may be on the same or a different DNA molecule, preferably on the same DNA molecule.

In mammalian cells, the receptor gene itself will often provide a convenient marker. However, in prokaryotic cells, markers such as a resistance to a cytotoxic agent, complementation of an auxotrophic host to prototrophy, production of a detectable product, etc., will be more convenient.

The expression construct can be joined to a replication system recognized by the intended host cell. Various replication systems include viral replication systems such as retroviruses, simian virus, bovine papilloma virus, or the like. In addition, the construct may be joined to an amplifiable gene, e.g., DHFR gene, so that multiple copies of the desired hPDGF-R gene may be made. See, e.g., Schimke, R. (1984) *Cell* 37:705–713; and Kaufman et al. (1985) *Mol. Cell Biol.* 5:1750–1759; each of which is hereby incorporated herein by reference.

In particular, it will often be desired to express a receptor polypeptide in a system which provides a non-fungal glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the PDGF receptor gene may be co-transformed with one or more genes encoding mammalian or other glycosylating enzymes, preferably originating from a non-fungal species, and in some embodiments, non-human species. Using this approach, certain mammalian glycosylation patterns will be achievable in prokaryote or other cells.

The means of introduction of the expression construct into a host cell will vary depending upon the particular construction and the target host. Introduction can be achieved by any convenient means, including fusion, conjugation, transfection, transduction, electroporation, injection, or the like. See, e.g., Sambrook, et al. (1989) *Molecular Cloning: A Laboratory Guide, Vols* 1–3, Cold Spring Harbor Press, which is hereby incorporated herein by reference. Introduction of constructs encoding different forms of the receptor into a single host cell is also contemplated. The host cells will normally be immortalized cells, i.e., cells that can be continuously passaged in culture. For the most part, these cells will be convenient mammalian cell lines which are able to express a hPDGF-R and, where desirable, process the polypeptide so as to provide an appropriate mature polypeptide. By processing is intended glycosylation, ubiquitination, disulfide bond formation, general post-translational modification, or the like. Usually the host will be able to recognize the signal sequence for inserting hPDGF-R into the membrane of the cell. If secretion is desired, the transmembrane sequence will generally be deleted or mutated to prevent membrane localization of the protein.

A wide variety of hosts will be employed for expression of the peptides, both prokaryotic and eukaryotic. Useful hosts include bacteria, such as *E. coli,* yeast, filamentous fungi, insect cells, mammalian cells, typically immortalized, e.g., various mouse cell lines, monkey cell lines, Chinese hamster ovary cell lines, human cell lines, derivatives of them, or the like. In some cases, the cells will be derived from a neoplastic host cell or wild-type cells will be transformed with oncogenes, tumor causing viruses or the like.

Under some circumstances, it will be desirable to transfect mammalian cells which lack a PDGF receptor, e.g., with a construct where a signal sequence and transmembrane region direct the receptor peptide to the cell membrane. Progeny of transformed or transfected cells are also intended to be encompassed. Lymphocytes and cardiac myocytes are examples of primary cells which lack a receptor. Chinese hamster ovary cells (CHO), epithelial cells lines, and a number of human tumor cell lines also lack PDGF receptors.

The compositions and cells comprising hPDGF receptors and fragments can be used for diagnostic purposes and to study and treat diseases or medical conditions associated with PDGF receptors. Use of the soluble extracellular ligand binding fragments has already been described generally. In addition, various segments of the intracellular region include phosphorylated amino acid residues. The sites of phosphorylation are important in interaction of segments with other polypeptides. The nature and specificity of the interactions are highly dependent upon the presence or absence of the phosphorylation, and fragments of the intact receptor, or related sequences, will be useful in modulating the interactions. Thus, intracellular region fragments will also find important uses.

Cells expressing cloning vehicles containing defined sequences can be used to define specific sites of a PDGF receptor necessary for effecting a particular activity. Alternatively, these cells will be useful to assess the ability of a selected receptor to bind different ligands (PDGFs and analogues) thereby providing a powerful tool for evaluating the potential of drugs for promoting or inhibiting specific PDGF-induced cellular responses.

Cells transfected, injected, infected or electroporated with DNA or mRNA containing a full length natural PDGF-R sequence will often express the native or wild type receptor and respond accordingly less than full length segments will often have desired equivalent functions. Specific concentrations of a purified receptor or a receptor polypeptide fragment can be used to block the binding of the ligand (PDGF) to native PDGF receptors. Alternatively, antibodies to the receptor or fragment can have the same effect. In particular, it has been demonstrated herein that antibodies against epitopes of the extracellular region can block ligand-receptor binding. Other antibodies will block dimerization of receptor polypeptides, and thus modulate receptor function.

Homogeneous and defined polypeptides and DNA sequences will find use in raising antibodies and defining specificity of their binding. In particular, antibodies against specific regions of the receptor, e.g., the ligand-binding segments, will find use in diagnostic testing or therapeutics. The reagents PDGF-R, PDGF-R polypeptides, and antibodies to specific regions of the receptor can be used to study regulation of PDGF mediated activities. Intracellular fragments will also have important uses, especially, e.g., the kinase insert segment.

PDGF has roles in tissue repair, embryogenesis, and likely is involved in atherosclerosis, myeloproliferative disease, and some carcinomas. Treatment of these conditions responds to attenuation by therapeutic administration of the soluble extracellular fragments or antibodies. For example, PDGF agonists stimulate cell proliferative development, an effect particularly beneficial in wound healing, muscle regeneration, and arterial wall proliferation. PDGF antagonists will be used, in some cases, to block excess response, or to modulate PDGF response.

Compositions containing a soluble PDGF-R polypeptide having between about five and two hundred, preferably about 10 or 15 to 50, contiguous amino acids from a human PDGF-R extracellular region are described. In one embodiment, the polypeptide contains at least about 80 amino acids from residues 1 to 499 of a type B human PDGF receptor of Table 2, or from residues 1 to 501 of a type A human receptor of Table 3.

In another embodiment, fragments of the intracellular region will find various uses. In particular, the KI region, and fragments or analogues thereof, will find use in blocking or modulating interaction of a phosphorylated residue with a recognition interaction, usually binding by another protein. These interactions are often important in further signal transduction and cellular responses.

The hPDGF-R protein expressed by transfected cells also finds many uses. If the peptide is secreted, the peptide will typically be isolated from the supernatant in which the expression host is grown. If not secreted, the peptide will be typically be isolated from the expression host, e.g., from a lysate. The peptide will generally be isolated by convenient techniques employing HPLC, electrophoresis, gradient centrifugation, affinity chromatography, e.g., using PDGF, column chromatography and other methods of protein purification used in protein biochemistry to provide a substantially pure product, e.g., particularly free of cell component contaminants. See, e.g., Jacoby (1984) *Methods in Enzymology*, Vol. 104, Academic Press, New York; Scopes (1987) *Protein Purification: Principles and Practice,* (2nd Ed.) Springer-Verlag, New York; Deutscher (ed.)

(1990) *Guide to Protein Purification, Methods in Enzymology*, Vol. 182; each of which is hereby incorporated herein by reference.

The receptor protein or amino acids beginning at about leu(1) through lys(499) of the amino terminal sequence of the type B receptor, and about gln(1) through glu(501) of the sequence of the type A receptor, which form the entire extracellular regions, and particularly the PDGF ligand binding portions of the receptor proteins, will find use to affinity purify PDGF. The extracellular region can also be used affixed to a solid substrate or free in solution to determine drugs useful as PDGF agonists and antagonists.

The intracellular region of the protein, beginning at about val(500) through the carboxyl terminal amino acid of the type B receptor, and about leu(502) through the carboxyl terminus of the type A receptor, also find use as tyrosine kinases for protein phosphorylatian in accordance with well known techniques. Additionally, amino acids met(−32) through gly(−1) of the amino terminal sequence of the type B receptor, and from about met(−23) through cys(−1) of the type A receptor, comprise signal sequences which direct the structural protein through the membrane of a transfected cell. These signal sequences will be used with a hPDGF-R, but also would be expected to find use with other proteins if fused to them.

Human PDGF receptor polypeptide fragments will typically be generated either by direct expression of truncated nucleic acid sequences, or by standard protease treatment of a hPDGF receptor, preferably purified. Reagents are provided herein for either approach.

As a diagnostic use, these reagents provide a method for measuring a PDGF or a PDGF receptor in a target sample, said method comprising the steps of:

combining said target sample with a hPDGF receptor polypeptide segment; and determining the extent of binding between said polypeptide segment and said sample.

This invention also provides a transformed cell, which is also includes progeny of the primary transformant, capable of expressing a polypeptide homologous to at least a segment of human PDGF receptor. A preferred embodiment is where the cell expresses a polypeptide homologous to substantially the entire extracellular region of a human PDGF receptor, including soluble proteins.

V. Antibodies

Polyclonal and/or monoclonal antibodies to the various PDGF receptors and peptide fragments may also be prepared. Synthetic peptide fragments may be prepared in a peptide synthesizer and coupled to a carrier molecule (e.g., keyhole limpet hemocyanin) and injected into rabbits at selected times over several months. The rabbit sera is tested for immunoreactivity to the PDGF receptor protein or fragment. Monoclonal antibodies may be made by injecting mice with hPDGF-R protein, hPDGF-R polypeptides or mouse cells expressing high levels of the cloned PDGF receptor on its cell surface. Monoclonal antibodies will be screened by ELISA and tested for specific immunoreactivity with the PDGF receptor protein or polypeptides thereof. See, e.g., Harlow and Lane (1988) *Antibodies: A Laboratory Manual*, Cold Spring Harbor Press, New York, which is hereby incorporated herein by reference. These antibodies will be useful in assays, or as pharmaceuticals.

Once a sufficient quantity of the desired hPDGF receptor polypeptide has been obtained, the protein will be used for various purposes. A typical use is the production of antibodies specific for binding to these receptors. These antibodies will usually be either polyclonal or monoclonal and will usually be produced by in vitro or in vivo techniques, e.g., directed towards the goal of defining or recognizing particular antigenic determinants, or epitopes. Usually the epitopes will be provided by molecular shapes of contiguous amino acid residues, but may be sequentially non-contiguous but in close spatial proximity due to secondary or tertiary structure. In particular, a polypeptide epitope homologous to a sequence of at least six contiguous amino acids described in Table 2 or Table 3 will be a useful immunogen. The epitopes of most interest will be those from a signal sediment or immunoglobulin domains found in the extracellular region, particularly those surrounding the PDGF ligand binding regions. However, other segments will also be important, including phosphorylation sites in the intracellular region, e.g., the kinase insert segment, phosphorylated or not.

For production of polyclonal antibodies, an appropriate target immune system is selected, typically a mouse or rabbit. The substantially purified antigen is presented to the immune system in a fashion determined by methods appropriate for the animal and other parameters well known to immunologists. Typical sites for injection are in the footpads, intramuscularly, intraperitoneally, or intradermally. Of course, another species will sometimes be substituted for a mouse or rabbit, including goats, sheep, cows, guinea pigs, and rats.

An immunological response is usually assayed with an immunoassay. Normally such immunoassays involve some purification of a source of antigen, for example, produced by the same cells and in the same fashion as the antigen was produced. The immunoassay will, in some instances, be a radioimmunoassay, an enzyme-linked assay (ELISA), a fluorescent assay, or any of many other choices, most of which are functionally equivalent but may exhibit advantages under specific conditions.

Monoclonal antibodies with affinities of $10^8$ $M^{-1}$ preferably $10^9$ to $10^{10}$, or stronger will typically be made by standard procedures as described, e.g., in Harlow and Lane, *Antibodies: A Laboratory Manual*, CSH Laboratory (1988); or Goding (1986) *Monoclonal Antibodies: Principles and Practice* (2d ed) Academic Press, New York; each-of which is hereby incorporated herein by reference. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter the cells are clonally separated and the supernatants of each clone are tested for their production of an appropriate antibody specific for the desired region of the antigen.

Other suitable techniques involve in vitro exposure of lymphocytes to the antigenic polypeptides or alternatively to selection of libraries of antibodies in phage or similar vectors. See, Huse et al. (1989) "Generation of a Large Combinatorial Library of the Immunoglobulin Repertoire in Phase Lambda," *Science* 246:1275–1281, which is hereby incorporated herein by reference. The polypeptides and antibodies of the present invention may be used with or without modification. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567.

Full length peptides or portions thereof will, in particular embodiments, be used for producing antibodies, either polyclonal or monoclonal. Antibodies are produced by immunizing an appropriate vertebrate host, e.g., mouse, with the peptide or fragment itself, or in conjunction with an adjuvant. Usually two or more immunizations will be involved, and the blood or spleen will be harvested a few days after the last injection.

For polyclonal antisera, the immunoglobulins may be precipitated, isolated and purified, including affinity purification. For monoclonal antibodies, the splenocytes normally will be fused with an immortalized lymphocyte, e.g., a myeloid line, under selective conditions for hybridomas. The hybridomas will generally then be cloned under limiting dilution conditions and their supernatants screened for antibodies having the desired specificity. Techniques for producing antibodies are well known in the literature, see, e.g., Goding (1986) *Monoclonal Antibodies: Principles and Practice* (2d ed.) Academic Press, N.Y., and Harlow and Lane (1988) *Antibodies: A Laboratory Manual,* Cold Spring Harbor Laboratory, New York, and are exemplified by U.S. Pat. Nos. 4,381,292, 4,451,570 and 4,618,577, which are each incorporated herein by reference. The antibodies generated therefrom may have many uses in dissecting the portions of the receptor responsible for various cellular responses and in the general processing and maturation of the receptor itself. Antibody agonists or antagonists might even be produced.

Both proteins and fragments to serve as immunogens, and as reagents to determine the specificity of binding, are provided herein.

VI. Methods for Use

The present invention provides a human platelet derived growth factor receptor (hPDGF-R) purification method as well as a method for synthesizing PDGF receptors within cells. Also provided are homogeneous receptors produced by these methods, nucleic acid sequences encoding the receptors or portions of the receptors, expression vehicles containing these sequences, cells comprising the PDGF-receptors, and antibodies to the receptors. Of particular interest are fragments of the receptors, which have functional binding sites which compete with receptors to bind particular ligands. See, e.g., Orchansky et al. (1988) "Phosphatidylinositol Linkage of a Truncated Form of the Platelet-derived Growth Factor Receptor" *J. Biol. Chem.* 263:15159–15165, which provides evidence that an extracellular region of the PDGF receptor can bind to the PDGF ligands. Also provided are phosphorylated fragments or sites for phosphorylation which interact with other proteins important in cellular response to ligand binding. In particular, soluble extracellular region segments are provided.

Transfected cells find use as a model for studying cellular responses to PDGF. For controlled investigation, mammalian cells which lack a PDGF receptor can be transfected with an expression construct comprising a DNA sequence encoding a hPDGF-R. Cells are produced that encode a receptor that is often functionally equivalent to the wild-type receptor and confer a PDGF-sensitive mitogenic response on the cell. In this way, the binding properties of the naturally-occurring PDGF will be analyzed, as well as fragments or synthetic compounds, both proteinaceous and non-proteinaceous. As demonstrated in the Experimental section, transfected cells were used to determine that the AA form of PDGF activates the type B receptor tyrosine kinase. The presence of the type A and type B receptor polypeptides in a single cell will facilitate the study of receptor binding properties and perhaps even receptor interactions.

In addition to studying PDGF-mediated mitogenesis, the transfected cells can be used to evaluate a drug's ability to function as a PDGF agonist or antagonist. In particular, transfected cells can be contacted with the test drug, and the amount of response determined, e.g., receptor tyrosine kinase activation or the rate of DNA synthesis, as compared to control cells in the presence or absence of PDGF or analogs thereof. Alternatively, in a non-therapeutic environment, a method is provided for inhibiting binding between a PDGF analogue and a PDGF receptor present in a solution. This method will contain a step of adding a PDGF receptor peptide, e.g., a peptide homologous to a sequence described in Table 2 or Table 3 to the solution, or a mutation or modification of one. Binding affinity to variants of the PDGF will also be evaluated by such cells. The inhibition of binding will usually occur by competition or by interfering with binding, on either the receptor or the ligand. The assay will often make use of comparisons with and without test ligand, or by a displacement assay, where the displacing ligand is added after binding occurs.

However, as indicated above, the PDGF receptor likely functions in a dimer state. The soluble forms of the receptor may interfere with the dimerization and, in some embodiments, will be effective in blocking signal transduction by a different mechanism from competitive affinity for the PDGF ligands. The soluble, or intracellular or transmembrane fragments of the various receptor forms would interfere with dimer formation and thus blocks at least some types of, or some fraction of, signal transduction.

This observation provides a method for modifying in vivo a PDGF receptor modulated activity comprising administering to a patient an amount of a PDGF receptor blocking agent effective to inhibit PDGF binding to PDGF receptors. Sometimes, the blockage will occur at the level of ligand binding, by blocking the functional assembly of the receptor complex, or by blocking further interaction of the receptor with other proteins important in effecting cellular response, e.g., phosphotyrosine binding interactions. As discussed above, the PDGF family of proteins have a significant role in regulating many important physiological processes. The soluble PDGF-R polypeptides will generally be effective in modifying the extent of PDGF modulation of these processes. For this reason, the soluble forms of the receptors are useful as competitive binding sites for PDGF. Likewise, truncated PDGF binding sites or binding sites which have been mutated, particularly those from the human forms described, will sometimes be equally effective as natural forms, but at a lesser cost, both in monetary terms of and in terms of medical side-effects, upon administration.

The reagents provided herein will also find use in the quantitative detection or diagnosis of PDGF analogues, or PDGF-like ligands for the receptors, or for PDGF receptor polypeptide production. Various medical conditions are indicated by an abnormal level of production of either of these proteins, including, e.g., various tumor conditions. Thus, diagnostic tests dependent upon these reagents are now available.

With the different PDGF types, combining segments into chimeric receptors will form different types of receptors having variations in affinities for the various ligands. With the genes and proteins of the present invention, distinctions between various patterns and receptor types will be found, specific for various tissue types. Thus, tissue markers based upon differences in PDGF receptor expression would become available.

Soluble fragments containing various regions of the extracellular region of the human PDGF receptor have been shown to retain high affinity specific binding as in the intact type B PDGF receptor. The extracellular region of the human receptor has been expressed at high levels in CHO cells and secreted into the medium. In the presence of ligand, the soluble extracellular fragments block the ability of BB-PDGF to initiate responses characteristic of a physiological mitogen response. The soluble fragments also retain high specificity in binding to only the BB PDGF, not altering the mitogenic effect by the AA PDGF. Additional experiments using the human extracellular region have shown that the fragments may be used as binding segments to assay, e.g., by competition, for the presence of ligands. These results suggest the possibility of treating various conditions which excessively respond to PDGF such as atherosclerosis, osteosarcoma, and glioblastoma. The mitogenic response may be attenuated through use of the soluble extracellular fragments.

The blocking of physiological response to PDGF results from the inhibition of binding of the ligand to the receptor, likely through competitive inhibition. Thus, in vitro assays of the present invention will generally use soluble fragments comprising the ligand binding segments of these receptors, or fragments attached to solid phase substrates. These assays will also allow for the diagnostic determination of the effects of either binding segment mutations and modifications, or ligand mutations and modifications, e.g., ligand analogues.

The soluble fragments will also find use in testing interaction of the receptor with modified ligands, e.g., biotinylated AA isoform or other PDGF forms. Another means for blocking ligand action will be to interfere with proper multi-protein receptor association, e.g., dimerization, or intracellular region interactions with other proteins. In particular, it is demonstrated that particular phosphorylation events control interactions with other protein which mediate other cellular functions. Various assays for this are well known to those skilled in the art, and see below.

Receptor components may be substituted by equivalent or corresponding soluble fragments from the other type polypeptide, e.g., exchanging fragments from the type A and type B polypeptide forms, or from other related polypeptides, e.g., mouse receptors, or other related receptors.

Moreover, because the type A homodimer binds all three forms of PDGF, the type A binding fragments exhibit substantial generality of ligand binding. The type A binding fragments are useful for preparing general PDGF binding reagents.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al. (eds) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; each of which is hereby incorporated herein by reference. Methods for administration are discussed therein, e.g., for oral, intravenous, intraperitoneal, or intramuscular administration, transdermal diffusion, and others. Pharmaceutically acceptable carriers will include water, saline, buffers, and other compounds described, e.g., in the Merck Index, Merck & Co., Rahway, N.J. Because of the high affinity binding between PDGF and its receptors, low dosages of these reagents would be initially expected to be effective. Thus, dosage ranges would ordinarily be expected to be in amounts lower than 1 mM concentrations, typically less than about 10 μM concentrations, usually less than about 100 nM, preferably less than about 10 pM (picomolar), and most preferably less than about 1 fM (femtomolar), with an appropriate carrier. Slow release formulations, or slow release apparatus will often be utilized for continuous administration. The intracellular segments of the receptors, both the PDGF receptor and related receptors will find additional uses as described in detail below.

The pharmaceutical compositions will be administered by parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and dragees.

The pharmaceutical compositions will often be administered intravenously. Thus, this invention provides compositions for intravenous administration which comprise a solution of the compound dissolved or suspended in an acceptable carrier, preferably an aqueous carrier. A variety of aqueous carriers may be used, e.g., water, buffered water, 0.4% saline, and the like. These compositions will sometimes be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, preferably about 20% (see, *Remington's*, supra).

For aerosol administration, the compounds are preferably supplied in finely divided form along with a surfactant and propellant. The surfactant should, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Often mixed esters, such as mixed or natural glycerides will be employed. The surfactant, in some embodiments, will constitute 0.1%–20% by weight of the composition, preferably 0.25–5%. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above will sometimes also be employed. In producing the aerosol, a container equipped with a suitable valve is filled with the appropriate propellant, containing the finely divided compounds and surfactant. The ingredients are thus maintained at an elevated pressure until released by action of the valve.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient.

In prophylactic applications, compositions containing the compounds of the invention are administered to a patient susceptible to or otherwise at risk of a particular disease. Such an amount is defined to be a "prophylactically effective dose." In this use, the precise amounts again depend on the patient's state of health and weight.

In a particularly important aspect of the present invention, it was recognized that many growth factors mediate their pleiotropic actions by binding to and activating cell surface receptors with an intrinsic protein tyrosine kinase activity. Growth factor receptors with tyrosine kinase activity, or receptor tyrosine kinases, typically possess similarities in molecular topology. For example, they possess a large extracellular ligand binding region, a hydrophobic transmembrane region, and a cytoplasmic, i.e., intracellular, region that contains a tyrosine kinase catalytic domain. Receptor tyrosine kinases typically have a topology dictating that the ligand binding segments and protein tyrosine kinase activity are separated by the plasma membrane. Therefore, receptor activation due to extracellular ligand binding is translated across the membrane barrier into activation of intracellular region functions.

The present invention takes advantage of the discovery that phosphorylation of particular amino acid residues in a polypeptide segment is important in certain protein-protein interactions. The phosphorylation state of residues within the regions of interaction, or coupling regions, modulate the interactions. In the case of the PDGF receptor and phosphatidylinositol 3' kinase (PI3 kinase) interactions, the presence of a phosphotyrosine in the defined kinase insert sequence is important in the interacting between, e.g., binding between, the receptor and the PI3 kinase, thereby activating the PI3 kinase enzyme. An unphosphorylated KI segment fails to bind a PI3 kinase activity. These observations will be generally applicable to the interaction of phosphorylated segments with other binding proteins. With the elucidation of the nature and specificity of these interactions, analogues, e.g., organic molecules, are prepared which serve as analogues to the peptides or phosphorylated peptides.

Tyrosine kinases can be broadly classified into two groups, the transmembrane receptor kinases and the cytoplasmic non-receptor kinases, with most of the members of the second group belonging to the so-called src family of tyrosine kinases. The receptor kinases genes, including the PDGF receptor, share certain structural features, e.g., an amino-terminal signal peptide which is characteristic of membrane glycoproteins and a transmembrane segment which defines and separates the extracellular and the intracellular regions of the receptor protein. The amino-terminal portion of the receptor protein makes up the extracellular region which contains the ligand binding sites. The carboxy-terminal portion of the protein makes up the intracellular region of the receptor, on which the kinase activity is located. Receptor kinases are responsible for transducing a signal provided by ligand binding to the extracellular region into the intracellular compartment, and through cytoplasmic second messages, ultimately to the nucleus.

Detailed comparison of established receptor tyrosine kinase (RTK) primary sequences has led to the identification of both shared and unique structural subdomains, or segments, which permit classification of the RTK family into distinct groups, see, e.g., Yarden and Ullrich (1988) *Ann. Rev. Biochem.* 57:443–478; and Ullrich and Schlessinger (1990) *Cell* 61:203–212; each of which is incorporated herein by reference.

The PDGF receptor is a member of One such subclass. These receptors, including macrophage growth factor (CSF-1-R) and the putative receptor c-kit share at least two distinct structural features. They lack cysteine-rich repeat clusters within their extracellular regions, and they possess another conserved repeat structure that includes five immunoglobulin-like repeats, suggesting a common architecture for the ligand-binding regions of the members of this receptor subclass.

Furthermore, when compared with RTKs of other subclasses, the catalytic domains of members of this group are interrupted by long, structurally unique, hydrophilic, proline-rich insertion sequences of about 77–107 amino acid residues. This "kinase insert" (KI), also referred to as a kinase insert region, divides the catalytic domain into two segments and is defined by homology to other tyrosine kinase domains. These KI sequences are highly divergent, even within each receptor subfamily, but are strongly conserved between evolutionarily distant species, such as chickens, cats and humans. Members of a related subclass, including the FGF receptor, flg, and bek, similarly have immunoglobulin-like repeats in their extracellular region, although only three in number, and kinase insert sequences of 10–19 residues located in the corresponding position of the tyrosine kinase segments.

RTK ligands induce pleiotropic cellular responses, which in many cell types culminate in cell cycle progression, DNA synthesis, and cellular replication. Upon ligand binding, numerous responsive membrane events are initiated, including stimulation of ion transport, glucose transport, membrane kinases, pinocytosis, membrane ruffling, and other cytoskeletal and morphological changes. These events are paralleled by activation of a number of cytoplasmic pathways, including glycolysis, polyamine synthesis, and ribosomal protein S6 phosphorylation. Alterations in the pattern of specific gene transcription (e.g., c-myc and c-fos) are detectable within minutes, and increased macromolecular synthesis of protein, RNA and DNA is observed within about 3–20 hours after ligand binding. PDGF has the unique capability of stimulating both protein kinase C, through an increased turnover of phosphatidylinositol, and protein kinase A, through production of type E prostaglandin.

The importance of the correct regulation of receptor function is emphasized by the fact that a large variety of structural alterations found in receptor-derived oncogene products lead to constitutive activation and, consequently, subversion of molecular control mechanisms and alteration of receptor signals. The most common cellular lesion found in human cancers involves autocrine activation in conjunction with receptor overexpression. Many tumors and tumor cell lines have been found to coexpress growth factors and their receptors, including PDGF-A chain, PDGF-B chain, and PDGF receptor polypeptides. Autocrine receptor activation represents one scenario of subversion of normal growth control. In principle, every receptor with tyrosine kinase activity has oncogenic potential. Many more types of activating mutations, as well as specific instances of receptor tyrosine kinase overexpression, would be anticipated to be detected in animal and human tumors. The understanding and control of such defects in normal cellular metabolism and signal transduction will play an important role in the diagnosis and therapy of oncogenesis.

When activated by ligand, the PDGF β-receptor becomes phosphorylated on tyrosine residues. See, e.g., Ek and Heldin (1982) *J. Biol. Chem.* 257: 10486; Frackelton et al. (1984) *J. Biol. Chem.* 259: 7909; Kazlauskas and Cooper (1989) *Cell* 58: 1121; and Yarden et al. (1986) *Nature* 323: 226–232. The mechanism of this "autophosphorylation" reaction appears to depend on ligand-induced formation of receptor dimers and a transphosphorylation reaction in which each of the two polypeptide chains of the dimer phosphorylates the other chain. The major sites of PDGF stimulated receptor phosphorylation are located in the carboxyl terminal portion of the tyrosine kinase domain, about tyr(825) in both the human and mouse type B receptor, and in the kinase insert region, about tyr(719) in both the human and mouse type B, that splits the kinase coding sequences into two parts. It is likely that additional sites of autophosphorylation have not yet been identified.

One of the consequences of ligand-induced receptor autophosphorylation appears to be a change in conformation of the intracelluar region of the receptor. In its activated state the receptor can physically interact with several cytoplasmic molecules that are likely to be important in signal transduction.

Activation is also accompanied by complex formation with, and tyrosine phosphorylation of, a variety of proteins. The first to be described was a protein of 85 kD, which is a putative PI kinase and identical to a protein referred to as p81, see Kaplan et al. (1987) *Cell* 50:1021. Subsequently, a number of other proteins have been shown to complex with PDGF receptors and to become phosphorylated on tyrosine following PDGF stimulation. These include the serine/threonine kinase Raf-1, which becomes activated in the complex; see, e.g., Morrison et al. (1989) *Cell* 58: 649–657; and phospholipase C-γ, see, e.g., Morrison et al. (1990) *Mol. Cell. Biol.* 10: 2359–2366; and GAP, the GTPase activating protein involved in the control of ras activity, see, e.g., Kaplan et al. (1990) *Cell* 58: 1121–1133. PDGF treatment also enhances the kinase activities of some of these proteins.

Recently, transient complex formation also has been shown to occur between three src family tyrosine kinases (pp60-c-src, p59-fyn, and pp62-c-yes), p81, and PDGF receptors. In addition, PDGF treatment stimulates the tyrosine kinase activates of these proteins, suggesting that src family kinases may play a role in the response to PDGF. Phosphorylation on tyrosine residues likely activates the mitogenic potential of the target protein either by enhancing its enzymatic activity or by altering its interactions with other cellular proteins.

The SH2 system provides possible guidance to particular mechanisms and properties which could be applicable to the PDGF receptors. Some non-receptor tyrosine kinases share a conserved noncatalytic region of approximately 100 amino acids called the src homology region 2 (SH2) domain. The SH2 domains of the Fps and Src tyrosine kinases are thought to possibly interact with and regulate the adjacent kinase domain and may also form binding sites for proteins phosphorylated by the kinase domain.

Phospholipase C-γ (PLC-γ) and p21-ras GTPase-activating protein (GAP) each contain two adjacent SH2 domains. Recent experiments have shown that SH2 domains endow proteins such as GAP, v-Crk and p60-v-src with the potential to form complexes with specific tyrosine phosphorylated ligands. The relevance of these results to the PDGF-R was, until now, unclear. In the PDGF receptor embodiments, ligand-activated PDGF receptor induces the formation of a complex of signaling molecules including PLC-γ, Raf-1, and the 85 kDa PI-3 kinase.

One of the first of the signaling molecules to be identified as a receptor-associated protein was phosphatidyl-inositol-3' kinase (PI3 kinase). This enzyme was originally found to be a kinase that co-immunoprecipitated with the complex of polyoma middle T antigen and the c-src protein, and with transforming v-src proteins. PI3 kinase activity was also found in phosphotyrosine or receptor immunoprecipitates of lysates from PDGF-stimulated cells. The specific role of PI3 kinase in mediating cell proliferation has not been determined. However, the enzyme is regulated by a number of growth factors and growth factor-treated cells contain increased levels of phosphoinositides and inositol phosphates phosphorylated on the 3 position of the inositol ring. Mutants of middle T antigen or the PDGF receptor that do not associate with PI3 kinase are defective in their mitogenic activities. The protein responsible for the PI3 kinase activity has not been well characterized. However the close correlation of the enzymatic activity with the presence of an 81–85 kD protein in co-immunoprecipitation experiments with the middle T/c-src complex and with the PDGF receptor has strongly suggested that the 85 kD protein is either the PI3 kinase or an important subunit of the kinase.

Definable regions of the PDGF receptor were capable of mediating the interaction with PI3 kinase, as evidenced by an analysis of a mutated type B PDGF receptor having a deletion of the kinase insert (KI) region. This receptor mutant (ΔKI) was defective in stimulating cell proliferation and in binding PI3 kinase, even though it had tyrosine kinase activity and stimulated several other responses to PDGF binding, including phospholipase C-mediated PI hydrolysis. Recent studies have shown that the ligand-activated ΔKI mutant receptor fails to bind PI3 kinase, but binds as much PLC-γ and the c-Raf-1 proteins as the wild type receptor. However, the mutant receptor is unable to phosphorylate c-Raf-1 an tyrosine residues and the binding of PLC-γ required tyrosine phosphorylation of the receptor. A mutant of the human type B PDGF receptor that had one of the phosphorylation sites in the kinase insert domain, tyr(719) in both the human type B receptor, converted to phenylalanine was -also defective in binding PI3 kinase. These experiments indicate that either the PI3 kinase binds directly to a portion of the kinase insert region containing tyr(719) or that the binding interaction involves other portions of the receptor that are conformationally dependent on sequences in the kinase insert region.

To directly study the interaction between the type B PDGF receptor and PI3 kinase, an in vitro system was established. With this system, it was possible to test the ability of synthetic polypeptides derived from receptor sequences in the kinase insert domain to block interaction of the PI3 kinase with the PDGF receptor. The interaction could be blocked by a tyrosine-phosphorylated peptide representing a highly conserved region of the kinase insert domain that included tyr(719). However the peptide blocked PI3 kinase binding to the PDGF receptor only when the peptide was phosphorylated on tyrosine. Scrambled versions of the peptide, even when phosphorylated on tyrosine, had no blocking activity. These studies show that phosphotyrosine in a specific sequence context serves as a recognition site for the binding of a cytoplasmic signaling molecule.

An in vitro system was used to study the interaction of PDGF receptors and PI3 kinase. The association of phosphoproteins with the PDGF receptor is demonstrated by stimulating 3T3 cells with PDGF, immunoprecipitating cell lysates with type B PDGF receptor antibodies and by examining the immunoprecipitates for the presence of receptor-associated proteins that can be phosphorylated in the immunoprecipitates. See FIG. 1a "+" lanes. These phosphoproteins include the 85 kDa protein and a 110 kDa protein that have recently been correlated with PI3 kinase activity. See FIG. 1c. In in vitro experiments, the type B PDGF receptor was expressed in an insect cell expression system, partially purified, and immobilized using anti-receptor antibodies and protein A Sepharose. The receptor was allowed to autophosphorylate in vitro, so that it would be in a conformation that mimicked the ligand-activated state of the receptor. Cytoplasmic cell lysates from density-arrested BALB/c 3T3 cells were mixed with the immobilized receptor and the complexes were washed extensively. PI3 kinase activity was found in the complex of proteins associated with the receptor (FIG. 1d). The receptor-associated phosphoproteins were detected by an in vitro kinase assay using $^{32}$P-ATP. See FIG. 1b "−" lane. At least four receptor-associated proteins with apparent molecular weights of 140 kD, 120/110 kD (sometimes a doublet), 85 kD and 74 kD were radiolabeled (the bands at 160 kD and 150 kD are the baculovirus-expressed receptor and its precursor, respectively). The 140 kD band has been previously identified as PLC-γ and the band at 74 kD includes the raf-1 kinase and probably another molecule as well. The 85 kD protein co-migrated with the 85 kD band, previously considered to be PI3 kinase, in anti-phosphotyrosine immunoprecipitates of cell lysates prepared from PDGF-stimulated cells. The association of 85 and 110 kD proteins with the baculovirus-expressed receptor was also observed by silver stain analysis. When cell lysate was incubated with immobilized kinase insert deletion mutant of the PDGF receptor there was no associated PI3 kinase activity, and the 110 kD and 85 kD phosphoproteins did not associate with the mutant receptor. See FIGS. 2a and A 2b. This in vitro result is consistent with previous indications that this receptor mutant does not associate with PI3 kinase in intact cells.

When 3T3 cells were stimulated with PDGF prior to making the lysates, there was a dramatic reduction in the amount of PI3 kinase available for association with the receptor in vitro (FIG. 1d) and a concomitant reduction in the association of the 85 kD and 110 kD phosphoproteins with the receptor (FIG. 1b "+"lane). Although the explanation of this phenomenon is not entirely clear, the observation that PDGF pretreatment of cells influences the subsequent in vitro association of cellular proteins with the receptor indicates that the associations are specific PDGF-regulated processes.

When the autophosphorylated PDGF receptor was dephosphorylated in vitro using potato acid phosphates (PAP) it lost the ability to associate with PI3 kinase activity or 84 kD protein derived from the BALB/c 3T3 cell lysates (FIGS. 3b and c). This finding indicates that phosphorylation of the PDGF receptor was required for these protein interactions to occur.

To identify the site of interaction between the receptor and the PI3 kinase, phosphorylated synthetic peptides were prepared to compete for the binding of the 85 kD protein and the PI3 kinase activity to the receptor in vitro. Previous data suggested that the kinase insert region was involved in the association of the PI3 kinase activity with the PDGF receptor. In scanning sequences from the kinase insert regions of the mouse and human PDGF type B and type A receptors, a 20 amino acid region of particularly high sequence homology (8 out of 20 identities for the human and mouse PDGF type B receptor compared to 12% identity for the entire kinase insert region) was found. A peptide (Y719) containing amino acids 705 to 724 of the mouse type B PDGF receptor sequence was synthesized. This peptide sequence contained two tyrosine residues, Y708 and Y719. The tyrosine at position 719 of the mouse sequence also corresponds to tyr(719) in the human type B PDGF receptor, a known autophosphorylation site of the receptor.

To determine the ability of a series of synthetic peptides derived from this sequence to block the interaction between the receptor and the 85 kD/PI3 kinase activity, 3T3 lysates were incubated with the different peptides prior to mixing with immobilized receptor. The results of these experiments are shown in FIG. 4. The first lane of FIG. 4a shows phosphorylated proteins that associated with the wild type receptor in the absence of peptides. The arrow indicates the position of the 85 kD protein that co-purified with the PI3 kinase activity. The other lanes show the proteins that associated with the receptor in the presence of derivatives of the Y719 peptide. See Table 4. No change in the pattern of receptor-associated protein was seen when the unphosphorylated 719 peptide (Y719) was preincubated with the 3T3 lysate prior to the association with the receptor. By contrast when a derivative of this peptide that was phosphorylated at position 719 (Y719P) was added to the incubation, it blocked the binding of the 85 kD phosphoprotein (FIG. 4a) and inhibited the association of PI3 kinase activity (FIG. 4b) with the receptor. A scrambled version of this peptide that contained phosphotyrosine at a position corresponding to 719 but had a rearranged primary sequence failed to block binding of the 85 kD protein and did not prevent the association of PI3 kinase activity with the receptor.

| Peptides | Sequence | SEQ ID NO. |
|---|---|---|
| Y719 | GGYMDMSKDESIDYVPMLDM | SEQ ID NO:5 |

*

-continued

| Peptides | Sequence | SEQ ID NO. |
|---|---|---|
| Y719P | GGYMDMSKDESIDYVPMLDM | SEQ ID NO:6 |
| Y708P | GGYMDMSKDESIDYVPMLDM (* over position 3) | SEQ ID NO:7 |
| Y719P short | MDMSKDESIDYVPMLDM (* over Y) | SEQ ID NO:8 |
| Y708P short | GGYMDMSKDESID (* over Y) | SEQ ID NO:9 |
| Y708P/F719 | GGYMDMSKDESIDFVPMLDM (* over Y) | SEQ ID NO:10 |
| F708/Y719P | GGFMDMSKDESIDYVPMLDM (* over Y) | SEQ ID NO:11 |
| Y708P/Y719P | GGYMDMSKDESIDYVPMLDM (* over both Y) | SEQ ID NO:12 |
| Y719P scrambled | MMDIKVPMDEYMSDYSDLGG (* over E) | SEQ ID NO:13 |

The asterisks (*) indicate the position of a phosphate group

A shorter version of peptide Y719P that includes only 14 amino acids (Y719P short) and lacked tyrosine 708 also blocked binding of the 85 kD protein (FIG. 4a, lane 4) and inhibited the association of PI3 kinase activity with the receptor. Surprisingly, a peptide that includes tyrosine at position 719 and phosphotyrosine at position 708 blocked the interaction of PI3 kinase with the receptor (FIG. 4, lane 6). This finding suggests the possibility that tyrosine 708 is one of the autophosphorylation sites of the receptor that has not yet been mapped. A peptide that included phosphotyrosine at both positions 708 and 719 (Y708P/Y719P) also blocked binding of the 85 kD protein (FIG. 4, lane 8). Short forms of Y708P and Y719P also had blocking activity (FIG. 4 lanes 4 and 9).

Figure 5A:
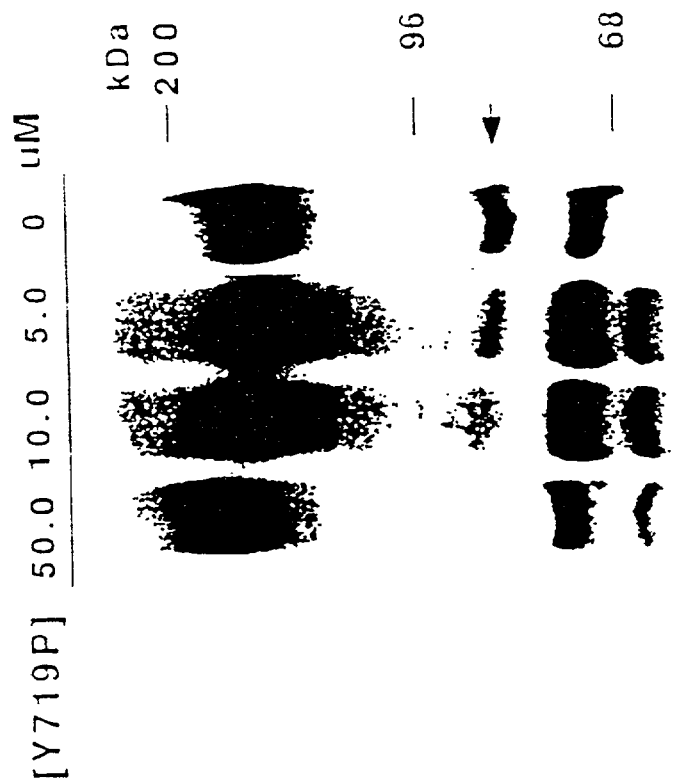
FIG. 5 illustrates the concentration-dependance of the blocking activity of peptide Y719P. A series of concentrations of peptide Y719P were tested for the ability to block the binding of proteins (panel a) or PI3 kinase activity (panel b) to baculovirus-expressed immunoprecipitated receptor. The arrow points to the 85 kD phosphoprotein. The assays were performed as described in FIGS. 1, 2 and 3.
Figure 5B:
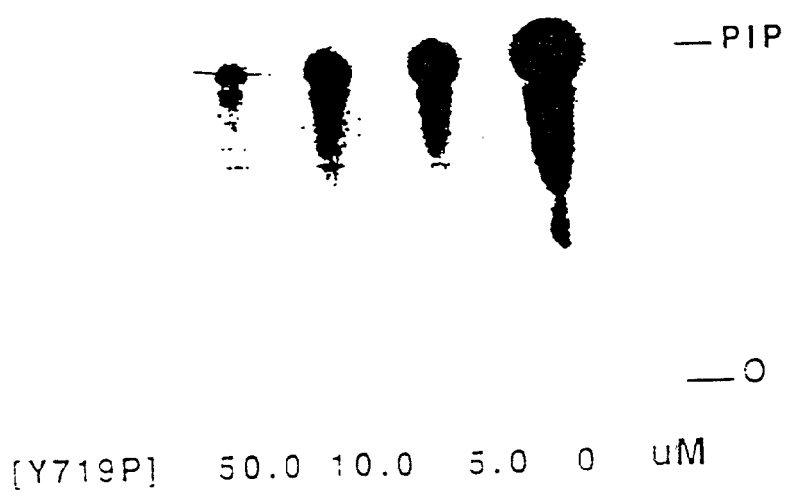
Figure 6:
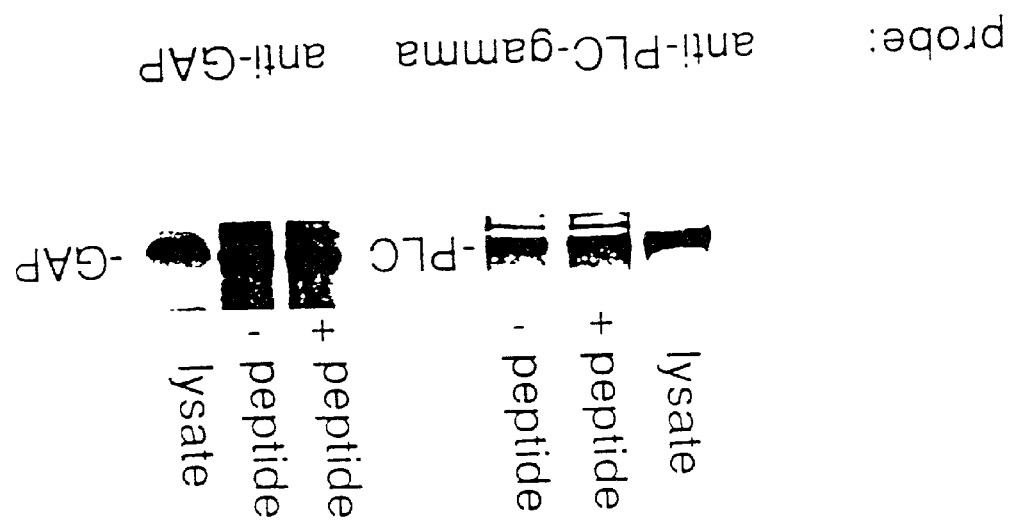
FIG. 6 illustrates that the association of PDGF receptor with PLC-γ and GAP is not affected by preincubation of 3T3 unstimulated lysates with receptor phosphopeptide, Y719P. Unstimulated 3T3 lysates were preincubated in the presence and absence of a receptor phosphopeptide (Y719P) prior to the association with the baculovirus-expressed receptor. The peptide/lysate mixture was incubated with the immunoprecipitated baculovirus-expressed receptor as described in FIGS. 1, 2 and 3. The presence of PLC-γ and GAP in the receptor complex was determined by immunoblot analysis using PLC-γ and GAP antibodies as probes. In the lane marked "lysates", crude lysates of 3T3 cells were immunoblotted as controls to show the electrophoretic position of the PLC-γ and GAP.

To determine the amount of peptide necessary to block the association of the 85 kD and the PI3 kinase activity to the receptor, the 3T3 lysates were preincubated with a range of concentrations of phosphorylated peptide (Y719P). As shown in FIG. 5, approximately 5 µM of Y719P was sufficient-to block more than 50% of the association of the 85 kD protein (FIG. 5a) and PI3 kinase activity (FIG. 6B) with the receptor. Concentrations of up to 100 µM of unphosphorylated peptide did not affect association between the receptor and the PI3 kinase. Thus the coincident blocking of 85 kD and PI3 kinase activity association with the receptor by peptide Y719P supports the hypothesis that the 85 kD protein is a subunit of the PI3 kinase enzyme.

Next, the ability of peptides to block the association of other signaling molecules with the receptor was assessed. Lysates from 3T3 cells were incubated in the absence or the presence of peptide Y719P prior to association with the receptor immunoprecipitates. The association of PLC-γ and GAP with the receptor was determined by immunoblot analysis using specific antibodies (FIG. 6), confirming previous studies that these molecules specifically associate with autophosphorylated receptors. The association of these proteins with the receptor was not affected by the addition of the phosphorylated peptide, Y719P. Thus the Y719P peptide specifically blocked association of 85 kD/PI3 kinase activity with the receptor and did not affect the interaction of the receptor with GAP or PLC-γ.

Figure 7:
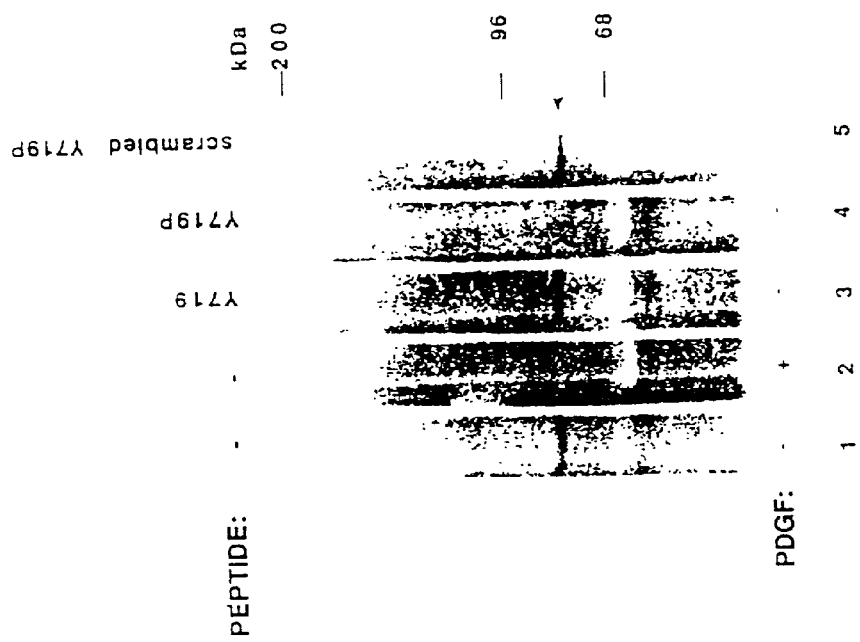
FIG. 7 illustrates the association of soluble radiolabeled receptor with immobilized 85 kD protein ("receptor blot"). Baculovirus-expressed PDGF receptors were immunoprecipitated using receptor antibodies and the receptor was $^{32}$P-labeled in vitro by autophosphorylation. The solubilized radiolabeled receptor was used to probe nitrocellulose filters containing SDS-polyacrylamide gel-fractionated lysates from control (lanes 1, 3, 4 and 5) or PDGF stimulated (lane 2) cells. In the peptide competition experiments (lane 3, 4, and 5) the peptides were added to the nitrocellulose paper along with the radiolabeled receptor probe. The arrow indicates the position of the 85 kD protein.

To determine the nature of the interaction of the receptor with the 85 kD protein, a modification of Western blotting methodology was used. PDGF receptor from Sf9 cells infected with PDGF receptor baculovirus was immuno precipitated with receptor antibodies, labeled with $^{32}$P in vitro, and used as a probe to bind proteins from 3T3 cell lysates that had been separated electrophoretically and transferred to nitrocellulose. The radiolabeled PDGF receptor bound directly to an 85 kDa protein in unstimulated 3T3 cell lysate (FIG. 7, lane 1). Cell lysates from PDGF-treated 3T3 cells did not show any binding when incubated with the radiolabeled PDGF receptor, (FIG. 7, lane 2) consistent with the finding that the 85 kD protein from PDGF-stimulated lysates was not available for association with the immobilized PDGF receptor (FIG. 1b). When the nitrocellulose paper that contained cell lysate proteins was pre-incubated with peptide Y719P, the radiolabeled receptor failed to associate with the 85 kD protein (FIG. 7, lane 4). The unphosphorylated peptide (Y719) or the scrambled peptide (Y719P scrambled) did not interfere with the association of the receptor with the 85 kD protein (FIG. 7, lanes 3 and 5). This experiment showed that the 85 kD protein (FIG. 7, lanes 3 and 5). This experiment showed that the 85 kD protein binds directly to the PDGF receptor and does not require the presence of other molecules. The direct binding interaction appears to involve the 20 amino acid segment in the kinase insert region containing tyrosine 719, and tyrosine phosphorylation of this segment appears to be necessary for the interaction.

These results indicate that the intracellular region of the type B PDGF receptor interacts with molecules that are likely to play a role in signal transduction. The physical association between the receptor and signaling molecules such as PI3 kinase, PLC-γ, GAP, and raf-1 only occurs when the receptor is phosphorylated on tyrosine. See FIG. 1a. A region of the receptor that is involved in the binding of the receptor to the PI3 kinase has been defined. Short peptides were used to block the in vitro association of PI3 kinase with the phosphorylated receptor. The most likely explanation for the ability of the peptides to block the association is that they mimic the receptor and bind directly to the PI3 kinase. In this way they act as competitive antagonists. The observation that only tyrosine-phosphorylated peptides had this blocking activity suggests that phosphotyrosine is directly involved in the binding of the receptor to PI3 kinase. However phosphotyrosine alone is not sufficient for binding, since scrambled peptides containing phosphotyrosine did not interact with the PI3 kinase. Therefore the primary sequence of this portion of the receptor has essential structural information that is required for the binding of the receptor to PI3 kinase. It is somewhat surprising that peptides as short as 13 amino acids contained enough structural information to mimic the native receptor region that normally binds to the PI3 kinase (Table 4).

Tyrosine 719 of the type B PDGF receptor is one of the autophosphorylation sites of the receptor in intact cells as well as in vitro. Thus, it appears that the portion of the KI domain around tyrosine 719 is directly involved in the association of PI3 kinase with the receptor in vivo. The data presented herein indicate that peptide derivatives of Y719 containing one of the two tyrosine residues phosphorylated (Y708P or Y719P) efficiently prevented the association of the receptor with the PI3 kinase in in vitro assay. Similar sequences and interactions are subject to blockage by the appropriate fragment sequences. In particular, sequences known to be phosphorylation sites will be used to select for analogues which block interaction with other mediating proteins. The PI3 kinase is known to associate with the c-fms protein and with the middle T antigen, and both of these proteins are phosphorylated on tyrosine in vivo. A phosphorylation site of the middle T antigen (tyrosine 315) is in a sequence somewhat homologous (5 out of 10 amino acids are identical) to the peptide Y719P used in our experiments. There is no obvious homology of peptide Y719P to any of the tyrosine phosphorylation sites on the c-fms protein. However peptide Y719P blocked association of PI3 kinase with the c-fms protein in vitro. Thus an autophosphorylation site of the c-fms protein is in a region that has a secondary structure that is similar to the corresponding domain of the PDGF receptor.

These findings indicate that signaling molecules recognize phosphotyrosine in a specific sequence context. The pattern of interactions of the kinase insert deletion mutant with GAP, PLC-γ, and c-raf-1 and the lack of ability of the peptides used in this report to block GAP and PLC-γ association with the receptor shows that different regions of the receptor, possibly containing different autophosphorylation sites, are involved in the binding of specific signaling molecules. The binding of these molecules to the receptor localize the signaling molecules and regulate their activities. Tyrosine phosphorylation of other cellular proteins by the receptor kinase targets them as proteins for binding signaling molecules and the present invention provides the methods and materials for generating reagents which will successfully mimic or interfere with natural signals. For example, fragments from the hPDGF-receptor, or related tyrosine kinase proteins, will be useful to block the natural interactions between them and function-mediating proteins. See, e.g., Williams (1989) *Science* 243: 1564–1570; Yarden et al. (1986) *Nature* 323: 226–232; and GenBank™, for other sequences and proteins which show homology, both structural and functional, with the phosphorylated inserts described herein.

This discovery leads the way to the production of analogues of the KI segments. For example, short peptides having non-hydrolyzable moieties will often be produced with, e.g., sulfonated moieties substituted for phosphorylated moieties. Alternatively, other organic molecules exhibiting sufficient structural homology will often be selected for their functional interaction with the PI3 kinase or other function mediating proteins. In addition, chimeric analogues, portions of which are peptide, or modified peptide, and other portions of which are organic molecules which have similar structural features which are important for interaction, will be constructed. Thus, molecules exhibiting particular interacting features become available, including both natural or synthetically generated compounds.

The invention will better be understood by reference to the following illustrative examples. The following examples are offered by way of illustration and not by way of limitation.

EXPERIMENTAL

In general, standard techniques of recombinant DNA technology are described in various publications, e.g., Sambrook et al. (1989) *Molecular Cloning: A Laboratory Manual*, Cold Spring Harbor Laboratory; Ausubel, et al. (1987) *Current Protocols in Molecular Biology*, vols. 1 and 2 and supplements; and Wu and Grossman (eds.) (1987) *Methods in Enzymology* Vol. 53 (Recombinant DNA Part D); each of which is incorporated herein by reference. Variations, if any, on those methods have generally been minor.

I. Screening of Human Kidney λGT11 cDNA Library and Human Placenta λGT10 cDNA Library A full-length DNA sequence encoding the mouse PDGF receptor (mPDGF-R) protein was used as a probe to screen 250,000 plaques of a human kidney cDNA library. Nick translation was used to prepare a probe with specific activity of $12 \times 10^8$ cpm per μg. The filters were incubated with the probe ($10^5$ cpm per ml) in hybridization buffer containing 30% formamide, 1×Denhardt's solution, 5×SSC, 0.02 M sodium phosphate pH 6.5, and 500 μg per ml of salmon sperm DNA. After 14 h of hybridization at 40° C., the filters were washed four times at 55° C. with 0.2×SSC and 0.1% SDS and two additional times at 65° C. with 0.2×SSC. The filters were then air dried and exposed for 16 h.

Ten positive clones were obtained which were rescreened with the full-length mPDGF-R probe. Individual clones were isolated and analyzed by restriction analysis using EcoRI endonuclease. The clone containing the largest insert (2.3 kb), designated clone HK-6, was further characterized and sequenced using dideoxy terminators. Clone HK-6 contained the receptor sequence from nucleotide 3554 to nucleotide 5691 plus nine bases from the poly-A tail.

A nick-translated probe, prepared from the 2.3 kb HK-6 DNA, was used to screen 250,000 plaques of a human placenta cDNA library. This screening was performed at high hybridization stringency (50% formamide in the hybridization buffer described above). The filters were incubated with $5 \times 10^5$ cpm per ml of probe for 14–16 h at 42° C. The filters were than washed at 65° C. in 0.1% SSC and 0.1% SDS four times.

After secondary screening with the HK-6 probe, seven clones were selected and analyzed by restriction digestion with EcoRI endonuclease. A clone (HP-7) that contained a 4.5 kb insert was selected and characterized. The sequence of that clone is described in Table 2 and encodes the type B human PDGF receptor (B-hPDGF-R).

II. Construction of Expression Vector

The 4.5 kb DNA fragment containing the complete coding sequence for the type B human PDGF receptor was isolated from the HP-7 clone by EcoRI digestion. The gel purified fragment was cloned into the EcoRI site in the polylinker region of SV40 expression vector PSV7C. The pSV7d expression vector, obtained from P. Luciw, at the University of California, Davis, was a pML derivative containing the SV40 early promoter region (SV40 nucleotides 5190–5270), a synthetic polylinker with restriction sites for EcoRI, SmaI, XbaI, and SalI followed by three translation terminator codons (TAA) and the SV40 polyadenylation signal (SV40 nucleotides 2556–2770) (Truett et al. (1984) *DNA* 4:333–349). The EcoRI fragment containing the cDNA sequence obtained from the HP-7 clone was inserted at the EcoRI site of the pSV7d. In the resulting expression vector, the B-hPDGF-receptor gene was under transcriptional control of the SV40 promoter.

To ensure the proper orientation of the PDGF receptor insert (4.5 kb) with respect to the SV40 promoter, the positive clones were digested with SmaI endonuclease which cuts at position 573 of the receptor sequence and in the polylinker region of the expression vector.

Clones containing the receptor in the proper transcriptional orientation released a 4.0 kb insert in addition to the 3.2 kb fragment containing the expression vector plus 573 base pairs of the 5' end of the receptor. This plasmid, PSVRH5 was used to co-transfect cells with PSV2 neo plasmid that confers resistance to the antibiotic neomycin.

III. Cell Culture and Transfection of CHO Cells

CHO cell clone KI, obtained from the U.C.S.F. Tissue Culture Facility, were grown in Ham's F-12 media supplemented with 10% FCS (UCSF Tissue Culture Facility) and penicillin and streptomycin at 37° C. in 5% $CO_2$/95% air.

pSVRH5 plasmid DNA (10 µg) and pSV2 neo (1 µg) were used to co-transfect $1\times10^6$ CHO cells by the calcium precipitation technique of Van der Eb et al. (1980), *Methods in Enzymology* (1980) 65:826–839, with the addition of 10 µg chloroquinone diphosphate (CDP) to prevent degradation of the transfected DNA. After 12 h of exposure to the DNA, the cells were trypsinized and replated at 1:5 dilution. Twenty-four hours later, the antibiotic G418 (GIBCO), an analog of neomycin, was added to the cultures at a concentration of 400 µg/ml.

After two weeks under selection, independent colonies were picked and transferred to 24-well plates. Confluent cultures were assayed for the presence of PDGF receptor by immunoblot using anti-receptor antibodies. Colonies that were positive by this assay were single-cell cloned by end-limiting dilution.

Stable transfected clones were tested for the expression of the type B PDGF receptor message measured by RNA protection assays and for the presence of PDGF-stimulated receptor protein detected by anti-phosphotyrosine antibodies.

IV. Expression of B-hPDGF-R cDNA in CHO Cells

CHO cells transfected with plasmid DNA containing the human receptor cDNA under the transcriptional control of the SV40 early promoter (CHO-HR5) and CHO cells transfected with a similar plasmid containing the mouse receptor cDNA (CHO-R18) were solubilized as previously described by Escobedo et al. (1988) *J. Biol. Chem.* 263:1482–1487. Extracts were analyzed by Western blot analysis using an antibody that specifically recognizes sequences in the receptor carboxyl-terminal region as previously described by Escobedo et al. (1988) *J. Biol. Chem.;* and Keating et al. (1987) *J. Biol. Chem.* 262:7932–7937.

The 195 kDa protein is the mature receptor and the 160 kDa protein is the receptor precursor.

The expression of the receptor protein in the transfectants was demonstrated by using antibodies that recognize an intracellular sequence in the receptor. The clone that had the highest level of human receptor expression was chosen for further study. This transfectant had receptors that were labeled with $^{125}$I-PDGF as shown by the competitive binding studies described below.

V. Competitive Binding of the Different Forms of PDGF to the Type B Receptor

The ability of the human recombinant AA and BB homodimers to compete for the type B receptor sites and displace $^{125}$I-labeled PDGF (prepared as described below) was studied. Each homodimer was produced selectively by a yeast expression system and was purified from yeast media that is devoid of other mesenchymal cell growth factors, thus avoiding the artifact of contamination by factors that might be present in mammalian expression systems.

BALB/c 3T3 cells and CHO transfectants (CHO-HR5) were incubated with $^{125}$I-PDGF in the presence of increasing concentrations of AA or BB. Binding was carried out at 37° C. for 45 min in whole cell suspension. Unbound, radiolabeled PDGF was removed by centrifugation on a Ficoll gradient Non-specific binding, determined by incubating CHO cells with $^{125}$I-PDGF, accounted for 25 percent of the bound radioactivity.

The binding study demonstrated that the transfected cells can be used as a model to study the interaction of hPDGF with its receptor. In particular, this study demonstrated that the transfected type B human receptor was functionally equivalent to the native mouse receptor as indicated by the following results. Both AA and BB forms of PDGF competed for the $^{125}$I-PDGF labeled sites in the human receptor transfectants. For the transfected type B human receptor as well as the native mouse receptor, the BB form was of higher affinity than the AA form. When expressed in yeast, the AA form of PDGF may be processed aberrantly, giving it a lower affinity than the BB form for both the transfected cells and mouse 3T3 cells. The consistency of the pattern of competition shows that the AA form interacts with the transfected type B human receptor in the same way as it does with the native mouse receptor and demonstrates that these receptors are functionally equivalent.

VI. Activation of the PDGF Receptor Tyrosine Kinase

The ability of recombinant AA and BB homodimers and of human partially purified AB PDGF to activate the type B receptor tyrosine kinase was studied. The yeast-derived AA and BB homodimeric forms and the platelet-derived AB form stimulated autophosphorylation of the transfected human receptor.

BALB/c 3T3 cells and CHO cells transfected with the human PDGF receptor cDNA (CHO-HR5) were incubated with increasing amounts of the different forms of PDGF (AA, BB and AB). Following polyacrylamide-SDS electrophoresis, the phosphorylated receptor was identified by Western blot using an anti-phosphotyrosine antibody.

The receptor protein co-migrated with the 200 kDa molecular weight marker. The concentration of each form that was effective in stimulating autophosphorylation of the transfected human receptor was equivalent to the concentration that gave a similar autophosphorylation to the native mouse 3T3 receptor or the transfected mouse receptor.

These results showed for the first time that the AA form of PDGF activates the receptor tyrosine kinase of the type B receptor. Prior to use of the transfected cells, there was no demonstration that the AA form had hPDGF activity or that a single receptor, the type B receptor, was capable of recognizing all three forms of PDGF. Further, the results demonstrate that the human cDNA encodes a type B receptor that is functionally equivalent to the wild-type receptor that is responsible for PDGF-stimulated tyrosine kinase activity in mouse 3T3 cells.

Thus, the transfected cells are useful models for studying PDGF-induced mitogenic responses.

VII. Rate of DNA Synthesis in CHO Transfected Cells

BALB/c 3T3 cells and CHO cells transfected with the type B human PDGF receptor cDNA (CHO-HR5) were incubated with saturating concentrations of the three forms of PDGF. Untreated cells and cells treated with fetal calf serum (FCS) were used as negative and positive controls, respectively. The level of $^3$H-thymidine incorporation into DNA was determined by measuring the radioactivity of the acid-precipitable material as previously described.

Transfection of CHO cells with either type B human or mouse PDGF receptor conferred a PDGF-sensitive mitogenic response. All forms of PDGF stimulated DNA synthesis in both the type B human receptor transfectant and the mouse cells bearing the native receptor.

These data showed that the A chain homodimer and the B chain homodimer, like the AB platelet-derived form, were mitogens that can act through the receptor encoded by the type B human cDNA sequence. The mitogenic action of these forms of PDGF on mouse 3T3 cells and CHO cells containing the transfected type B human receptor demonstrate that the responses were mediated by functionally equivalent receptors.

VIII. Isolation and Expression of the Type A PDGF Receptor

The type A receptor was isolated as described for the type B receptor, above, except that different probes were used and hybridization and screening were performed under low stringency conditions, as described below. In particular, a region in the type B receptor tyrosine kinase sequence having a high degree of homology to published tyrosine kinase amino acid sequences was identified and had the amino acid sequence, HRDLAARN (amino acid residues 816–823 of SEQ ID NO:2). Oligonucleotide probes encoding the tyrosine kinase consensus sequence were prepared having the following sequences (SEQ ID NO:14):

GTT(G/C)CGXGCXGCCAGXTC(G/C)CGXTG, where G/C indicates either G or C was used and X indicates any of A, T, C or G was used. The human placenta λGT10 cDNA library was screened as described above but with low stringency conditions using a buffer with 6×SSC 0.1% SDS and 5×Denhardt's solution at 42° C. as follows. Filters were screened by washing at 52° C. in 2×SSC. A clone encoding the type A receptor was isolated and sequenced by the procedure described for the type B receptor gene.

The DNA sequence of the gene encoding the type A receptor (A-hPDGF-R) together with the deduced amino acid sequence are shown in Table 3, above.

The clone encoding A-hPDGF-R was digested, gel purified and inserted into the SV40 expression vector, pSV7C, as described for the type B receptor clone.

That vector is used to transfect CHO cells as described above for the type B receptor. With expression of the vector coding sequence, transfected CHO cells produce a functional receptor that binds all three -hPDGF forms, preferentially binding the AA homodimer.

IX. Extracellular Murine PDGF-R Fragments Construction of pSV-SRXld Expression Vector and Transfection of DUKX-B11 Cells With a Murine Extracellular Region To express the secreted extracellular region (XR) of PDGF type B receptor (type B PDGF-R), a cDNA clone of the murine PDGF-R was mutagenized to introduce a Stu I restriction site between codons 500 and 501, changing codon 500 from valine to arginine. The 1.7 kb EcoRI-Stu I fragment was inserted into pIBI-25 (IBI) which added an in-frame proline codon followed by a stop codon at the C-terminus. The 1.7 kb Eco RI-Xba I fragment was transferred to pSV-7DHFR in which the XR expression was driven by the SV-40 early promoter and the amplifiable marker, a dihydrofolate reductase (dhfr) transcriptional unit, was driven by an Adenovirus major late promoter. The complete plasmid encodes the signal sequence and the first 499 amino acids (the extracellular region) of the PDGF-R, followed by arginine, proline and stop codons.

The cDNA was expressed in dhfr-deficient CHO mutant cells, DUKX-B11. DUKX-B11 cells were transfected to 10-cm tissue culture plates with 5 µg of pSV-SRX1d plasmid and selected for expression with nucleoside-free MEM-α (Gibco) supplemented with 10% dialyzed calf serum, 200 µg/ml proline, 100 U/ml penicillin, and 100 µg/ml streptomycin. Colonies were picked and screened by analyzing the conditioned media by SDS-PAGE and Western blotting with a polyclonal PDGF-R antibody directed against the extracellular region of the receptor (Ab77).

Amplification of Murine Extracellular Region Expression by Methotrexate

Positive transfectants were treated sequentially with increasing concentrations of methotrexate starting at 1, 2, 5, and 10 nM. Colonies from the highest concentrations were then treated with 10 fold higher concentrations of methotrexate (20, 50, and 100 nM). Colonies from the highest concentrations were again picked and treated with increasing concentrations of methotrexate. The conditioned media from colonies at each stage were analyzed by SDS-PAGE and Western blotting with an anti-PDGF-R Ab (Ab77) for expression of the extracellular region protein. Methotrexate-resistant (5 µM) cells that secreted highest amount of the extracellular region protein were named DPXR (DUK-PDGF-R extracellular region) cells.

Enzymatic treatments of the extracellular region protein with O-glycanase (Genzyme Co.) and N-glycanase (Genzyme Co.) were performed. Briefly, extracellular region protein partially purified with wheat germ agglutinin (WGA) affinity chromatography (50 nM, in 20 mM sodium phosphate, pH 7.4) was incubated with N-glycanase (10 U/ml) overnight at 37° C. and then with O-glycanase (2 mU/ml) for an additional 2 h. The sample was then boiled for 5 min and analyzed with SDS-PAGE and Western blotting with Ab77.

Conditioned Media

DPXR cells at 95% confluence were washed twice with serum-free DME H21 medium. Four ml of DME H21 medium supplemented with 10% protein-free Serum Substitute (UCSF Cell Culture Facility) was added to each 10-cm culture plate. Conditioned media containing murine extracellular region polypeptide which were used for various assays were collected from DPXR cells over 48 h unless otherwise mentioned.

Preparation of $^{125}$I-BB-PDGF

BB-PDGF (gift from Chiron Corporation) was iodinated. Briefly, 2.5 µg of BB-PDGF were rotary-evaporated in a silanized polypropylene tube. BB-PDGF was resuspended in 10 µl of 0.1 M sodium borate (pH 8.5). $^{125}$I-mono-iodo Bolton Hunter reagent (500 µCi; Amersham) was dried under nitrogen. The BB-PDGF was added to the dry Bolton Hunter reagent and incubated for 15 min at 4° C. Fifty µl of quench solution (0.1 M sodium borate, 0.2 M glycine, pH 8.5) was added to the reaction mixture, which was incubated for an additional 10 min at 4° C. The entire reaction mixture was loaded on a PD-10 column (Pharmacia) equilibrated with 0.1 M acetic acid containing 1 mg/ml BSA (ICN Biochemicals), and eluted with the same buffer.

X. Binding Assays

Of relevance to the production of soluble fragments of PDGF receptor polypeptides, and assays for their use, are techniques and results reported in Kimball and Warren (1984) *Biochim. Biophys. Acta* 771:82–88; van der Schaal et al. (1984) *Anal. Biochem.* 140:48–55; van Driel et al. (1989) *J. Biol. Chem.* 264:9533–9538; Heldin et al. (1988) *EMBO J.* 7:1387–1393; Williams et al. (1982) *Proc. Nat'l Acad. Sci. USA* 79:5867–5870; Williams et al. (1984) *J. Biol. Chem.* 259:5287–5294; and particularly, Orchansky et al. (1988) "Phosphatidylinositol Linkage of a Truncated Form of the Platelet-derived Growth Factor Receptor" *J. Biol. Chem.* 263:15159–15165; each of which is hereby incorporated herein by reference. In particular, the Orchansky publication provides evidence that a whole extracellular region of a PDGF receptor, when separated from the TM and intracellular regions, still is capable of binding to PDGF ligands.

In whole cell binding assays, $2 \times 10^4$ R18 cells (PDGF type B receptor transfectant CHO cells) detached with PBS/EDTA (2 mM) were incubated with 10 µl of platelet-poor plasma, and PBS/Hepes (25 mM final, pH 7.4). Conditioned media, 12.5 µl to 200 µl, from DPXR cells (collected as described above), which contain the extracellular region protein, were added to the binding mixtures in a final volume of 250 µl to form 20 to 1.25 fold dilutions. The mixtures were shaken overnight at 4° C. and spun through 750 µl of Ficoll gradient (28.5% Ficoll-Paque (Pharmacia) in PBS) at 4° C. The supernatants were aspirated and the radioactivity in the cell pellets was determined with a gamma-counter.

To measure its affinity for BB-PDGF, extracellular region protein was immobilized by adsorption onto a plastic surface. 50 µl of WGA affinity chromatography purified extracellular region (approximately 80 nM, estimated by silver straining) was diluted in 10 ml of 25 mM Tris Cl, 75 mM NaCl, 20 mM $NH_4HCO_3$, pH 7.5, and 100 µl aliquots were plated in each well of 96-well ELISA microtiter plates (Dynatech Products Co.). After overnight incubation at 4° C., the plate was washed once and blocked with 0.5% gelatin in 100 mM NaCl, 25 mM Hepes, pH 7.35, for 3 h at 4° C. The plate was then washed twice with binding buffer (0.3% gelatin, 100 mM NaCl, 25 mM Hepes, pH 7.35). $^{125}$I-BB-PDGF and/or unlabeled BB-PDGF were added to the wells in a final volume of 100 µl and the plate was incubated at 4° C. for 16 h for steady state binding. The plate was washed three times again with binding buffer and stripped with 200 µl of 1% SDS, 0.5% BSA for counting in a gamma-counter.

Crosslinking Experiments

Extracellular region polypeptide partially purified by WGA chromatography (25 µl, ~50 nM) was incubated with 0.2 µCi of 125I-BB-PDGF (2 nM final concentration) and various concentrations of unlabeled BB-PDGF in a final volume of 100 µl at 4° C. for 3 h. The extracellular region protein was then crosslinked to the ligand by 1 mM bis (sulfosuccinimidyl) suberate ($BS^3$) (cat. #21579, Pierce Chemicals, Rockford, Ill.) at room temperature for 30 min. The reaction was stopped by 25 mM Tris buffer, pH 7.4, for 5 min. The extracellular region protein was then immunoprecipitated with a receptor antibody (Ab77) and analyzed by SDS-PAGE.

Autophosphorylation Assay

Conditioned media containing the extracellular region protein (1 ml) were incubated with BB-PDGF for 3 h at 4° C. The mixtures were then added to the 6-well Falcon tissue culture plates (1 ml/well) which contained monolayers of quiescent human PDGF A-receptor transfectant CHO cells or BALB/c 3T3 cells. The cells were incubated with the mixtures for 10 min at 37° C. and then washed with serum-free DME medium and lysed with Ripand lysis buffer. Cell lysates were analyzed by SDS-PAGE and Western blotting with an anti-phosphotyrosine mAb.

Mitogenesis Assay

BALB/c 3T3 cells were plated in 96-well tissue culture plates for 3 days and made quiescent with Q-media (DMEM with 1 mg/ml insulin, 2 µg/ml transferrin and 0.5 mg/ml BSA) for 24 h. Conditioned media containing the extracellular region protein was diluted in 2-fold serial dilutions with fresh DME H21 medium, preincubated with 2 nM BB-PDGF for 3 h at 4° C. and then added to BALB/c 3T3 cells (200 µl/well). The cells were incubated for 18 h at 37° C. One µCi [$^3$H]-thymidine (in 50 µl) was then added to each well for 4 h. The cells were washed twice with cold PBS and fixed with cold trichloracetic acid (TCA, 5%). Precipitated cell debris were then washed extensively with cold TCA (5%) and dissolved in 0.25 N NaOH for scintillation counting.

XI. Human Extracellular Region

Equivalent techniques for construction, expression, and determination of the physiological effect of truncation or deletion analogues of the soluble extracellular receptor fragments from the human receptor may be performed using the nucleic acid, polypeptide, and other reagents provided herein.

Human Deletion and Truncation Constructs

PDGF-R Constructs

Figure 8:
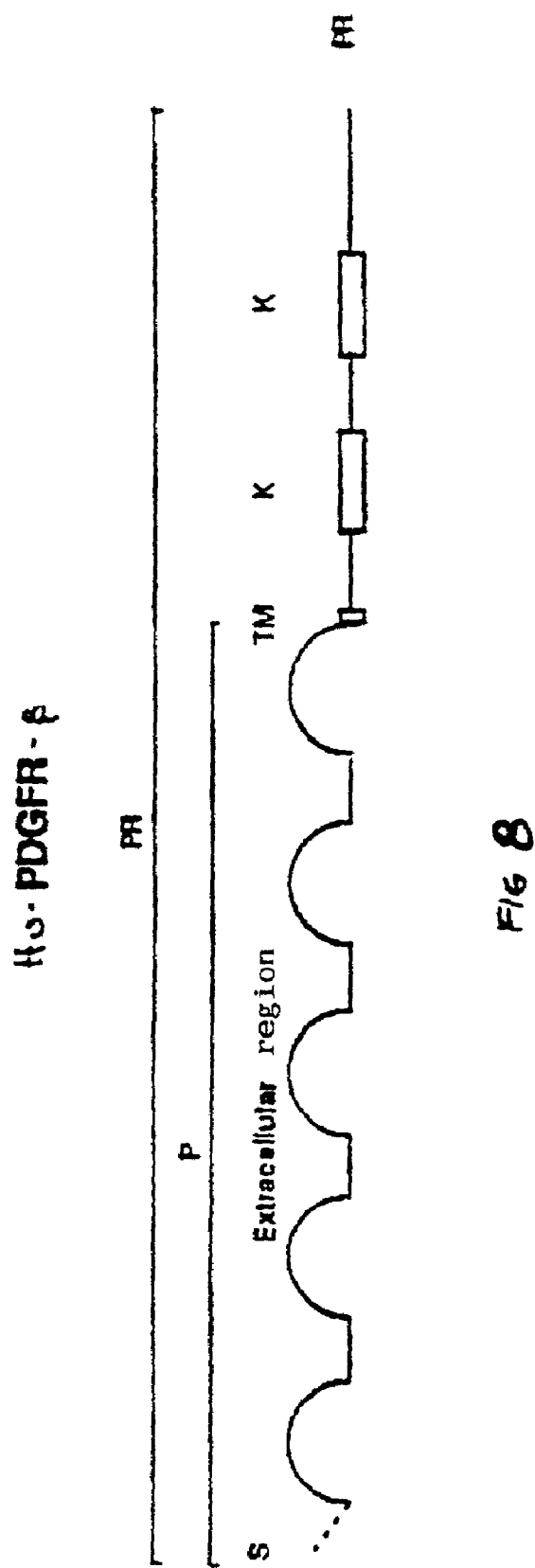
FIG. 8 illustrates a strategy for oligonucleotide directed in vitro production of a soluble hPDGF-R extracellular region. The abbreviations used are:
PR=PDGFR; intact
P=PDGFR; extracellular region
TM=transmembrane region
K=kinase
S=signal sequence

The 3.9 kb EcoRI-Hind III cDNA fragment of the human type B hPDGF-R was subcloned into the EcoRI-Hind III site of M13 Mp18 to produce a vector Mp18PR. For techniques, see Maniatis et al., *Molecular Cloning: A Laboratory Manual* (1982), Cold Spring Harbor, N.Y., which is incorporated herein by reference. Verification of subcloning was performed by restriction enzyme digestion analysis and dideoxy chain termination sequencing, as described by Sanger et al. (1977) *Proc. Nat'l Acad. Sci. USA* 74:5463. oligonucleotide directed in vitro mutagenesis was performed according to the method described by Kunkel et al. (1987) *Methods in Enzymol.*, 154:367. The strategy for oligonucleotide directed in vitro deletion mutagenesis of Mp18PR is outlined in FIG. 8. In brief, an oligonucleotide was designed to create a soluble type B hPDGF receptor extracellular region by deletion mutagenesis. A mutagenic oligonucleotide aligned with the appropriate region of the human PDGF receptor can be used to generate deletions. The antisense strand was used for mutagenesis throughout. Mutagenesis of PΔ1 utilized Mp18PR as the template. PΔ1, a 41 bp oligomer, introduced a TAG stop codon after $Lysine_{499}$ ($K_{499}$) of D5 and removed the transmembrane (TM) as well as the entire intracellular kinase domain (K), producing an Mp18 PΔ1. PΔ1 codes for $530_{aa}$ $148_{aa}$ precursor proteins.

The human PDGF receptor constructs were subsequently subcloned into the EcoRI-Hind III site of pBJ1 a derivation of pCDL-SRα296, as described in Takabe et al. (1988)

*Molec. Cell Biol.* 8:466, and co-transfected with pSV2NEO, as described by Southern and Berg (1982) *J. Mol. Appl. Gen.*, 1:327, into Chinese hamster ovary cells (CHO).

Function of the construct was demonstrated as follows:

A sample of 0.33 nM PDGF BB ligand is preincubated for 1 hr at 4° C. under the following conditions:
1. a polyclonal antibody to human PDGF (this antibody recognizes human PDGF AA, PDGF BB and PDGF AB);
2. 18 nM (60 fold molar excess to PDGF BB) human type B PDGF receptor;
3. phosphate buffered saline solution that the receptor and antibody are in; or
4. no additions but the ligand itself.

In a duplicate set of experiments, 0.33 nM PDGF AA is incubated with three of the above preincubation conditions, e.g., 2, 3, and 4 above. The human type B PDGF receptor does not appreciably recognize PDGF AA but this ligand will still activate cell-associated human type A PDGF receptor from NIH3T3 cells and so is a control for human type B PDGF receptor specificity and PDGF BB-dependent activation versus non-specific general cellular effect, e.g., cytotoxicity.

The preincubated materials were in a final volume of 0.5 ml. They were placed in one well each of a six well tissue culture dish containing a confluent layer of serum starved (quiescent) NIH3T3 cells which were chilled to 4° C. The cells and incubation mixtures were agitated, e.g., rocked, at 4° C. for 2 h. They were then washed twice with 4° C. phosphate buffered saline. Forty µl of 125 mM Tris(hydroxymethyl)amino methane (Tris), pH 6.8, 20% (v/v) glycerol, 2% (w/v) sodium dodecyl sulfate (SDS), 2% (v/v) 2-mercaptoethanol, and 0.001% bromphenol blue, (known as SDS sample buffer), was added per microtiter well followed by 40 µl of 100 mM Tris, pH 8.0, 30 mM sodium pyrosphosphate, 50 mM sodium fluoride, 5 mM ethylenediaminetetraacetic acid (EDTA), 5 mM ethylenebis(oxyethylenenitrilio)tetraacetic acid, 1% (w/v) SDS, 100 mM dithiothreitol, 2 mM phenylmethylsulfonylfluoride (PMSF), and 200 µM sodium vanadate was added to the cells. The cells were solubilized and 40 µl additional SDS sample buffer was added to the solubilizate. This material was boiled 5 minutes and loaded onto a single gel sample well of a 7.5% sodium dodecyl sulfate polyacrylamide gel. Cellular proteins were separated by electrophoresis.

The separated proteins were transferred to nitrocellulose by electrotransfer and the resulting "Western blot" was incubated with 3 changes of 0.5% (w/v) sodium chloride, 5 mg/ml bovine serum albumin, 50 mM Tris, pH 7.5, (designated blocking buffer) for 20 minutes each at room temperature. A 1/1000 dilution of PY20 (a commercially available monoclonal antibody to phosphotyrosine [ICN]) in blocking buffer was incubated with the blot overnight at 4° C. The blot was washed 3 times for 20 minutes each at room temperature in blocking buffer. The blot was incubated with 4 µci/40 ml of $^{125}$I-Protein A [Amersham] in blocking buffer for 1 hour at room temperature and washed 3 times for 20 minutes each at room temperature in blocking buffer. The blot was exposed to X-ray film for 48 h with one intensifying screen at −70° C. and developed with standard reagents.

XII. PDGF Plate Assay

Polystyrene microtiter plates (Immulon, Dynatech Laboratories) were coated with the extracellular region fragment of the type B human PDGF receptor (described above) by incubating approximately 10–100 ng of this protein per well in 100 µl of 25 mM Tris, 75 mM NaCl, pH 7.35 for 12 to 18 h at 4° C. The protein was expressed in transfected CHO cells and collected in serum-free media (Gibco MEMα) at a concentration of 0.2–1 µg/ml, with a total protein concentration of 150–300 µg/ml.

The human type B PDGF receptor extracellular region fragment was concentrated and partially purified by passing the media over wheat germ-agglutinin-sepharose at 4° C. (at 48 ml/h) in the presence of 1 mM PMSF. After extensive washing, the protein was eluted in 0.3 M N-acetyl-glucosamine, 25 mM Hepes, 100 mM NaCl, 1 mM PMSF, pH 7.4. This fraction was then applied to Sephacryl S-200 HR (Pharmacia) equilibrated in 0.15 M ammonium bicarbonate pH 7.9. The fractions containing receptor (3–10 ng/µl) were detected by SDS-PAGE and Western blotting with a polyclonal rabbit antibody against a peptide from the receptor external region. These fractions (3–10 ng/µl) were used to coat the microtiter wells as described above. The wells were then drained, rinsed once with 200 µl each of 0.5% gelatin (Bio-Rad, EIA grade), 25 mM Hepes, 100 mM NaCl, pH 7.4, and incubated for 3 h at 4° C. with 150 µl of this same solution. The wells were drained and rinsed twice with 0.3% gelatin, 25 mM Hepes, 100 mM NaCl, pH 7.4 (150 µl each). The plate was put on ice and 90 µl of the 0.3% gelatin solution was put in each well (wells used to test nonspecific binding received just 80 µl and then 10 µl of 0.01 mg/ml non-labeled PDGF in the 0.3% gelatin solution). PDGF BB (Amgen) was iodinated at 4° C. to 52,000 CPM/ng with di-iodo Bolton-Hunter reagent (Amersham) and approximately 40,000 CPM was added per well in 10 µl, containing 0.024% BSA, 0.4% gelatin, 20 mM Hepes, 80 mM NaCl, 70 mM acetic acid, pH 7.4. The plate was incubated for 4 h at 4° C., after which wells were washed three times with 150 µl each with 0.3% gelatin, 25 mM Hepes, 100 mM NaCl, pH 7.4 at 4° C. The bound radioactivity remaining was solubilized from the wells in 200 µl 1% SDS, 0.05% BSA, and counted in a gamma-counter. The nonspecific binding was determined in the presence of a 150-fold excess of unlabeled PDGF BB (Amgen) and was about 7% of the total bound $^{125}$I-PDGF.

These studies were made possible by the availability of growth factor preparations devoid of contamination with other growth factors and by the use of a receptor expression system in which all of the measured PDGF responses could be attributed to this single transfected receptor cDNA.

XIII. Intracellular Region Cell Culture and Recombinant Baculovirus.

BALB c/3T3 cells clone A31 from C. D. Scher, Children's Hospital of Philadelphia, Pa., were cultured in Dulbecco Modified Eagle's medium (DMEM) supplemented with 10% bovine serum and penicillin and streptomycin (50 µg/ml each). *Spodoptera frugiperda* (Sf9) cells (from M. Summers, Texas A&M, TX) were grown in Grace's medium supplemented with 10% fetal bovine serum, 3.3 g/l yeastolate, 3.3 g/l lactalbumin hydrolysate, and penicillin and streptomycin 50 µg/ml each. Recombinant type B PDGF receptor and PDGF type B receptor ΔKI mutant baculovirus vectors were prepared by standard procedures. Recombinant baculovirus was collected from supernatant of Sf9 cells 48–60 hours after infection at a multiplicity of infection (MOI) of 1.

Antibodies, Mitogens, and Peptides

A type B PDGF receptor antibody (Ab77) directed against a synthetic peptide (amino acids 425–446) located at the extracellular region was used. PLC-γ monoclonal antibody was kindly provided by S. G. Rhee, NIH, Bethesda, Md., and GAP antibodies were provided by F. McCormick, Cetus Corp., Emeryville, Calif. Recombinant BB-PDGF was provided by C. G. Nascimento from Chiron Corp. Emeryville, Calif. Peptides used in the association experiments were prepared by conventional peptide synthesis using phosphorylated tyrosine (N-Boc-Tyr-o-[PO$_3$Bzl$_2$], Peninsula Laboratory, Belmont, Calif.) for the synthesis of tyrosine phosphorylated peptides.

Association Assays

In vivo associations were performed according to Morrison et al. (1989) Cell 58:649–657. Serum starved cultures of BALB c/3T3 cells (10$^7$ cells) were incubated in the presence or absence of 2 nM PDGF. Cell lysates were immunoprecipitated by using receptor antibody or phosphotyrosine antibodies. Immune complexes were used assayed for the presence of PI3 kinase activity and to determine the protein that associated with the receptor. In vitro association experiments were performed according to Morrison et al (1989) or Morrison et al. (1990) Mol. Cell. Biol. 10:2359–2366. Typically, baculovirus-expressed type B PDGF receptor was collected from Sf9 cells 48–60 hours after infection (MOI: 10) by immunoprecipitation using receptor antibodies. Infected cells were washed twice with cold PBS and lysed in 1 ml of lysis buffer (1% NP-40, 20 mM Tris (pH 8.0), 173 mM NaCl, 10% glycerol, 2 mM EDTA, 1 mM phenylmethylsulfonylfluoride (PMSF), aprotinin (0.15 U/ml), 20 µM leupeptin, 1 mM sodium orthovanadate) at 4° C. for 20 min with rocking. In most experiments (except where indicated in the legend of FIG. 3) the immunoprecipitated receptor was autophosphorylated in vitro by incubating the immune complexes in a buffer containing 20 mM Tris (pH 7.5), 20 mM MnCl, 100 µM ATP for 15 min at 25° C. Lysates were cleared of insoluble material by centrifugation at 13,000× g for 10 min. Lysates were incubated with receptor antibodies (1:500 dilution) for 4 h at 4° C. Receptor-antibody complexes were precipitated using Protein-A sepharose (Sigma) and washed consecutively with RIPA buffer (lysis buffer with 0.1% SDS), wash buffer 1 [0.5% NP-40, 0.5 M LiCl, 50 mM Tris (pH 7.4)] and with 10 mM Tris (pH 7.4). The PI3 kinase association assay was performed by incubating the immobilized receptor with BALB c/3T3 cell lysates for 3 hours at 4° C. The immune complexes were consecutively washed with cold PBS; 0.5% NP-40, 0.5 M LiCl and 50 mM Tris (pH 7.4). In the experiment using peptides the BALB c/3T3 lysates were preincubated with the peptides (50 µM) for 30 min at 4° C. prior to the incubation with the PDGF receptor protein expressed in the insect cell system.

In Vitro Kinase and PI3 Kinase Assays

In vitro protein kinase assays were performed by incubation of the immunoprecipitates in protein kinase buffer (30 mM Tris (pH 7.4), 10 mM MnCl$_2$) and 10 µCi [γ-$^{32}$P]-ATP 3,000 Ci/mmol, at 25° C. for 15 min. The reaction was terminated by adding 4×Laemmli loading gel buffer. Samples were analyzed by SDS-polyacrylamide gel electrophoresis and autoradiography. PI3 kinase activity was assayed as described by Kaplan et al. (1986) Proc. Nat'l Acad. Sci. USA 83:362–364. Immune complexes were incubated in PI3 kinase buffer (30 mM Hepes (pH 7.4), 30 mM MgCl$_2$, 200 µM adenosine, 40 µM ATP), 0.2 mg/ml of sonicated phosphoinositol (PI), and 10 µCi [(γ-$^{32}$P]-ATP (3,000 Ci/mmol) at 25° C. for 10 minutes. Adenosine was added in the PI3 kinase assays to inhibit any contaminating P14 kinase activity. Reactions were terminated by the addition of 100 µl of HCl acid. The products of the reaction were extracted with chloroform and separated by thin layer chromatography. The conversion of PI into PIP was determined by exposing the TLC plate to an X-ray film for 2–3 h.

Receptor Dephosphorylation

Receptor immunoprecipitates were incubated for 30 minutes at 30° C. with 4 µg of potato acid phosphatase in the presence or absence of 1 mM sodium orthovanadate, see Morrison et al. (1989). After RAP treatment the immunoprecipitates were washed three times with RIPA buffer containing 1 mM sodium orthovanadate prior to the incubation with the 3T3 cell lysate.

"Blotting" of 85 kD Protein with PDGF Receptor Probe

Cell lysate proteins transferred to nitrocellulose membranes were analyzed for their ability to bind directly to the PDGF receptor by probing the nitrocellulose membrane with $^{32}$P-labeled PDGF receptor. To prepare the radiolabeled receptor probe, baculovirus-expressed receptor was immunoprecipitated from 10$^6$ Sf9 cells. The immune complexes were washed and labeled by autophosphorylation as described above. Labeled receptor was solubilized from the immunoprecipitates by repeated incubation of the immunoprecipitate in solubilization buffer (0.4% SDS, 100 mM NaCl, 2 mM EDTA, 2 mM β-mercaptoethanol, and 50 mM triethanolamine, pH 7.4) at 100° C. for 2 min. The extracts were pooled, diluted in solubilization buffer without β-mercaptoethanol and brought to 10 mM iodoacetamide and 1% Triton X-100. Analysis of this material by SDS-polyacrylamide electrophoresis followed by radioautography revealed the presence of only the receptor band. BALB c/3T3 cells lysates were prepared and run on SDS-PAGE. Proteins were transferred onto nitrocellulose filter by electroblotting in the absence of SDS. Filters were incubated with radiolabeled PDGF receptor for 12 h at 4° C., and washed in the solubilization buffer containing 2% Triton X-100 without β-mercaptoethanol. For the peptide competition experiments the filters were incubated as described above with the $^{32}$P-Labeled receptor probe and 2.5 µM of the indicated peptide.

All publications and patent applications herein are incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

What is claimed is:

1. A method of selecting a molecule capable of inhibiting binding of a PI3 kinase protein which binds to a PDGF receptor polypeptide, the method comprising the steps of:
  contacting the PI3 kinase protein with the PDGF receptor polypeptide in the presence of a test molecule in a first step;
  contacting the PI3 kinase protein with the PDGF receptor polypeptide in the absence of the test molecule in a second step;
  wherein the PDGF receptor polypeptide is selected from the group consisting of
    i) a polypeptide consisting of amino acids beginning at 695 and ending at 798 of a B type hPDGF-R, as shown in SEQ ID NO: 4,
    ii) a polypeptide consisting of amino acids beginning at 604 and ending at 951 of a B type hPDGF-R, as shown in SEQ ID NO: 4,
    iii) a polypeptide consisting of amino acids beginning at 695 and ending at 951 of a B type hPDGF-R, as shown in SEQ ID NO: 4, and
    iv) a polypeptide consisting of amino acids beginning at 557 and ending at 951 of a B type hPDGF-R, as shown in SEQ ID NO: 4;
  wherein the polypeptide is phosphorylated at Tyr 751 or at Tyr 740; and
  comparing the amount of PDGF receptor binding to PI3 kinase in the first and second steps, wherein a lower level of binding detected in the first step is an indication that the test molecule is capable of inhibiting binding of PI3 kinase to PDGF receptor polypeptide, thereby selecting a molecule capable of inhibiting binding of a PI3 kinase protein to a PDGF receptor polypeptide.

2. The method of claim 1, wherein the test molecule is selected from the group consisting of peptides, peptide analogues, organic analogue molecules and drugs.

3. The method of claim 1, wherein the amount of PDGF receptor binding to PI3 kinase is detected using a protein kinase activity assay.

4. The method of claim 1, wherein the polypeptide is phosphorylated at Tyr 740.

5. The method of claim 1, wherein the polypeptide is phosphorylated at Tyr 751.

6. The method of claim 1, wherein the polypeptide is phosphorylated at Tyr 751 and at Tyr 740.

* * * * *